(12) United States Patent
Daines et al.

(10) Patent No.: US 9,988,693 B2
(45) Date of Patent: *Jun. 5, 2018

(54) GENETIC LOCI ASSOCIATED WITH RESISTANCE OF SOYBEAN TO CYST NEMATODE AND METHODS OF USE

(71) Applicant: PIONEER HI-BRED INTERNATIONAL, INC., Johnston, IA (US)

(72) Inventors: Bryce Reid Daines, Johnston, IA (US); David Hyten, Johnston, IA (US); Nichole Lynn Schneider, Stuart, IA (US); John Bryan Woodward, Ankeny, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 8 days.

This patent is subject to a terminal disclaimer.

(21) Appl. No.: 15/146,109

(22) Filed: May 4, 2016

(65) Prior Publication Data

US 2016/0237510 A1 Aug. 18, 2016

Related U.S. Application Data

(62) Division of application No. 13/779,957, filed on Feb. 28, 2013, now Pat. No. 9,347,105.

(60) Provisional application No. 61/740,526, filed on Dec. 21, 2012, provisional application No. 61/671,937, filed on Jul. 16, 2012, provisional application No. 61/660,387, filed on Jun. 15, 2012.

(51) Int. Cl.
| | |
|---|---|
| C12Q 1/68 | (2018.01) |
| C12N 15/82 | (2006.01) |
| A01H 5/10 | (2018.01) |
| C07K 14/415 | (2006.01) |

(52) U.S. Cl.
CPC ............ *C12Q 1/6895* (2013.01); *A01H 5/10* (2013.01); *C07K 14/415* (2013.01); *C12N 15/8285* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,491,081 A | 2/1996 | Webb | |
| 6,096,944 A | 8/2000 | Vierling et al. | |
| 6,162,967 A | 12/2000 | Webb | |
| 6,300,541 B1 | 10/2001 | Lightfoot et al. | |
| 6,538,175 B1 | 3/2003 | Webb | |
| 7,154,021 B2 | 12/2006 | Hauge et al. | |
| 7,485,770 B2 | 2/2009 | Hauge et al. | |
| 7,872,171 B2 | 1/2011 | Webb | |
| 9,347,105 B2 * | 5/2016 | Daines ............... | C12Q 1/6895 |
| 2002/0144310 A1 | 10/2002 | Lightfoot et al. | |
| 2004/0031072 A1 | 2/2004 | La Rosa et al. | |
| 2009/0100537 A1 | 4/2009 | Concibido et al. | |
| 2010/0240061 A1 | 9/2010 | Butruille et al. | |
| 2011/0083234 A1 | 4/2011 | Nguyen et al. | |
| 2012/0192315 A1 | 7/2012 | Lightfoot | |
| 2013/0305410 A1 | 11/2013 | Bent | |
| 2013/0340115 A1 | 12/2013 | Daines | |

FOREIGN PATENT DOCUMENTS

| | | |
|---|---|---|
| WO | 2001/051627 A2 | 7/2001 |
| WO | 2012/025864 A1 | 3/2012 |

OTHER PUBLICATIONS

Thomas, 1985, J. Opt. Soc. Am. 2: 1457-1467.*
Yue et al., 2000, Euphytica 116: 181-186.*
Smiley et al., Pacific Northwest Extension Publication, 2010, PNW 620, pp. 1-9.*
Matsye et al., 2012, Plant Mol. Biol. 80: 131-155.*
Bent, Andrew, et al., "SCN Resistance Determinants at the Rhg1 Locus," Molecular & Cellular Biology of the Soybean Conference, Aug. 12-15, 2012, Abstract.
Cook, David E., et al., "Copy Number Variation of Multiple Genes at Rhg1 Mediates Nematode Resistance in Soybean," Science, Nov. 30, 2012; 1206-9, 338(6111); doi: 1 0.1126/science.I228746. Epub Oct. 2, 2012.
Kim, Myungsik, et al., "Fine Mapping of the SCN Resistance Locus rhg1-b from PI 88788," The Plant Genome, 2010,81-89, 3(2).
Lee, Tong Geon, et al., "Copy Number Polymorphism in the SCN Resistance Lodus rhgl-b From PI 88788," Molecular & Cellular Biology of the Soybean Conference, Aug. 12-15, 2012, Abstract.
Prachi D. Matsye et al., The expression of a naturally occurring, truncated allele of an α-SNAP gene suppresses plant parasitic nematode infection, Plant Mol. Biol. 2012, pp. 131-155, vol. 80
Sara Melito et al., A nematode demographics assay in transgenic roots reveals no significant impacts of the Rhg1 locus LRR-Kinase on soybean cyst nematode resistance, BMC Plant Biology, 2010, pp. 104, vol. 10.
Ali Srour et al., The receptor like kinase at Rhg1-a/Rfs2 caused pleiotropic resistance to sudden death syndrome and soybean cyst nematode as a transgene by altering signaling responses, BMC Genomics, 2012, pp. 368, vol. 13.

(Continued)

*Primary Examiner* — Amjad Abraham
*Assistant Examiner* — Bratislav Stankovic

(57) ABSTRACT

Various compositions and methods are provided for identifying and selecting plants with enhanced resistance to soybean cyst nematode (SCN). Further provided are transgenic plants, plant parts, and seed and methods of their use comprising a heterologous polynucleotide operably linked to a promoter active in the plant are provided, as are methods of making such plants and methods of use, wherein said heterologous polynucleotide comprises at least one, or any combination thereof, of Glyma18g2580, Glyma18g2590, Glyma18g2600, Glyma18g2610; and Glyma18g2570 or an active variant or fragment thereof. Expression of the heterologous polynucleotide enhances the resistance of the plant to cyst nematode.

9 Claims, 8 Drawing Sheets

(56) References Cited

OTHER PUBLICATIONS

Figure 1:
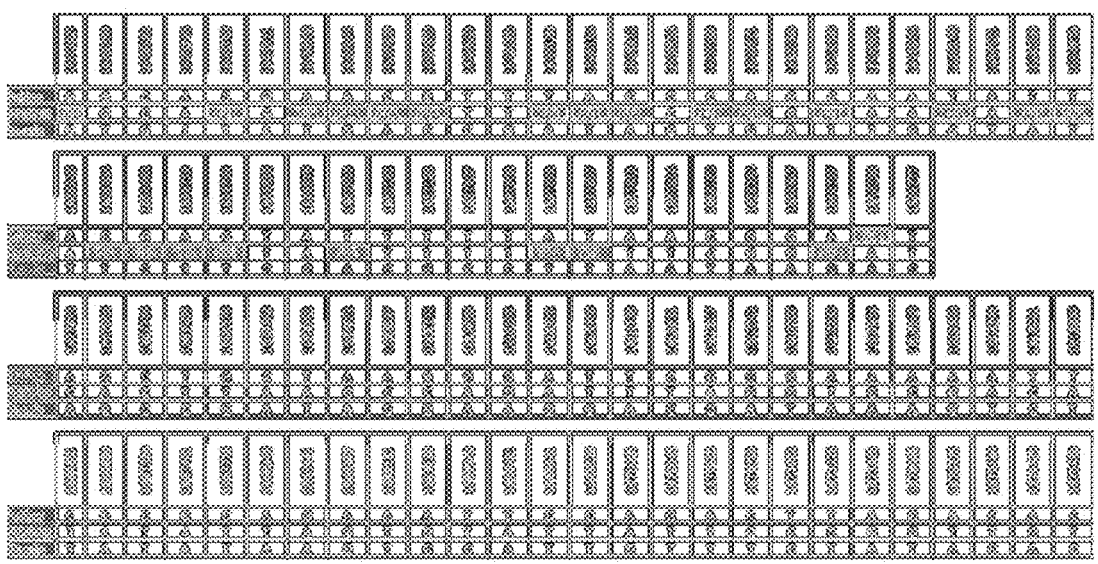

International Search Report—PCT/US2013/045340.
Written Opinion of the International Searching Authority—PCT/US2013/045340.
U.S. Appl. No. 61/646,017, filed May 11, 2012.
U.S. Appl. No. 61/676,854, filed Jul. 27, 2012.
Ahmed J. Afzal, PhD Thesis, Structure-Function Analysis of a Candidate Receptor Like Kinase Protein in Soybean Cyst Nematode Resistance and Identification of Accessory Proteins Involved in Plant Defense, Southern Illinois University, Carbondale, 2007, pp. 1-190.
David E. Cook et al., Copy Number Variation of Multiple Genes at RHG1 Mediates Nematode Resistance in Soybean, Science, Nov. 30, 2012, pp. 1206-1209, vol. 338.
Batley and Edwards, In: Association Mapping in Plants, 2007, pp. 95-102.
Genbank Accession No. JX907806, Dec. 20, 2012.
Genbank Accession No. NM_001255130, Feb. 24, 2014.
Richard W. Smiley et al., Pacific Northwest Extension Publication, Cereal Cyst Nematodes, PNW620, Oct. 2010, pp. 1-9.
James P. Thomas, Detection and identification: how are they related?, J. Optical Society of America, pp. 1457-1467, vol. 2, No. 9.
Pin Yue et al., Genetic analysis of resistance to soybean cyst nematode in PI 438489B, Euphytica, 2000, pp. 181-186, vol. 116.
U.S. Appl. No. 12/961,684, filed Apr. 7, 2011, David M. Webb.
U.S. Appl. No. 13/544,470, filed Nov. 1, 2012, David M. Webb.
U.S. Appl. No. 13/780,390, filed Feb. 28, 2013, Shendelman et al.
U.S. Appl. No. 13/781,963, filed Mar. 1, 2013, Shendelman et al.
U.S. Appl. No. 13/786,948, filed Mar. 6, 2013, Allen et al.
Anand, S.C., "Identification of Additional Soybean Germplasm with Resistant to Race 3 of the Soybean Cyst Nematode," *Plant. Disease*, 1984, vol. 68(7), pp. 593-595.
Anand, S.C., "Sources of resistance to the soybean cyst nematode," In Lamberti F., Taylor CE (eds) Cyst nematodes. NATO advanced study institute series. Plenum Press, New York, pp. 269-276.
Anand, S.C., "Genetic Diversity for Resistance to *Heterodera glycines* Race 5 in Soybean," *J. Nematol*, 1994, vol. 26(1), pp. 76-79.
Anand, S.C., et al., "Genetic Analyses of Soybean Genotypes Resistant to Soybean Cyst Nematode Race 5," *Crop. Sci*., 1989, vol. 29, pp. 1181-1184.
Anand, S.C, et al., "Variation in Parasistic Potential of *Heterodera Glycines* Populations," *Crop. Sci*., 1994, vol. 34, pp. 1452-1454.
Arondel, V., et al., "Map-Based Cloning of a Gene Controlling Omega-3 Fatty Acid Desaturation in *Arabidopsis*," *Science*, 1992, vol. 258, pp. 1353-1355.
Baltazar, B.M., et al., "Identification of restriction fragment length polymorphisms (RFLPs) to map soybean cyst nematode resistance genes in soybean," *Soybean Genet. Newsletter*, 1992, vol. 19, pp. 120-122.
Box, G.E.P., and Draper, N.R., "Adequacy of Estimation and the Use of Transformation," *Response Surfaces, Mixtures, and Ridge Analyses*, 2007, pp. 271-302, John Wiley & Sons, Inc.
Caldwell, B.E., et al., "Inheritance of Resistance of Soybeans to the Cyst Nematode, *Heterodera Glycines*," *Agronomy Journal*, 1960, vol. 52, pp. 635-636.
Concibido, V.C., et al., "A Decade of QTL Mapping for Cyst Nematode Resistance in Soybean," Crop Science, 2004, vol. 44, pp. 1121-1131.
Gibson, S., et al., "Isolating plant genes," *Trends Biotech*, 1993, vol. 11(7), pp. 306-313.
Golden, A.M., et al., "Terminology and Identity of Infraspecific Forms of the Soybean Cyst Nematode (Heterodera Glycines)," *Plant Disease Reporter*, 1970, vol. 54(7), pp. 544-546.
Hartwig, E.E., et al., "Breeding Pruductive Soybeans with Resistance to the Soybean Cyst Nematode," In: Shibles R. (ed) Proceedings World Soy Res Conf. III, Westview Press, Boulder, Colo., pp. 394-399.
Keim, P., et al., "RFLP Analysis of Soybean Breeding Populations: I. Genetic Structure Differences due to Inbreeding Methods," *Crop Science*, 1994, vol. 34, pp. 55-61.
Keim, P., et al., "A rapid protocol for isolating soybean DNA," *Soybean Genet. Newsletter*, 1988, vol. 15, pp. 150-152.
Keim, P., et al, "Construction of a random recombinant DNA library that is primarily single copy sequences," *Soybean Genet. Newsletter*, 1988, vol. 15, pp. 147-148.
Keim, P., et al., "Restriction fragment length polymorphism diversity in soybean," *Theor. Appl. Genet*., 1989, Vol. 77, pp. 786-792.
Knapp, S.J., et al., "Mapping quantitative trait loci using nonsimultaneous and simultaneous estimators and hypothesis tests," *Plant Genomes: Methods for Genetic and Physical Mapping*, 1992, pp. 209-237, Kluwer Academic Publishers, The Netherlands.
Lande, R., et al., "Efficiency of Marker Assisted Selection in the Improvement of Quantitative Traits," *Genetics*, 1990, vol. 124, pp. 743-756.
Lander, E.S., et al., "Strategies for studying heterogeneous genetic traits in humans by using a linkage map of restriction fragment length polymorphisms," *Prac. Natl. Acad. Sci. USA*, 1986, vol. 83, pp. 7353-7357.
Lander, E.S., et al., "Mapping Mendelian Factors Underlying Quantitative Traits Using RFLP Linkage Maps," *Genetics*, 1989, vol. 121, pp. 185-199.
Landry, B.S., and Hubert, N., "A genetic map for *Brassica napus* based on restriction fragment length polymorphisms detected with expressed DNA sequences," *Genome*, 1991, vol. 34, pp. 543-552.
Lewers, K., et al., "A physical map of a gene-dense region in soybean linkage group A2 near the black seed coat and $Rhg_4$ loci," *Theor. Appl. Genet*., 2002, vol. 104, pp. 254-260.
Lincoln, S.E., et al., "MAPMAKER/EXP," Whitehead Institute of Biomedical Research, Cambridge, Mass., (1993).
Lincoln, S.E., et al., "MAPMAKER/QTL," Whitehead Institute of Biomedical Research, Cambridge, Mass., (1990).
Liu, S., et al., "A soybean cyst nematode resistance gene points to a new mechanism of plant resistance to pathogens," *Nature*, 2012, vol. 492, pp. 256-263.
Mansur, L.M., et al., "Generation Mean Analysis of Resistance to Race 3 of Soybean Cyst Nematode," *Crop Sci*., 1993, vol. 33, pp. 1249-1253.
Marek, L.F., "Construction and Size Characterization of a Bacterial Artificial Chromosome (BAC) Library from Soybean," *Soybean Genet. Newsletter*, 1996, vol. 23, pp. 126-129.
Martin, G.B., et al., "Map-Based Cloning of a Protein Kinase Gene Conferring Disease Resistance in Tomato," *Science*, 1993, vol. 262, pp. 1432-1436.
McCann, J., et al., "Selection and Reproduction of Soybean Cyst Nematodes on Resistant Soybeans," *Crop Science*, 1982, vol. 22, pp. 78-80.
Mulrooney, R.P., "Soybean Disease Loss Estimate for Southern United States in 1987," *Plant Dis*., 1988, vol. 72, p. 915.
Murray, M., and Thompson, W.F., "Rapid isolation of high molecular weight plant DNA," *Nucleic Acids Research*, 1980, vol. 8(19), pp. 4321-4325.
Myers, G.O., and Anand, S.C., "Inheritance of resistance and genetic relationships among soybean plant introductions to races of soybean cyst nematode," *Euphytica*, 1991, vol. 55, pp. 197-201.
Nelson, R.L., et al., "Evaluation of the USDA Soybean Germplasm Collection: Maturity Groups 000 to IV (PI 427.136 to PI 445.845)," *USDA-ARS Technical Bulletin*, 1988, No. 1726.
Niblack, T.L., et al., "Soybean Yield Losses Due to *Heterodera glycines* in Iowa," *Plant Dis*., 1992, vol. 76(9), pp. 943-948.
Parrish, J.E., and Nelson, D.L., "Methods for Finding Genes a Major Rate-Limiting Step in Positional Cloning," *GATA*, 1993, vol. 10(2), pp. 29-41.
Rao-Arelli, A.P., and Anand, S.C., "Genetic Relationships Among Soybean Plant Introductions for Resistance to Race 3 of Soybean Cyst Nematode," *Crop Sci*., 1988, vol. 28, pp. 650-652.
Rao-Arelli, A.P., et al., "Additional dominant gene in PI 88.788 conferring resistance to soybean cyst nematode race 3," *Soybean Genet. Newsletter*, 1991, vol. 18, pp. 221-224.

(56) References Cited

OTHER PUBLICATIONS

Rao-Arelli, A.P., et al., "Soybean Resistance to Soybean Cyst Nematode Race 3 is Conditioned by an Additional Dominant Gene," *Crop Science*, 1992, vol. 32, pp. 862-864.

Rao-Arelli, A.P., and Clark, K.M., "Inheritance of Soybean Cyst Nematode Resistance Genes in Soybean Germplasm," *Agronomy Abstraces*, ASA, Madison, Wis, p. 100, Abstract.

Rao-Arelli, A.P., et al., "A Rapid Method for Inoculating Soybean Seedlings with *Heterodera glycines*," *Plant Disease*, 1991, vol. 75, pp. 594-595.

Rao-Arelli, A.P., et al., "Genetic Diversity Among Isolates of *Heterodera glycines* and Sources of Resistance in Soybeans," *Plant Disease*, 1992, vol. 76(9), pp. 894-896.

Riggs, R.D., and Schmitt, D.P., "Complete Characterization of the Race Scheme for *Heterodera glycines*," *Journal of Nematologists*, 1988, vol. 20(3), pp. 392-395.

Rommens, J.M., et al., "Identification of the Cystic Fibrosis Gene: Chromosome Walking and Jumping," *Science*, 1989, vol. 245, pp. 1059-1065.

Shoemaker, R.C., and Specht, J.E., "Integration of the Soybean Molecular and Classical Genetic Linkage Groups," *Crop Sci.*, 1995, vol. 35, pp. 436-446.

Tachibana, H., et al., "Registration of 'BSR101' Soybean," *Crop Science*, 1987, vol. 27, p. 612, Abstract.

Triantaphyllou, A., "Genetic Structure of Races of *Heterodera glycines* and Inheritance of Ability to Reproduce on Resistant Soybeans," *Journal of Nematology*, 1975, vol. 7(4), pp. 356-364.

Webb, D.M., et al., "Genetic mapping of soybean cyst nematode race-3 resistance loci in the soybean PI 437.654," *Theor. Appl. Genet.*, 1995, vol. 91, pp. 574-581.

Weisemann, J.M., et al., "Molecular markers located proximal to the soybean cyst nematode resistance gene, Rhg4," *Theor. Appl. Genet.*, 1992, vol. 85, pp. 136-138.

Weiss, M.G., "Genetic Linkage in Soybeans: Linkage Group VII," *Crop Science*, 1970, vol. 10, pp. 627-629.

Wicking, C., et al., "From linked marker to gene," *Trends Genet.*, 1991, vol. 7(9), pp. 288-289.

Winstead, N.N., et al., "Soybean Cyst Nematode in North Carolina," *Plant Dis. Rep.*, 1955, vol. 39(1), pp. 9-11.

Young, L.D., "Reproduction of Differentially Selected Soybean Cyst Nematode Populations on Soybeans," *Crop Science*, 1982, vol. 22, pp. 385-388.

Young, L.D., "Changes in the Reproduction of *Heterodera glycines* on Different Lines of *Glycine max*," *Journal of Nematology*, 1984, vol. 16(3), pp. 304-309.

Zhang, H-B., et al, "Map-based cloning in crop plants: tomato as a model system II. Isolation and characterization of a set of overlapping yeast artificial chromosomes encompassing the jointless locus," *Mol. Gen. Genet.*, 1994, vol. 244, pp. 613-621.

Zhu, et al., "Characterization and application of soybean YACs to molecular cytogenetics," *Mol. Gen. Genet.*, 1996, vol. 252, pp. 483-488.

U.S. Appl. No. 13/779,957, filed Feb. 28, 2013.
U.S. Appl. No. 15/146,130, filed May 4, 2016.
U.S. Appl. No. 15/146,147, filed May 4, 2016.
U.S. Appl. No. 15/146,168, filed May 4, 2016.

\* cited by examiner

Figure 3
Peking
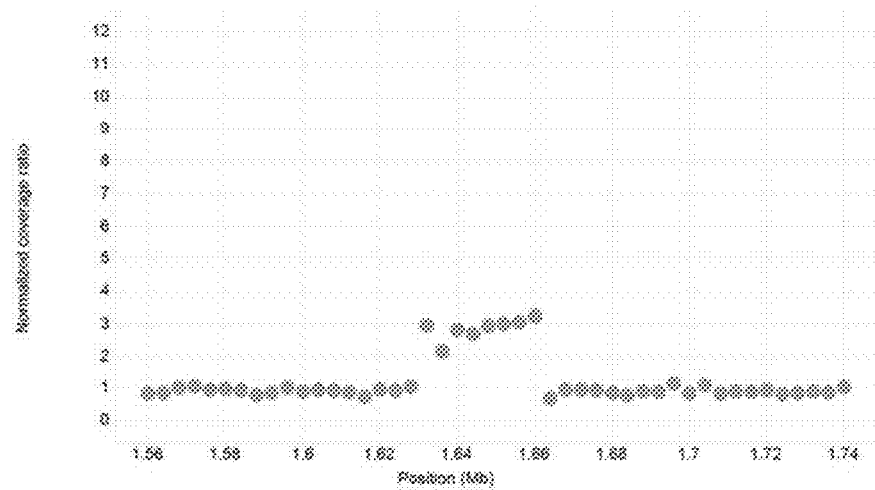
PI88788
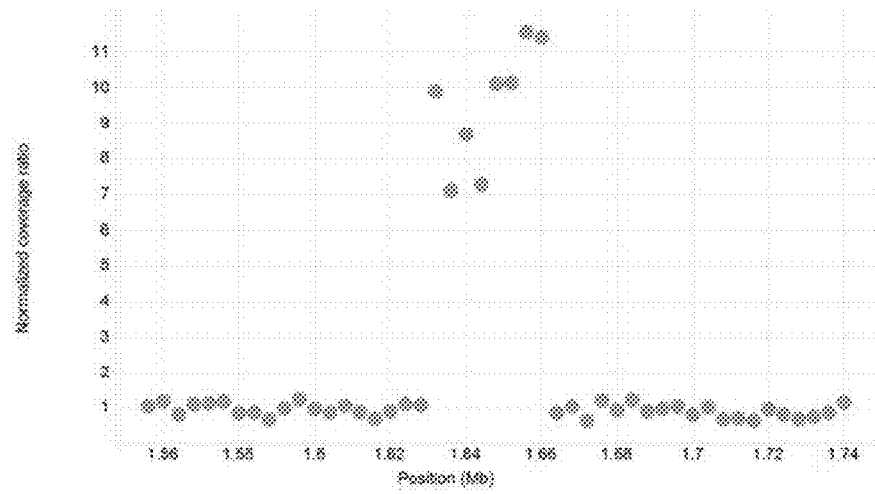

Figure 5

```
>Gm18 |BACK|    [Linkage_Group=G , Length=62308140 , DOE/JGI Glyma1.01]
        Length = 62308140
 Score =  184 bits (93), Expect = 3e-45
 Identities = 93/93 (100%)
 Strand = Plus / Plus Query: 1         gcagttttagtggaaaggcccaaccaatattctcaacattttgggccttcctcgaacaag    60
                 ||||||||||||||||||||||||||||||||||||||||||||||||||||||||||||
Sbjct: 1663356   gcagttttagtggaaaggcccaaccaatattctcaacattttgggccttcctcgaacaag    1663415

Query: 61        gacccgtaagaatagaagtttctaaaatggact    93
                 |||||||||||||||||||||||||||||||||
Sbjct: 1663416   gacccgtaagaatagaagtttctaaaatggact    1663448
 Score =  135 bits (68), Expect = 3e-30
 Identities = 68/68 (100%)
 Strand = Plus / Plus Query: 91        actgataatcaaatagttattgagatttttaattgagctgcatttgttaagaagtcacgg    150
                 ||||||||||||||||||||||||||||||||||||||||||||||||||||||||||||
Sbjct: 1632228   actgataatcaaatagttattgagatttttaattgagctgcatttgttaagaagtcacgg    1632287

Query: 151       ctaaaaga    158
                 ||||||||
Sbjct: 1632288   ctaaaaga    1632295
```

Figure 7

```
Score =  424 bits (214),  Expect = e-116
 Identities = 220/222 (99%)
 Strand = Plus / Plus Query:  355       caagtttggaccaatttatttctactgcctatattactttgttattgtgttggtatattt  414
                  |||||||||||||||||||||| |||||||||||||||||||||||||||||||||||||
Sbjct:  1663227   caagtttggaccaatttatttctgctgcctatattactttgttattgtgttggtatattt  1663286

Query:  415       tcttcatcaaagaatatccatttgtgctttaaattttgggtagttttgtttcttgctcca  474
                  |||||||||| |||||||||||||||||||||||||||||||||||||||||||||||||
Sbjct:  1663287   tcttcatcaaaaaatatccatttgtgctttaaattttgggtagttttgtttcttgctcca  1663346

Query:  475       caaattttgcagttttagtggaaaggccaaccaatattctcaacattttgggccttcc   534
                  ||||||||||||||||||||||||||||||||||||||||||||||||||||||||||
Sbjct:  1663347   caaattttgcagttttagtggaaaggccaaccaatattctcaacattttgggccttcc   1663406

Query:  535       tcgaacaaggacccgtaagaatagaagtttctaaaatggact  576
                  ||||||||||||||||||||||||||||||||||||||||||
Sbjct:  1663407   tcgaacaaggacccgtaagaatagaagtttctaaaatggact  1663448

Score =  254 bits (128),  Expect = 2e-65
 Identities = 140/146 (95%)
 Strand = Plus / Plus Query:  574       actgataatcaaatagttattgagattttaattgagctgcatttgttaagaagtcacgg  633
                  |||||||||||||||||||||||||||||||||||||||||||||||||||||||||||
Sbjct:  1632228   actgataatcaaatagttattgagattttaattgagctgcatttgttaagaagtcacgg  1632287

Query:  634       ctaanagagttacctagttgtcagttatactattttcatgactaagcagcaagcacagat  693
                  ||||  |||||||||||||||||||||||||||||||||||||||||||||||||||||
Sbjct:  1632288   ctaaaagagttacctagttgtcagttatactattttcatgactaagcagcaagcacagat  1632347
```

Figure 8

Breakpoint Primers

| Primer Name | Forward Primer | Reverse Primer |
|---|---|---|
| Rhg1_Left_break | TAATTTTGTCAGGCTATGGAATCA (SEQ ID NO:10) | TGGGTCATAAAACAACAACAGC (SEQ ID NO: 11) |
| Rhg1_Right_break | AACACAATCCGTGGTGTTGTAA (SEQ ID NO:12) | TTGAACAAGTCATTAGCAAGTAGCA (SEQ ID NO:13) |
| Rhg1_Junction | TGGAACTGCATTAGCATCCTT (SEQ ID NO:14) | TCTACCTCTCCACCAGCATGA (SEQ ID NO:15) |
| Rhg1_Seq* | GGATTAGGTTGATTGTTAGACAGCA (SEQ ID NO:16) | TGGAGAATATGCTCTCGGTTGT (SEQ ID NO:17) |

*Rhg1_Seq was modified with M13 sequencing tags to produce amplicons for Sanger Sequencing qPCR Primers

| Primer Name | Forward Primer | Reverse Primer | Copy # Region |
|---|---|---|---|
| Rhg1_copy1 | ATTTGCTGAAACACTGCGAAC (SEQ ID NO:26) | TCCGCGATCTCCAATGTC (SEQ ID NO:27) | Single Copy |
| Rhg1_copy3 | GGACCTTGGGTGTGGAAAA (SEQ ID NO:28) | CAAGTATCCGCGATCTCCAA (SEQ ID NO:29) | Single Copy |
| Rhg1_copy4 | GCTGAAACACTGCGAACGA (SEQ ID NO:30) | ACAAGTATCCGCGATCTCCAA (SEQ ID NO:31) | Single Copy |
| Rhg1_copy6 | AGATGGGTGGAGCTCAAGAAC (SEQ ID NO:32) | TCTACCTCTCCACCAGCATGA (SEQ ID NO:33) | Copy Variable |
| Rhg1_copy8 | AGGAGAATACAAGCAGCACCA (SEQ ID NO:34) | GGTTCAGCAGTTGGTTCCTT (SEQ ID NO:35) | Copy Variable |
| Rhg1_copy9 | CCCGATCCTTACATTTCCATT (SEQ ID NO:36) | CGGGTTTTCAGTCAGATTCATT (SEQ ID NO:37) | Copy Variable |
| Rhg1_copy10 | TCCCGATCCTTACATTTCCA (SEQ ID NO:38) | GTTTTGCCGGGTTTTCAGT (SEQ ID NO:39) | Copy Variable |
| Rhg1_copy12 | AACACCGTCACCACTCACC (SEQ ID NO:40) | TCAAATCAGAACCGTATCATCAA (SEQ ID NO:41) | Copy Variable |
| Rhg1_copy13 | TTTCGGTTGATGATGGGATT (SEQ ID NO:42) | GAGTTGCTGAAATATCCATAGATGC (SEQ ID NO:43) | Copy Variable |
| Rhg1_copy14 | AAGTACTCAGGTGGCGGTTC (SEQ ID NO:44) | ATGCTGTCCAATTAACTCACTGAT (SEQ ID NO:45) | Single Copy |
| Rhg1_copy15 | GCATGGTAACAGGGTGGAGT (SEQ ID NO:46) | GCAACATCCATTTTAACACACC (SEQ ID NO:47) | Single Copy |
| Rhg1_copy17 | TACTCAGGTGGCGGTTCG (SEQ ID NO:48) | GGTCCCATAATAAATGCTGTCC (SEQ ID NO:49) | Single Copy |

US 9,988,693 B2

1

GENETIC LOCI ASSOCIATED WITH RESISTANCE OF SOYBEAN TO CYST NEMATODE AND METHODS OF USE

CROSS-REFERENCES TO RELATED APPLICATIONS

This application is a Divisional of U.S. application Ser. No. 13/779,957, filed on Feb. 28, 2013 and claims priority to U.S. Provisional Patent Application Ser. No. 61/740,526, filed on Dec. 21, 2012, U.S. Provisional Patent Application Ser. No. 61/671,937, filed Jul. 16, 2012 and U.S. Provisional Patent Application Ser. No. 61/660,387, filed Jun. 15, 2012, each of which is hereby incorporated herein in its entirety by reference.

FIELD OF THE INVENTION

The present disclosure relates to compositions and methods useful in creating or enhancing cyst nematode resistance in plants.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 20160427_5274USDIV_Sequence-Listing.txt, created on Apr. 27, 2016, and having a size of 21 KB and is filed concurrently with the specification. The sequence listing contained in this ASCII formatted document is part of the specification and is herein incorporated by reference in its entirety.

BACKGROUND OF THE INVENTION

Soybean Cyst Nematode (SCN) is a parasitic pest which has threatened soybean production in the U.S. for more than fifty years. SCN resistance is an economically important trait as infection can substantially reduce yields. Despite this, two primary sources of resistance contribute to elite Pioneer germplasm: Peking and PI88788. Several loci have been reported to confer SCN resistance, arguably the most important of these rhg1 maps to linkage group G and is comprised of at least two alleles: rhg1 derived from Peking and rhg1-b derived from PI88788.

Cloning of the rhg1 allele was reported previously, and a candidate receptor-like kinase gene is the subject of a competitor's patent applications; despite this, no genetic evidence has been provided to support these claims. Furthermore, a recent study fine-mapped the rhg1-b allele to a 67-kb region which does not include the rhg1 candidate gene. In light of these reports, the true molecular nature of rhg1 and rhg1-b SCN resistant alleles remains unclear of the same gene and it is uncertain whether rhg1 and rhg1-b are alleles of the same resistant gene or represent two distinct albeit tightly linked genetic loci.

Molecular characterization of these alleles would have important implications for soybean cultivar improvement.

SUMMARY

Compositions and methods for identifying and selecting plants with enhanced resistance to soybean cyst nematode (SCN) are provided.

Methods are provided for identifying and/or selecting a soybean plant or a soybean germplasm with enhanced resistance to soybean cyst nematode. In these methods, the presence of at least one marker allele is detected in the genome of the soybean plant or soybean germplasm; and, a soybean plant or soybean germplasm with enhanced resistance to cyst nematode is thereby identified and/or selected. The marker allele can include any marker allele that is associated with a duplication of a region within the rhg1 locus which confers enhanced tolerance to soybean cyst nematodes.

Further provided are methods of identifying and/or selecting a soybean plant or a soybean germplasm with enhanced resistance to soybean cyst nematode employing quantitative PCR or other quantitative technique of any sequence within the duplicated region of the rhg1 locus.

Methods are also provided for identifying and/or selecting a soybean plant or a soybean germplasm with enhanced resistance to cyst nematode by detecting an increased copy number of at least one of or any combination of Glyma18g2580 (SEQ ID NO: 3), Glyma18g2590 (SEQ ID NO: 2), Glyma18g2600 (SEQ ID NO:4), Glyma18g2610 (SEQ ID NO:5); and Glyma18g2570 (SEQ ID NO:1) or an active variant or fragment thereof.

Methods of identifying and/or selecting a soybean plant or a soybean germplasm with enhanced resistance to soybean cyst nematode are also provided which comprise detecting the DNA junction formed at the breakpoint of a duplication of nucleotide sequences within the rhg1 locus.

Kits for the various methods of identifying the soybean plants or soybean germplasm having the enhanced resistance to SCN are further provided.

Transgenic plants, plant parts, and seed comprising a heterologous polynucleotide operably linked to a promoter active in the plant are provided, as are methods of making such plants and methods of use, wherein said heterologous polynucleotide comprises at least one, or any combination thereof, of Glyma18g2580 (SEQ ID NO: 3), Glyma18g2590 (SEQ ID NO: 2), Glyma18g2600 (SEQ ID NO:4), Glyma18g2610 (SEQ ID NO:5); and Glyma18g2570 (SEQ ID NO:1) or an active variant or fragment thereof. Expression of the heterologous polynucleotide enhances the resistance of the plant to cyst nematode.

DETAILED DESCRIPTION OF DRAWINGS

FIG. 1 shows the heterozygosity within PI88788 derived rhg1 locus. Haplotypes were built from SNPs found during deep resequencing of Soy ancestors. Persistent heterozygosity inherited over generations at the rhg1 locus within resistant lines derived from PI88788 was observed.

Figure 2:
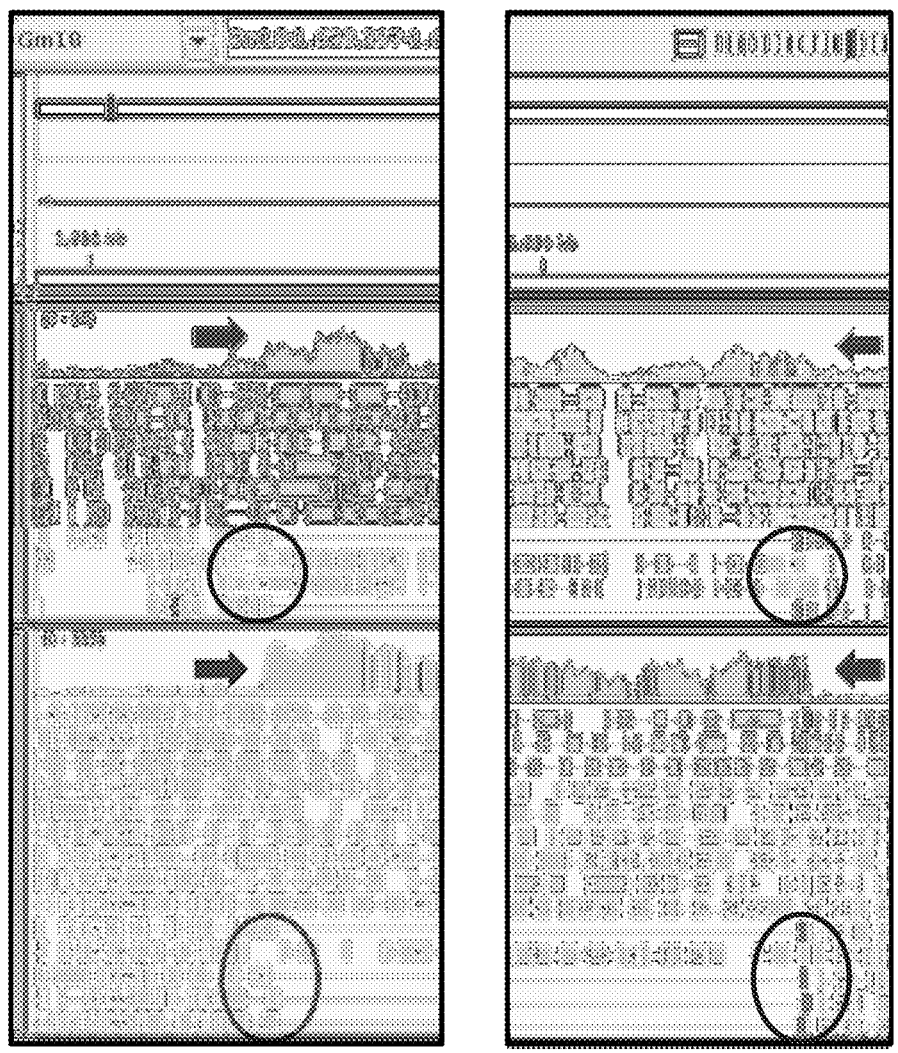

FIG. 2 shows the next-generation sequencing alignments that indicate tandem duplication. Read alignments are visualized as grey boxes in tracks with read-pairs connected by grey lines. Total sequencing coverage is visualized in the track above with polymorphic sites. Significant changes in coverage are observed at the putative duplication breakpoints (arrows). Discordantly mapped paired-end reads (circles) suggest tandem duplication of the interval Gm18: 1.632-1.663 (Mb).

FIG. 3 shows a copy-number analysis and indicates a substantial copy-number increase. Copy-number analysis was performed by calculating the sequencing coverage in a moving window across the rhg1 fine-map region. Coverage of Peking indicated an increased normalized coverage ratio in the region of Gm18:1.632-1.663 (Mb) of approximately 3-fold over susceptible. Coverage of PI88788 indicated an increased normalized coverage ratio of 9-fold in the same region.

Figure 4:
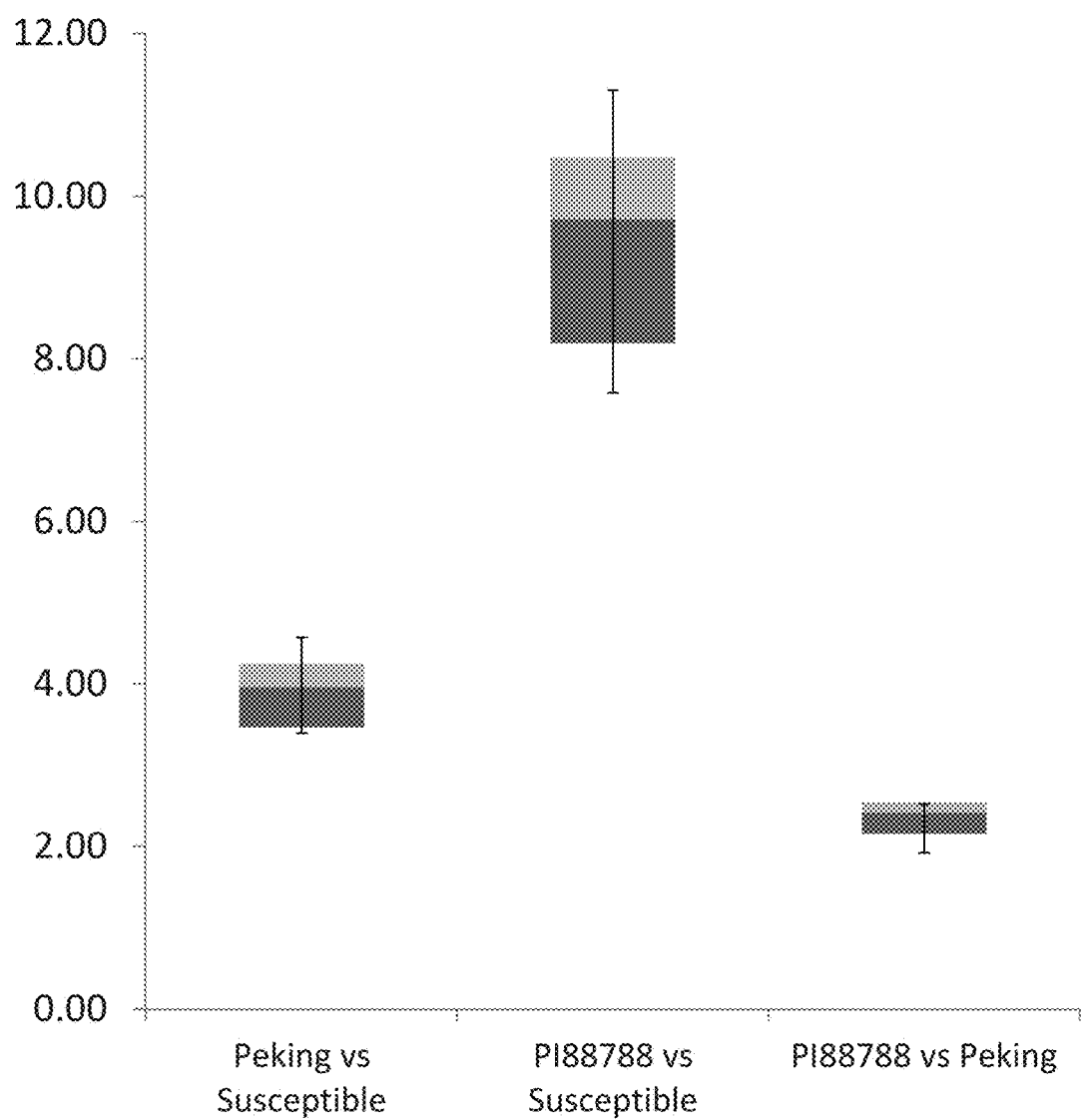

FIG. 4 shows the results of qPCR analysis which indicates an increased copy-number in Peking and PI88788. PCR primers were designed against the single-copy and variable-copy regions of the rhg1 fine-mapped locus. Two sources of Peking and PI88788 resistance and three susceptible lines were assayed in two replicates for all primer-pairs. Replicates were averaged and ΔΔCt analysis was performed pair-wise and averaged between every variable-copy and single-copy combination. The results are consistent with an ~4-fold and ~9-fold increased copy-number in Peking and PI88788 relative to susceptible lines.

FIG. 5 shows the BLAST® results of a contig spanning the duplication breakpoints. Discordantly mapped paired-end reads from the boundaries of the tandem duplication were assembled into contigs. Contigs were blasted against the Soybean Genomic Assembly Glyma1.01 (JGI). The alignment of this contig to the reference is consistent with a tandem duplication event with breakpoints at Gm18:1663448 and Gm18:1632228. Query A is set forth in SEQ ID NO: 18; Subject A is set forth in SEQ ID NO: 19; Query B is set forth in SEQ ID NO: 20; and subject B is set forth in SEQ ID NO:21.

Figure 6:
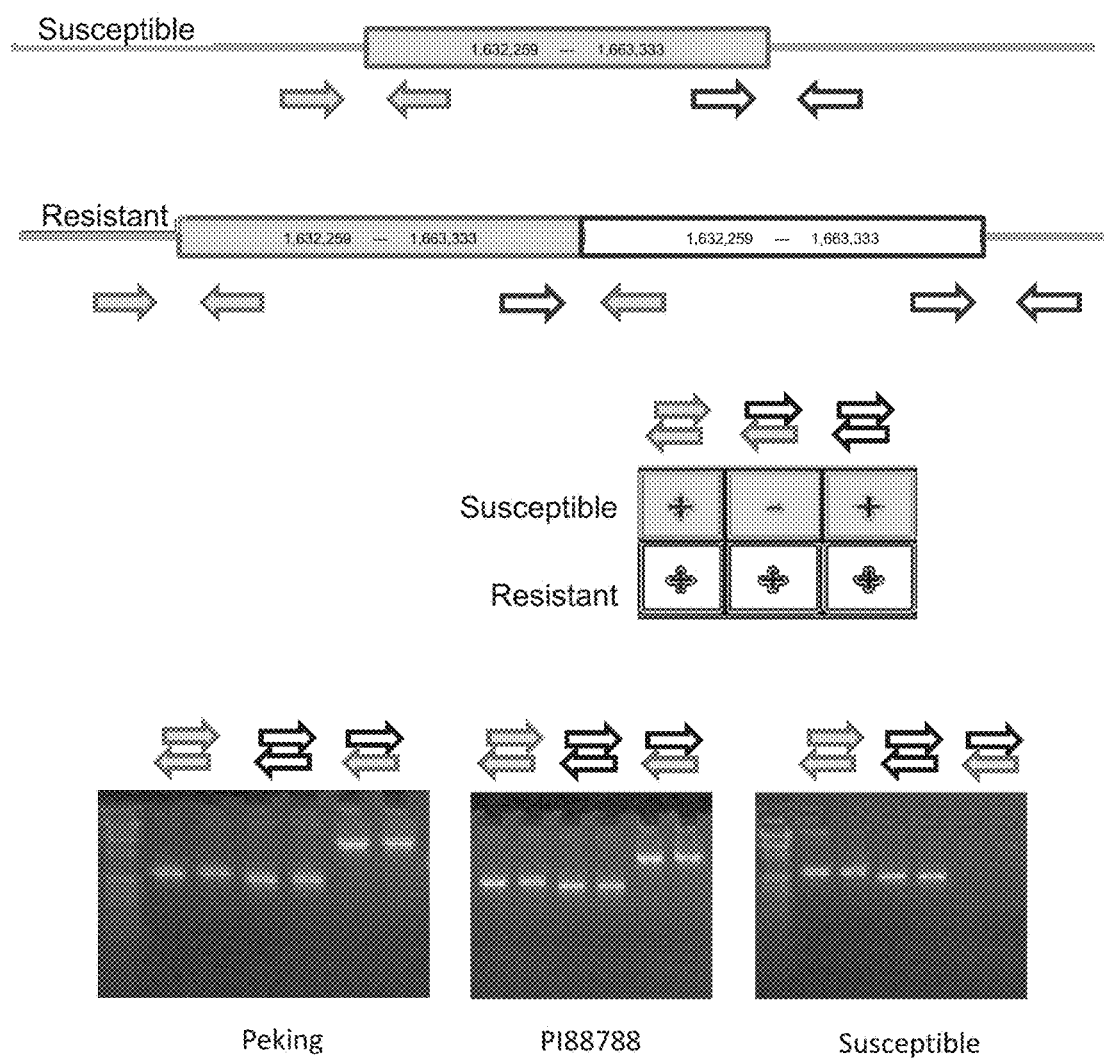

FIG. 6 shows PCR amplicons in Peking and PI88788 support the putative breakpoints. PCR primer-pairs were designed to amplify the ends of the copy-variable regions (dark (or black) pair, light (or gray) pair) and across the putative breakpoints (mixed pair). Primer-pairs designed to amplify the ends of the copy-variable region produce amplicons in all lines. Primer-pairs designed to amplify across the putative breakpoints produce amplicons in Peking and PI88788 but not susceptible.

FIG. 7 shows sequencing and alignment of PCR amplicons confirms the breakpoints. A primer pair spanning the breakpoint junction was ordered with the M13 sequencing tags, tested and sent off for Sanger Sequencing. The resulting amplicons from Peking and PI88788 were aligned to the Soybean Genomic Assembly Glyma1.01 (JGI) by BLAST®. The alignment of these amplicons to the reference is consistent with a tandem duplication event with breakpoints at Gm18:1663448 and Gm18:1632228, an example is depicted. Query A is set forth in SEQ ID NO: 22; subject A is set forth in SEQ ID NO: 23; query B is set forth in SEQ ID NO:24; and subject B is set forth in SEQ ID NO: 25.

FIG. 8 provides various primer sequences.

DETAILED DESCRIPTION

I. Definitions

Before describing the present invention in detail, it is to be understood that this invention is not limited to particular embodiments, which can, of course, vary. It is also to be understood that the terminology used herein is for the purpose of describing particular embodiments only, and is not intended to be limiting.

Certain definitions used in the specification and claims are provided below. In order to provide a clear and consistent understanding of the specification and claims, including the scope to be given such terms, the following definitions are provided.

As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include examples encompassed by the terms "consisting essentially of" and "consisting of." Similarly, the term "consisting essentially of" is intended to include examples encompassed by the term "consisting of."

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term "amplifying" in the context of nucleic acid amplification is any process whereby additional copies of a selected nucleic acid (or a transcribed form thereof) are produced. An "amplicon" is an amplified nucleic acid, e.g., a nucleic acid that is produced by amplifying a template nucleic acid by any available amplification method.

"Backcrossing" is a process in which a breeder crosses a progeny variety back to one of the parental genotypes one or more times.

The term "chromosome segment" designates a contiguous linear span of genomic DNA that resides in planta on a single chromosome. "Chromosome interval" refers to a chromosome segment defined by specific flanking marker loci.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic linkage relationships among loci on one or more chromosomes (or linkage groups) within a given species, generally depicted in a diagrammatic or tabular form.

"Genotype" refers to the genetic constitution of a cell or organism.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Introgression" means the entry or introduction of a gene, QTL, marker, haplotype, marker profile, trait, or trait locus from the genome of one plant into the genome of another plant.

The terms "label" and "detectable label" refer to a molecule capable of detection. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state non-radiatively transfers to the quencher where it either dissipates non-radiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, tolerance, etc.).

"Linkage" refers to a phenomenon wherein alleles on the same chromosome tend to segregate together more often than expected by chance if their transmission was independent. Genetic recombination occurs with an assumed random frequency over the entire genome. Genetic maps are constructed by measuring the frequency of recombination between pairs of traits or markers. The closer the traits or markers are to each other on the chromosome, the lower the frequency of recombination, and the greater the degree of linkage. Traits or markers are considered herein to be linked if they generally co-segregate. A $1/100$ probability of recombination per generation is defined as a map distance of 1.0 centiMorgan (1.0 cM). The genetic elements or genes located on a single chromosome segment are physically linked. Two loci can be located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 9, 8, 7, 6, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 9%, 8%, 7%, 6%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). Put another way, closely linked loci co-segregate at least about 90% of the time. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 4 Kb, about 3 Kb, about 2 Kb, about 1 Kb, about 500 nucleotides, about 250 nucleotides, or less.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

"Linkage disequilibrium" refers to a phenomenon wherein alleles tend to remain together in linkage groups when segregating from parents to offspring, with a greater frequency than expected from their individual frequencies.

"Linkage group" refers to traits or markers that generally co-segregate. A linkage group generally corresponds to a chromosomal region containing genetic material that encodes the traits or markers.

"Locus" is a defined segment of DNA.

A "map location" or "map position" or "relative map position" is an assigned location on a genetic map relative to linked genetic markers where a specified marker can be found within a given species. Map positions are generally provided in centimorgans. A "physical position" or "physical location" or "physical map location" is the position, typically in nucleotide bases, of a particular nucleotide, such as a SNP nucleotide, on a chromosome.

"Mapping" is the process of defining the linkage relationships of loci through the use of genetic markers, populations segregating for the markers, and standard genetic principles of recombination frequency.

"Marker" or "molecular marker" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of soybean markers have been mapped and linkage groups created, as described in Cregan, P. B., et al., "An Integrated Genetic Linkage Map of the Soybean Genome" (1999) Crop Science 39:1464-90, and more recently in Choi, et al., "A Soybean Transcript Map: Gene Distribution, Haplotype and Single-Nucleotide Polymorphism Analysis" (2007) Genetics 176:685-96. Many soybean markers are publicly available at the USDA affiliated soybase website. All markers are used to define a specific locus on the soybean genome. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in soybeans. "Marker assisted selection" refers to the process of selecting a desired trait or traits in a plant or plants by detecting one or more nucleic acids from the plant, where the nucleic acid is linked to the desired trait, and then selecting the plant or germplasm possessing those one or more nucleic acids.

"Haplotype" refers to a combination of particular alleles present within a particular plant's genome at two or more linked marker loci, for instance at two or more loci on a particular linkage group. For instance, in one example, two specific marker loci on LG-O are used to define a haplotype for a particular plant. In still further examples, 3, 4, 5, 6, 7, 8, 9, 10, 11, 12, 13, 14, 15, 16, 17, 18, 19, 20, or more linked marker loci are used to define a haplotype for a particular plant.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells, and the like. Grain is intended to mean the mature seed produced by commercial growers for purposes other than growing or reproducing the species.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid sequence," "nucleic acid fragment," and "oligonucleotide" are used interchangeably herein. These terms encompass nucleotide sequences and the like. A polynucleotide is a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide (synthetic or occurring naturally) that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Tolerance and "improved tolerance" are used interchangeably herein and refer to any type of increase in resistance or tolerance to, or any type of decrease in susceptibility. A "tolerant plant" or "tolerant plant variety" need not possess absolute or complete tolerance. Instead, a "tolerant plant," "tolerant plant variety," or a plant or plant variety with "improved tolerance" will have a level of resistance or tolerance which is higher than that of a comparable susceptible plant or variety.

"Self crossing" or "self pollination" or "selfing" is a process through which a breeder crosses a plant with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. Yield is the final culmination of all agronomic traits.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the invention or biologically active portion thereof is recombinantly produced, optimally culture medium represents less than about 30%, 20%, 10%, 5%, or 1% (by dry weight) of chemical precursors or non-protein-of-interest chemicals.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

II. Overview

Plants that have enhanced resistance to soybean cyst nematode (SCN) are known, however the reason for their resistance has been unknown until now. The present invention shows that duplications within the rhg1 locus, and subsequent increase in expression of the duplicated genes within the duplicated segment, causes the resistance within the soybean to this economically important soybean disease. More specifically, a tandem duplication within the rhg1 fine-mapped region has been identified and evidence is provided to suggest that rhg1 and rhg1-b harbor copy-number variable alleles of this structural variant. This copy-variation underlies the SCN resistance phenotype attributed to the rhg1 locus. These results have important implications for soybean product development and point to potential strategies for cultivar improvement. The various methods and compositions provided herein apply this new understanding of the rhg1- and rhg1-b alleles.

By "enhanced resistance" is intended that the plants show a decrease in the disease symptoms that are the outcome of plant-cyst nematode interactions. That is, the damage caused by cyst nematode is prevented, or alternatively, the disease symptoms caused by the cyst nematode is minimized or lessened. Thus, enhanced resistance to cyst nematode can result in the suppressing, controlling, and/or killing the invading cyst nematode. In specific embodiments, the enhanced resistance can reduce the disease symptoms resulting from pathogen challenge by at least about 2% to at least about 6%, at least about 5% to about 50%, at least about 10% to about 60%, at least about 30% to about 70%, at least about 40% to about 80%, or at least about 50% to about 90% or greater. Hence, the methods provided herein can be utilized to protect plants from disease, particularly those diseases that are caused by cyst nematodes. Assays that measure the control of a pest are known and include measuring over time, the average lesion diameter, the pathogen biomass, and the overall percentage of decayed plant tissues. See, for example, Thomma et al. (1998) Plant Biology 95:15107-15111 and U.S. Pat. No. 5,614,395, both of which are herein incorporated by reference.

A variety of cyst nematodes are known. Particular members of the cyst nematodes, include, but are not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). In specific embodiments, the methods and compositions disclosed herein are employed to enhance resistance to *Heterodera glycines* (soybean cyst nematode).

III. Region Conferring Enhanced Resistance to Cyst Nematodes

As used herein, the rhg1 locus comprises a region of the soybean genome which maps to linkage group G. See, for example, Kim et al. (2010) *The Plant Genome Journal* 32:81-89 which is herein incorporated by reference in its entirety. Two rhg1 alleles that confer resistance to a cyst nematode are known and include the rhg1 allele derived from Peking and the rhg1-b allele derived from PI88788. As described elsewhere herein, characterization of the rhg1 alleles conferring resistance to the cyst nematode comprises an increase in copy number of at least one region of the rhg1 locus.

In specific embodiments, an increase in copy number comprises a duplication of at least one region within the rhg1 locus. A "duplication" of at least one region within the rhg1 locus can comprise any increase in copy number of that region including 2, 3, 4, 5, 6, 7, 8, 9, 10, 11, 12, 13, 14, 15 or more copies. A region within the rhg1 locus can be of any length, including 20, 100, 200, 300, 400 nucleotides, 0.5, 1, 2, 3, 4, 5, 6, 7, 8, 9, 10, 15, 20, 25, 30, 40, 50, 60 KB or longer.

In specific embodiments, the duplicated region of the rhg1 locus is between about position GM18:1663448 and about position GM18:1632228 of the soybean genome. In still further embodiments, the duplication of the at least one region of the rhg1 locus comprises a tandem duplication of the region. As used herein, the term "tandem" refers to sequences being immediately adjacent to one another.

In one embodiment, the duplication of the region within the rhg1 locus comprises a tandem duplication of the soybean genome between about position GM18:1663448 and about position GM18:1632228. In further embodiments, the tandem duplications are found in the same orientation with respect to one another.

In other embodiments, the duplication of the region within the rhg1 locus comprises a duplication of at least one gene or regulatory region within the locus or it can comprise a duplication of at least one gene or regulatory region located between about position GM18:1663448 and about position GM18:1632228 of the soybean genome. The genes within these regions can encode polypeptides or RNA regulatory elements. In specific embodiments, the duplication of the region within the rhg1 locus comprises an increase in copy of number of anyone or any combination of the following polynucleotides: Glyma18g2580 (SEQ ID NO: 3), Glyma18g2590 (SEQ ID NO: 2), Glyma18g2600 (SEQ ID NO:4), Glyma18g2610 (SEQ ID NO:5); and/or Glyma18g2570 (SEQ ID NO:1) or an active variant or fragment thereof.

IV. Methods of Identifying and Breeding Plants Having an Enhanced Resistance to Cyst Nematodes Various methods are provided to identify soybean plants with an enhanced resistance to cyst nematodes. In one embodiment, the method of identifying comprises detecting at least one marker allele associated with a duplication of at least one region within the rhg1 locus. The term "associated with" in connection with a relationship between a marker locus and a phenotype refers to a statistically significant dependence of marker frequency with respect to a quantitative scale or qualitative gradation of the phenotype. Thus, an allele of a marker is associated with a trait of interest when the allele of the marker locus and the trait phenotypes are found together in the progeny of an organism more often than if the marker genotypes and trait phenotypes segregated separately.

In one embodiment, the marker allele being detected is associated with (1) a duplication or a tandem duplication of the soybean genome between about position GM18:1663448 and about position GM18:1632228; (2) a duplicated region found between about position GM18:1663448 and about position GM18:1632228; or (4) a duplication of a gene between found between about position GM18:1663448 and about position GM18:1632228; wherein each of the duplications is associated with an enhanced resistance to cyst nematode.

In one non-limiting example, the marker allele associated with the duplication of at least one region within the rhg1 locus comprises the DNA junction formed at the breakpoint of a tandem duplication of a region within the rhg1 locus. Such DNA junction regions are described in more detail elsewhere herein.

Additional markers alleles that can be used are set forth in Tables 1 and 2. Table 1 provides a list of polymorphic sites found within the rhg1 locus. The chromosomal position is denoted in the first two columns. "Ref" denotes the nucleotide occurring in the reference soybean sample, and "ALT" denotes the nucleotide found in the soybean lines having enhanced resistance to SCN. The presence of the nucleotide alteration in the Peking and the P188788 lines is denoted in the last two columns. Table 2 provides a list of polymorphic sites found within the coding regions of the rhg1 locus, specifically polymorphisms in Glyma18g2580 (SEQ ID NO: 3), Glyma18g2590 (SEQ ID NO: 2), Glyma18g2600 (SEQ ID NO:4), Glyma18g2610 (SEQ ID NO:5); and Glyma18g2570 (SEQ ID NO:1) are provided. Thus, any one marker or any combination of the polymorphisms set forth in Tables 1 and 2 can be used to aid in identifying and selecting soybean plants with enhanced resistance to SCN.

Further provided are methods for identifying a soybean plant or a soybean germplasm with enhanced resistance to cyst nematode. The method comprises detecting a duplication of a region within the rhg1 locus within the genome of the soybean plant or germplasm. In such a method, the duplication of a region within the rhg1 locus can comprise a tandem duplication of the region of the soybean genome between about position GM18:1663448 and about position GM18:1632228. In other embodiments, the duplication of the region within the rhg1 locus comprises a duplication of any region between position GM18:1663448 and GM18:1632228, including, for example, at least one of or any combination of Glyma18g2580 (SEQ ID NO: 3), Glyma18g2590 (SEQ ID NO: 2), Glyma18g2600 (SEQ ID NO:4), Glyma18g2610 (SEQ ID NO:5); and Glyma18g2570 (SEQ ID NO:1) or active variants and fragments thereof. Such methods of detection include quantitative PCR or other quantitative techniques, which are described in further detail elsewhere herein.

Additional methods for identifying a soybean plant or a soybean germplasm with enhanced resistance to cyst nematode include detecting an increased copy number of any duplicated region within the rhg1 locus, or between genomic position GM18:1663448 and GM18:1632228, or detecting an increased copy number of any one or any combination of the following polynucleotides Glyma18g2580 (SEQ ID NO: 3), Glyma18g2590 (SEQ ID NO: 2), Glyma18g2600 (SEQ ID NO:4), Glyma18g2610 (SEQ ID NO:5); and Glyma18g2570 (SEQ ID NO:1), or an active variant or fragment thereof. Methods by which copy number can be assayed are described elsewhere herein, and include, for example, PCR amplification and DNA sequence or the copy number analysis as shown in the examples herein. An increase in copy number includes at least 2, 3, 4, 5, 6, 7, 8, 9, 10 or more copies of a given region.

Further provided are methods for identifying a soybean plant or a soybean germplasm with enhanced resistance to cyst nematodes by detecting the DNA junction formed at the breakpoint of a duplication of a region within the rhg1 locus. A "junction" is a point where two specific DNA fragments join. As used herein, a "DNA junction" refers to DNA that comprises a junction point. For example, a junction exists where the duplicated region of the rhg1 locus joins the flanking genomic DNA. Thus, as used herein, a "DNA junction formed at the breakpoint of a duplication of a region" comprises the nucleotide sequence appearing at the junction where the two regions of DNA are repeated. In specific embodiments, the duplications are repeated in tandem. In one embodiment, the DNA junction comprises a DNA sequence that arises when the region of the soybean genome between about position GM18:1663448 and about position GM18:1632228 are placed in tandem and in the same orientation with itself. The DNA junction can be of any length including, but not limited to, 10 nt, 20 nt, 30 nt, 40 nt, 50 nt, 75 nt, 100 nt, 150 nt, 200 nt, 250 nt, 300 nt, 400 nt, 500 nt, 600 nt, 700 nt or more. The length of the DNA junction should be of sufficient length to allow for the detection of the junction and, depending on the need and detection technique being employed, to allow for a sufficient level of specificity of detection.

In specific embodiments, the DNA junction formed at the breakpoint of the tandem duplication of a region within the rhg1 locus comprises the sequence set forth in any one of SEQ ID NOS: 6, 7, 8 or 9 or a fragment thereof. In specific embodiments, the DNA junction being detected comprises a fragment of any one of SEQ ID NO: 6, 7, 8 or 9 having at least 10 nt, 20 nt, 30 nt, 40 nt, 50 nt, 75 nt, 100 nt, 150 nt, 200 nt, 250 nt, 300 nt or more consecutive nucleotides in length.

Various methods can be used to detect the novel DNA junction including, but not limited to, PCR amplification, hybridization methods or DNA sequencing. Such methods are discussed elsewhere herein.

In one embodiment, detecting a DNA junction comprises contacting a plant material with a first and a second primer; and, amplifying a polynucleotide comprising a DNA junction formed at the breakpoint of a duplication of a region of the rhg1 locus. In more specific embodiments, the first and second primer amplify a polynucleotide comprising a DNA junction comprising a DNA sequence that arises when the region of the soybean genome between about position GM18:1663448 and about position GM18:1632228 are placed in tandem and in the same orientation with itself. In specific embodiments, the primer pair amplifies the DNA junction set forth in any one of SEQ ID NOS: 6, 7, 8, or 9 or a fragment thereof.

As used herein, "plant material" refers to material which is obtained or derived from a plant or plant part. In specific embodiments, the biological sample comprises a soybean tissue.

The polynucleotide probes and primers employed in the various methods and kits disclosed herein specifically detect a target DNA sequence. Any conventional nucleic acid hybridization or amplification method can be used to identify the presence of the desired junction DNA. By "specifically detect" is intended that the polynucleotide can be used either as a primer to amplify the desired DNA sequence or the polynucleotide can be used as a probe that hybridizes under stringent conditions to a polynucleotide having the desired DNA sequence. The level or degree of hybridization which allows for the specific detection of the desired DNA sequence is sufficient to distinguish the polynucleotide with the desired DNA sequence from a polynucleotide lacking this region and thereby allow for discriminately identifying a plant having the desired DNA sequence.

By "shares sufficient sequence identity or complentarity to allow for the amplification of a desired DNA sequence" is intended the sequence shares at least 80%, 85%, 90%, 91%, 92%, 93%, 94%, 95%, 96%, 97%, 98%, 99% or 100% identity or complementarity to a fragment or across the full length of the polynucleotide having the desired DNA sequence.

Regarding the amplification of a target polynucleotide (e.g., by PCR) using a particular amplification primer pair, "stringent conditions" are conditions that permit the primer pair to hybridize to the target polynucleotide to which a primer having the corresponding wild-type sequence (or its complement) would bind and preferably to produce an identifiable amplification product (the amplicon) having a (1) a DNA junction comprising the breakpoint of a duplication of a region within the rhg1 locus; (2) DNA junction comprising a DNA sequence that arises when the region of the soybean genome between about position GM18:1663448 and about position GM18:1632228 are placed in tandem and in the same orientation with itself; (3) a DNA junction set forth in any one of SEQ ID NOS: 6, 7, 8, or 9 or a fragment thereof; or (4) any DNA sequence that is associated with a duplication within the rhg1 locus. In a PCR approach, oligonucleotide primers can be designed for use in PCR reactions to amplify the desired DNA junction. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Methods of amplification are further described in U.S. Pat. Nos. 4,683,195, 4,683,202 and Chen et al. (1994) PNAS 91:5695-5699. These methods as well as other methods known in the art of DNA amplification may be used in the practice of the embodiments of the present invention. It is understood that a number of parameters in a specific PCR protocol may need to be adjusted to specific laboratory conditions and may be slightly modified and yet allow for the collection of similar results.

The amplified polynucleotide (amplicon) can be of any length. For example, the amplicon can be about 10, 50, 100, 200, 300, 500, 700, 100, 2000, 3000, 4000, 5000 nucleotides in length or longer.

Any primer can be employed in the methods of the invention that allows a (1) a DNA junction comprising the breakpoint of a duplication of a region within the rhg1 locus; (2) a DNA junction comprising a DNA sequence that arises when the region of the soybean genome between about position GM18:1663448 and about position GM18:1632228 are placed in tandem and in the same orientation with itself; (3) a DNA junction set forth in any one of SEQ ID NOS: 6, 7, 8, or 9 or a fragment thereof; or (4) any DNA sequence that is associated with a duplication of the rhg1 locus to be amplified and/or detected. For example, in specific embodiments, the first primer comprises a fragment of a polynucleotide sequence flanking the 3' end of the DNA junction and the second primer comprises a fragment of a polynucleotide sequence flanking the 5' end of the DNA junction, wherein the first or the second primer shares sufficient sequence identity or complementarity to the polynucleotide to amplify desired DNA junction region. The primers can be of any length sufficient to amplify the desired region including, for example, at least 6, 7, 8, 9, 10, 15, 20, 15, or 30 or about 7-10, 10-15, 15-20, 20-25, 25-30, 30-35, 35-40, 40-45 nucleotides or longer. In one embodiment, the primer pair employed to amplify the junction comprises SEQ ID NO: 14 and 15. Kits having the primer pair to allow for the amplification of the desired junction are further provided.

Thus, in specific embodiments, a method of identifying a plant with enhanced resistance to cyst nematode comprising detecting the DNA junction formed at the breakpoint of a duplicated region within the rhg1 locus is provided. The method comprises (a) extracting a DNA sample from the soybean plant; (b) providing a pair of DNA primer molecules that can specifically amplify the desired DNA junction, (c) providing DNA amplification reaction conditions; (d) performing the DNA amplification reaction, thereby producing a DNA amplicon molecule; and (e) detecting the DNA amplicon molecule, wherein the detection of said DNA amplicon molecule in the DNA amplification reaction indicates the presence of a soybean plant having enhanced resistance to cyst nematodes. In order for a nucleic acid molecule to serve as a primer or probe it need only be sufficiently complementary in sequence to be able to form a stable double-stranded structure under the particular solvent and salt concentrations employed.

In hybridization techniques, all or part of a polynucleotide that selectively hybridizes to a target polynucleotide having the desired DNA junction is employed. By "stringent conditions" or "stringent hybridization conditions" when referring to a polynucleotide probe is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length or less than 500 nucleotides in length.

As used herein, a substantially identical or complementary sequence is a polynucleotide that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)—0.61 (% form)—500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.) and Haymes et al. (1985) In: *Nucleic Acid Hybridization, a Practical Approach*, IRL Press, Washington, D.C.

A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Various methods of detection include, but are not limited to, Genetic Bit Analysis (Nikiforov et al. (1994) *Nucleic Acid Res.* 22: 4167-4175) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the Pyrosequencing technique as described by Winge ((2000) *Innov. Pharma. Tech.* 00: 18-24). In this method, an oligonucleotide is designed that overlaps the adjacent DNA and insert DNA junction. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen et al. ((1999) *Genome Res.* 9: 492-498, 1999) is also a method that can be used to detect an amplicon of the invention. Using this method, an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi et al. ((1996) *Nature Biotech.* 14: 303-308). Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

As used herein, "kit" refers to a set of reagents for the purpose of performing the various method of detecting or identifying provided herein, more particularly, the identification and/or the detection of a soybean plant having an enhance resistance to cyst nematode.

Once the soybean plant with a duplication of a region within the rhg1 locus conferring resistance to cyst nematode has been identified, the plant or any one of its progeny having this region can be selected and crossed with a second soybean plant. In specific embodiments, the duplication of a region within the rhg1 locus conferring resistance to cyst nematode can be introgressed into a second soybean plant to produce an introgressed soybean germplasm.

V. Transgenic Plants Having an Enhanced Resistance to Cyst Nematode

A transgenic approach can be used to generate additional cyst nematode resistant materials. Specifically, transgenic integration of one or more of the genes contained within the duplicated region of the rhg1 locus (for example, one or more of the genes contained between about genomic position GM18:1663448 and about position GM18:1632228) can be introduced into a plant or plant cell and expressed and thereby confer enhanced resistance to cyst nematodes. Thus, plants, plant cells and plant parts having an increased level of expression of one or more genes found between about genomic position GM18:1663448 and about position GM18:1632228 are provided.

In specific embodiments, a plant, plant cell, seed, grain or plant part (particularly a soybean plant, plant cell, seed or grain) is provided comprising at least one heterologous polynucleotide stably incorporated in the genome comprising at least gene found between about genomic position GM18:1663448 and about position GM18:1632228. In specific embodiments, the heterologous polynucleotide comprises at least one of the sequences of Glyma18g2580 (SEQ ID NO: 3), Glyma18g2590 (SEQ ID NO:2), Glyma18g2600 (SEQ ID NO:4), Glyma18g2610 (SEQ ID NO:5), or Glyma18g2570 (SEQ ID NO:1), or an active variant or fragment thereof. The active variant or fragment of the gene will continue to confer enhanced resistance to cyst nematodes.

In addition, while any combination of SEQ ID NO: 1, 2, 3, 4, or 5 or active variants or fragments thereof can be introduced into the plant or plant part, the plant or plant part can further comprise multiple copies of the same heterologous polynucleotide. For example, the plant can comprise at least 2, 3, 4, 5, or more copies of any one of, or any combination of, Glyma18g2580 (SEQ ID NO: 3), Glyma18g2590 (SEQ ID NO:2), Glyma18g2600 (SEQ ID NO:4), Glyma18g2610 (SEQ ID NO:5), or Glyma18g2570 (SEQ ID NO:1), or an active variant or fragment thereof.

In specific embodiments, the heterologous polynucleotide of SEQ ID NO: 1, 2, 3, 4 or 5 or the active variant or fragment thereof is operably linked to a constitutive, tissue-preferred, or other promoter for expression in plants. In specific embodiments the promoter is heterologous to the polynucleotide of SEQ ID NO: 1, 2, 3, 4 or 5.

In specific embodiments the plant or plant cell having the heterologous polynucleotide is a soybean plant. However, the sequence can be introduced into any plant of interest, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea* batatus), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and Eucalyptus. In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

A. Variants and Fragments of Glyma18g2580, Glyma18g2590, Glyma18g2600, Glyma18g2610, and Glyma18g2570

"Variants" is intended to mean substantially similar sequences. For polynucleotides, a variant comprises a polynucleotide having a deletion (i.e., truncations) at the 5' and/or 3' end and/or a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides found between about genomic position GM18:1663448 and about position GM18:1632228, particularly, SEQ ID NO: 1, 2, 3, 4, or 5. Variant polynucleotides also include synthetically derived polynucleotides, such as those generated, for example, by using site-directed mutagenesis or gene synthesis but which still retain the ability to enhance resistance to cyst nematodes.

An active variant of any one of SEQ ID NO: 1, 2, 3, 4, or 5 can comprise a polynucleotide having at least 70%, 75%, 80%, 85%, 90%, 91%, 92%, 93%, 94%, 95%, 96%, 97%, 98% or 99% sequence identity to SEQ ID NO: 1, 2, 3, 4, or 5, as determined by sequence alignment programs and parameters described elsewhere herein, and when expressed, the sequence continue to confer enhanced resistance to cyst nematodes. Non-limiting examples of variants of SEQ ID NO: 1, 2, 3, and 5 are set forth in Table 2.

Obviously, the mutations that will be made in the DNA encoding the variant must not place the sequence out of reading frame and optimally will not create complementary regions that could produce secondary mRNA structure. See, EP Patent Application Publication No. 75,444. Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

By "fragment" is intended a portion of the polynucleotide or a portion of the amino acid sequence and hence protein encoded thereby. Fragments of a polynucleotide may encode protein fragments that retain the ability to enhance resistance to nematodes. Fragments of a nucleotide sequence may range from at least about 20 nucleotides, about 50 nucleotides, about 100 nucleotides, and up to the full-length polynucleotide encoding the polypeptides that confer enhanced resistance to cyst nematodes. A fragment of a SEQ ID NO: 1, 2, 3, 4 or 5 polynucleotide that encodes a biologically active portion and thereby enhances resistance to cyst nematodes will comprise at least 50, 75, 100, 150, 175, 200, 225, 250, 275, 300, 325, 350, 375, 400, 410, 415, 420, 425, 430, 435, or 440 contiguous nucleotides, or up to the total number of nucleotides present in a full-length sequences.

B. Polynucleotide Constructs

The polynucleotides disclosed herein that confer enhanced resistance to cyst nematodes (i.e., SEQ ID NO: 1, 2, 3, 4, or 5 or active variants and fragments thereof) can be provided in expression cassettes for expression in the plant of interest. The cassette can include 5' and 3' regulatory sequences operably linked to the polynucleotide or active variant or fragment thereof conferring enhanced resistance to cyct nematodes. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide or active variant or fragment thereof to be under the transcriptional regulation of the regulatory regions. The expression cassette may additionally contain selectable marker genes.

The expression cassette can include in the 5'-3' direction of transcription, a transcriptional and translational initiation region (i.e., a promoter), a polynucleotide or active variant or fragment thereof conferring enhanced resistance to cyst nematode (i.e., SEQ ID NO: 1, 2, 3, 4 or 5), and a transcriptional and translational termination region (i.e., termination region) functional in plants. The regulatory regions (i.e., promoters, transcriptional regulatory regions, and translational termination regions) and/or the polynucleotide or active variant or fragment thereof may be native/analogous to the host cell or to each other. Alternatively, the regulatory regions and/or the sequences conferring enhanced resistance to cyst nematode of or active variant or fragment thereof may be heterologous to the host cell or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

As used herein, polynucleotide or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A polypeptide expressed in vitro or in vivo from a recombinant polynucleotide is an example of a recombinant polypeptide. Likewise, a polynucleotide sequence that does not appear in nature, for example, a variant of a naturally occurring gene is recombinant.

The termination region may be native with the transcriptional initiation region or active variant or fragment thereof, may be native with the plant host, or may be derived from another source (i.e., foreign or heterologous) to the promoter, the polynucleotide or active fragment or variant thereof encoding the polypeptide enhancing resistance to cyst nematode, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gown (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385. See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used to express the various sequence set forth in SEQ ID NO:1, 2, 3, 4, or 5 or the active variant or fragments there, including the native promoter of the polynucleotide sequence of interest. The promoters can be selected based on the desired outcome. Such promoters include, for example, constitutive, inducible, tissue-preferred, or other promoters for expression in plants or in any organism of interest. In specific embodiments, the promoters are heterologous to the sequences being expressed.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target expression within a particular plant tissue. Tissue-preferred promoters include those described in Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic*

*Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat et al. *Plant Sci.* 47, 95-102 (1986); Reina et al. *Nucleic Acids Res.* 18 (21), 6426 (1990); and Kloesgen et al., *Mol. Gen. Genet.* 203, 237-244 (1986). Promoters that express in the embryo, pericarp, and endosperm are disclosed in U.S. Patent Application Ser. No. 60/097,233 filed Aug. 20, 1998 and U.S. Patent Applicaton Ser. No. 60/098,230 filed Aug. 28, 1998. The disclosures each of these are incorporated herein by reference in their entirety.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Synthetic promoters can be used to express the various sequences that confer tolerance to cyst nematodes or biologically active variants and fragments thereof.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners; the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters. See, for example, the glucocorticoid-inducible promoter in Schena et al. (1991) *Proc. Natl. Acad. Sci. USA* 88:10421-10425 and McNellis et al. (1998) *Plant J.* 14(2):247-257 and the tetracycline-inducible and tetracycline-repressible promoters for example, Gatz et al. (1991) *Mol. Gen. Genet.* 227:229-237, and U.S. Pat. Nos. 5,814,618 and 5,789,156, herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, dicamba, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon, pp.* 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph. D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph. D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology, Vol.* 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention, including for example, DsRed.

C. Stacking Other Traits of Interest

In some embodiments, the polynucleotides conferring enhanced tolerance to cyst nematodes or active variants and fragments thereof are engineered into a molecular stack. Thus, the various plants, plant cells and seeds disclosed herein can further comprise one or more traits of interest, and in more specific embodiments, the host cell, plant, plant part or plant cell is stacked with any combination of polynucleotide sequences of interest in order to create plants with a desired combination of traits. As used herein, the term "stacked" includes having the multiple traits present in the same plant or organism of interest. In one non-limiting example, "stacked traits" comprise a molecular stack where the sequences are physically adjacent to each other. A trait, as used herein, refers to the phenotype derived from a particular sequence or groups of sequences.

The plant or plant cell or plant part having the sequence conferring enhanced tolerance to cyst nematodes or active variants or fragments thereof can also be combined with at least one other trait to produce plants that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802; and 5,703,409; U.S. Pat. No. 5,850,016); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

Desired trait combinations also include LLNC (low linolenic acid content; see, e.g., Dyer et al. (2002) *Appl. Microbiol. Biotechnol.* 59: 224-230) and OLCH (high oleic acid content; see, e.g., Fernandez-Moya et al. (2005) *J. Agric. Food Chem.* 53: 5326-5330).

The plant or plant cell or plant part having the sequence or an active variant or fragment thereof which confers enhanced resistance to cyst nematodes can also be combined with other desirable traits such as, for example, fumonisim detoxification genes (U.S. Pat. No. 5,792,931), avirulence and disease resistance genes (Jones et al. (1994) *Science* 266: 789; Martin et al. (1993) *Science* 262: 1432; Mindrinos et al. (1994) *Cell* 78: 1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In other embodiments, the plant or plant cell or plant part having the sequence that confers enhanced resistance to cyst nematode or an active variant or fragment thereof may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; 5,593,881; Geiser et al. (1986) *Gene* 48: 109; Lee et al. (2003) *Appl. Environ. Microbiol.* 69: 4648-4657 (Vip3A); Galitzky et al. (2001) *Acta Crystallogr. D. Biol. Crystallogr.* 57: 1101-1109 (Cry3Bb1); and Herman et al. (2004) *J. Agric. Food Chem.* 52: 2726-2734 (Cry1F)), lectins (Van Damme et al. (1994) *Plant Mol. Biol.* 24: 825, pentin (described in U.S. Pat. No. 5,981,722), and the like. The combinations generated can also include multiple copies of any one of the polynucleotides of interest.

In another embodiment, the plant or plant cell or plant part having the sequence that confers enhanced resistance to cyst nematode or an active variant or fragment thereof can also be combined with the Rcg1 sequence or biologically active variant or fragment thereof. The Rcg1 sequence is an anthracnose stalk rot resistance gene in corn. See, for example, U.S. patent application Ser. Nos. 11/397,153, 11/397,275, and Ser. No. 11/397,247, each of which is herein incorporated by reference.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Any plant having the sequence that confers enhanced resistance to cyst nematode disclosed herein or an active variant or fragment thereof can be used to make a food or a feed product. Such methods comprise obtaining a plant, explant, seed, plant cell, or cell comprising the sequence that confers enhanced resistance to cyst nematode (i.e., SEQ ID NO: 1, 2, 3, 4, or 5) or active variant or fragment thereof and processing the plant, explant, seed, plant cell, or cell to produce a food or feed product.

D. Methods of Introducing

Various methods can be used to introduce a sequence of interest into a plant or plant part. "Introducing" is intended to mean presenting to the host cell, plant, plant cell or plant part the polynucleotide or polypeptide in such a manner that the sequence gains access to the interior of a cell of the plant or organism. The methods of the invention do not depend on a particular method for introducing a sequence into an organism or a plant or plant part, only that the polynucleotide or polypeptides gains access to the interior of at least one cell of the organism or the plant. Methods for introducing polynucleotide or polypeptides into various organisms, including plants, are known in the art including, but not limited to, stable transformation methods, transient transformation methods, and virus-mediated methods.

"Stable transformation" is intended to mean that the nucleotide construct introduced into a plant integrates into the genome of the plant or organism of interest and is capable of being inherited by the progeny thereof. "Transient transformation" is intended to mean that a polynucleotide is introduced into the plant or organism of interest and does not integrate into the genome of the plant or organism or a polypeptide is introduced into a plant or organism.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563, 055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and U.S. Pat. No. 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean);

Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322, 783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the sequences that confer enhanced resistance to cyst nematodes (i.e., any one or combination of SEQ ID NO: 1, 2, 3, 4, or 5) or active variants or fragments thereof can be introduced into plants by contacting plants with a virus or viral nucleic acids. Generally, such methods involve incorporating a nucleotide construct of the invention within a DNA or RNA molecule. It is recognized that the sequence that confers enhanced resistance to cyst nematodes (i.e., any one or combination of SEQ ID NO: 1, 2, 3, 4, or 5) may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome. Other methods to target polynucleotides are set forth in WO 2009/114321 (herein incorporated by reference), which describes "custom" meganucleases produced to modify plant genomes, in particular the genome of maize. See, also, Gao et al. (2010) *Plant Journal* 1:176-187.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

Transformed plant cells which are derived by plant transformation techniques, including those discussed above, can be cultured to regenerate a whole plant which possesses the transformed genotype (i.e., that confer enhanced resistance to cyst nematodes (i.e., any one or combination of SEQ ID NO: 1, 2, 3, 4, or 5)), and thus the desired phenotype, such as enhanced resistance to cyst nematodes. For transformation and regeneration of maize see, Gordon-Kamm et al., *The Plant Cell*, 2:603-618 (1990). Plant regeneration from cultured protoplasts is described in Evans et al. (1983) *Protoplasts Isolation and Culture, Handbook of Plant Cell Culture*, pp 124-176, Macmillan Publishing Company, New York; and Binding (1985) *Regeneration of Plants, Plant Protoplasts* pp 21-73, CRC Press, Boca Raton. Regeneration can also be obtained from plant callus, explants, organs, or parts thereof. Such regeneration techniques are described generally in Klee et al. (1987) *Ann Rev of Plant Phys* 38:467. See also, e.g., Payne and Gamborg.

One of skill will recognize that after the expression cassette containing the sequence that confer enhanced resistance to cyst nematodes (i.e., any one or combination of SEQ ID NO: 1, 2, 3, 4, or 5) is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the sequence that confers enhanced resistance to cyst nematodes (i.e., any one or combination of SEQ ID NO: 1, 2, 3, 4, or 5). Progeny and variants, and mutants of the regenerated plants are also included within the scope of the invention, provided that these parts comprise the introduced nucleic acid sequences.

In one embodiment, a homozygous transgenic plant can be obtained by sexually mating (selfing) a heterozygous transgenic plant that contains a single added heterologous nucleic acid, germinating some of the seed produced and analyzing the resulting plants produced for altered cell division relative to a control plant (i.e., native, non-transgenic). Back-crossing to a parental plant and out-crossing with a non-transgenic plant are also contemplated.

E. Methods for Increasing Expression and/or Concentration of at Least One Sequence That Confers Enhanced Resistance to Cyst Nematodes in a Plant or Plant Part A method for increasing the activity and/or concentration of at least one sequence that confers enhanced resistance to cyst nematodes (i.e., SEQ ID NO: 1, 2, 3, 4, or 5 or an active variant or fragment thereof) in a plant, plant cell, plant part, explant, and/or seed is provided. In further embodiments, the concentration/level of the at least one sequence that confers enhanced resistance to cyst nematodes (i.e., SEQ ID NO: 1, 2, 3, 4, or 5 or an active variant or fragment thereof) is increased in a plant or plant part by at least 10%, 20%, 30%, 40%, 50%, 60%, 70%, 80%, 90%, 100%, 200%, 500%, 1000%, 5000%, or 10,000% relative to an appropriate control plant, plant part, or cell which did not have the sequence. In still other embodiments, the level of the at least one sequence that confers enhanced resistance to cyst nematodes (i.e., SEQ ID NO: 1, 2, 3, 4, or 5 or an active variant or fragment thereof) in the plant or plant part is increased by 10, 20, 30, 40, 50, 60, 70, 80, 90, 100 fold or more relative to an appropriate control plant, plant part, or cell which did not have the sequence. Such an increase in the level of the at least one sequence that confers enhanced resistance to cyst nematodes (i.e., SEQ ID NO: 1, 2, 3, 4, or 5 or an active variant or fragment thereof) can be achieved in a variety of ways including, for example, by the expression of multiple copies of one or more of at least one sequence that confers enhanced resistance to cyst nematodes (i.e., SEQ ID NO: 1, 2, 3, 4, or 5 or an active variant or fragment thereof) and/or by employing a promoter to drive higher levels of expression of one or more of the sequences.

In specific embodiments, at least one polynucleotide that confers enhanced resistance to cyst nematodes (i.e., SEQ ID NO: 1, 2, 3, 4, or 5 or an active variant or fragment thereof or any combination thereof) is introduced into the plant, plant cell, explant or plant part. Subsequently, a plant cell or plant having the introduced sequence is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of at least one sequence that confers enhanced resistance to cyst nematodes (i.e., SEQ ID NO: 1, 2, 3, 4, or 5 or an active variant or fragment thereof) in the plant.

VI. Sequence Comparisons

The following terms are used to describe the sequence relationships between two or more polynucleotides or polypeptides: "reference sequence", "comparison window", "sequence identity", and, "percent sequence identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence or protein sequence.

As used herein, "comparison window" makes reference to a contiguous and specified segment of a polypeptide sequence, wherein the polypeptide sequence in the comparison window may comprise additions or deletions (i.e., gaps) compared to the reference sequence (which does not comprise additions or deletions) for optimal alignment of the two polypeptides. Generally, the comparison window is at least 5, 10, 15, or 20 contiguous amino acid in length, or it can be 30, 40, 50, 100, or longer. Those of skill in the art understand that to avoid a high similarity to a reference sequence due to inclusion of gaps in the polypeptide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST®, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5: 151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST® programs of Altschul et al (1990) *J. Mol. Biol.* 215:403 are based on the algorithm of Karlin and Altschul (1990) supra. BLAST® nucleotide searches can be performed with the BLASTN program, score=100, wordlength=12, to obtain nucleotide sequences homologous to a nucleotide sequence encoding a protein of the invention. BLAST® protein searches can be performed with the BLASTX program, score=50, wordlength=3, to obtain amino acid sequences homologous to a protein or polypeptide of the invention. BLASTP protein searches can be performed using default parameters. See the National Center for Biotechnology Information website.

To obtain gapped alignments for comparison purposes, Gapped BLAST (in BLAST® 2.0) can be utilized as described in Altschul et al. (1997) Nucleic Acids Res. 25:3389. Alternatively, PSI-BLAST (in BLAST® 2.0) can be used to perform an iterated search that detects distant relationships between molecules. See Altschul et al. (1997) supra. When utilizing BLAST®, Gapped BLAST, or PSI-BLAST, the default parameters of the respective programs (e.g., BLASTN for nucleotide sequences, BLASTP for proteins) can be used. See the National Center for Biotechnology Information website. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity). When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percent sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percent sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acids substitution matrices and their use in quantifying the similarity between two sequences are well-known in the art and described, e.g., in Dayhoff et al. (1978) "A model of evolutionary change in proteins." In. "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA. 89:10915-10919. The BLOSUM62 matrix (FIG. 10) is often used as a default scoring substitution matrix in sequence alignment protocols such as Gapped BLAST® 2.0. The gap existence penalty is imposed for the introduction of a single amino acid gap in one of the aligned sequences, and the gap extension penalty is imposed for each additional empty amino acid position inserted into an already opened gap. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST® 2.0, described in Altschul et al, (1997) Nucleic Acids Res. 25:3389-3402, and made available to the public at the National Center for Biotechnology Information website. Optimal alignments, including multiple alignments, can be prepared using, e.g., PSI-BLAST, available at the National Center for Biotechnology Information website, and described by Altschul et al, (1997) Nucleic Acids Res. 25:3389-3402.

Non-limiting embodiments include:

1. A method of identifying a first soybean plant or a first soybean germplasm with enhanced resistance to cyst nematode comprising detecting in the genome of said first soybean plant or in the genome of said first soybean germplasm at least one marker allele associated with a duplication of a region within the rhg1 locus.

2. The method of embodiment 1, wherein the duplication of the region within the rhg1 locus comprises a tandem duplication of the soybean genome between about position GM18:1663448 and about position GM18:1632228.

3. The method of embodiment 1, wherein the duplication of the region within the rhg1 locus comprises the region as set forth in at least one of SEQ ID NO: 1, 2, 3, 4, or 5.

4. The method of embodiment 1, wherein the marker allele comprises at least one polymorphism set forth in Table 1 or Table 2.

5. The method of any one of embodiments 1-4, wherein the method further comprises selecting the first soybean plant or the first soybean germplasm or a progeny thereof having the at least one marker allele.

6. The method of embodiment 5, further comprising crossing the selected first soybean plant with a second soybean plant.

7. A method of identifying a first soybean plant or a first soybean germplasm with enhanced resistance to cyst nematode comprising detecting in the genome of said first soybean plant or said first soybean germplasm a duplication of a region within the rhg1 locus.

8. The method of embodiment 7, wherein the duplication of the region within the rhg1 locus comprises a tandem duplication of the region of the soybean genome between about position GM18:1663448 and about position GM18: 1632228.

9. The method of embodiment 7, wherein the duplication of the region within the rhg1 locus comprises the region as set forth in at least one of SEQ ID NO: 1, 2, 3, 4, or 5.

10. The method of embodiment 7, wherein the duplication of the region within the rhg1 locus comprises each of the regions as set forth in SEQ ID NO: 1, 2, 3, 4, and 5.

11. The method of embodiment 7, 8, 9 or 10, wherein said detecting comprises quantitative PCR or other quantitative technique.

12. The method of any one of embodiments 7-11, wherein the method further comprises selecting the first soybean plant, the first soybean germplasm or a progeny thereof having the duplication in the region of the rhg1 locus.

13. The method of embodiment 12, further comprising crossing the selected first soybean plant with a second soybean plant.

14. A method of identifying a first soybean plant or a first soybean germplasm with enhanced resistance to cyst nematode comprising detecting in said first soybean plant or in said first soybean germplasm an increased copy number of at least one of SEQ ID NO: 1, 2, 3, 4, or 5 or an active variant or fragment thereof.

15. The method of embodiment 14, wherein said method comprises detecting an increased copy number of SEQ ID NOS: 1, 2, 3, 4 and 5 or an active variant or fragment thereof.

16. The method of any one of embodiments 14-15, wherein the method further comprises selecting the first soybean plant, the first soybean germplasm or a progeny thereof having the increased copy number of at least one of SEQ ID NO: 1, 2, 3, 4, or 5.

17. The method of embodiment 16, further comprising crossing the selected first soybean plant with a second soybean plant.

18. A method for identifying a first soybean plant or a first soybean germplasm with enhanced resistance to cyst nematode comprising detecting in the genome of said first soybean plant or said first soybean germplasm a DNA junction formed at the breakpoint of a duplicated region within the rhg1 locus.

19. The method of embodiment 18, wherein the duplicated region within the rhg1 locus comprises a tandem duplication of the region of the soybean genome between about position GM18:1663448 and about position GM18: 1632228.

20. The method of embodiment 18, wherein the DNA junction comprises the sequence set forth in any one of SEQ ID NOS: 6, 7, 8 or 9 or a fragment thereof.

21. The method of embodiment 18, wherein detecting the novel DNA junction comprises PCR amplification of the DNA junction formed at the breakpoint of the duplicated region within the rhg1 locus.

22. The method of embodiment 21, wherein said PCR amplification employs the primer pair set forth in SEQ ID NO: 14 and 15.

23. The method of embodiment 18, wherein detecting the DNA junction comprises DNA sequencing.

24. The method of any one of embodiments 18-23, wherein the method further comprises selecting the first soybean plant, the first soybean germplasm or a progeny thereof having the DNA junction formed at the breakpoint of the duplicated region within the rhg1 locus.

25. The method of embodiment 24, further comprising crossing the selected first soybean plant with a second soybean plant.

26. A plant or plant cell comprising a heterologous polynucleotide operably linked to a promoter active in the plant or plant cell, wherein said heterologous polynucleotide comprises:
a) the nucleotide sequence as set forth in any one of SEQ ID NO: 1, 2, 3, 4, or 5, or any combination thereof; or,
b) the nucleotide sequence having at least 85% sequence identity to any one of SEQ ID NO: 1, 2, 3, 4, or 5, or any combination thereof; wherein expression of said heterologous polynucleotide enhances said plants resistance to cyst nematode.

27. The plant or plant cell of embodiment 26, wherein said plant or plant cell is from a monocot.

28. The plant or plant cell of embodiment 27, wherein said monocot is maize, wheat, rice, barley, sugarcane, sorghum, or rye.

29. The plant or plant cell of embodiment 26, wherein said plant or plant cell is from a dicot.

30. The plant or plant cell of embodiment 29, wherein the dicot is Brassica, sunflower, cotton, or alfalfa.

31. The plant or plant cell of embodiment 29, wherein the dicot is soybean.

32. A transgenic seed from the plant of any one of embodiments 26-31, wherein said transgenic seed comprise the heterologous polynucleotide.

33. A method to enhance resistance to cyst nematode in a plant comprising introducing into a plant cell a heterologous polynucleotide operably linked to a promoter active in the plant, wherein said heterologous polynucleotide comprises:
a) a nucleotide sequence as set forth in any one of SEQ ID NO: 1, 2, 3, 4, or 5, or any combination thereof; or,
b) a nucleotide sequence having at least 85% sequence identity to any one of SEQ ID NO: 1, 2, 3, 4, or 5, or any combination thereof;
wherein expression of said heterologous polynucleotide enhances said plants resistance to cyst nematode.

34. The method of embodiment 33, wherein said plant is a monocot.

35. The method of embodiment 34, wherein said monocot is maize, wheat, rice, barley, sugarcane, sorghum, or rye.

36. The method of embodiment 33, wherein said plant is a dicot.

37. The method of embodiment 36, wherein the dicot is Brassica, sunflower, cotton, or alfalfa.

38. The method of embodiment 36, wherein the dicot is soybean.

EXPERIMENTAL

The following example is offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

We have observed a previously unexplained pattern of inherited heterozygosity at the rhg1 locus within lines harboring the PI88788 derived rhg1-b allele. Several SNP variants within the fine-mapped region of rhg1-b are heterozygous across PI88788 derived resistant lines (FIG. 1). This observation led us to hypothesize that tandem duplication and subsequent degeneration of paralogous sequence could be responsible for the observed heterozygosity at this locus.

In order to investigate the paralogous copy-count, we analyzed deep resequencing data from Peking, PI88788, and Lincoln. Visualization of sequencing coverage at the rhg1 locus suggested a substantial increase in copy-number for Peking and PI88788 relative to Lincoln consistent with duplication of nucleotide sequences within this locus (FIG. 2). Furthermore, paired-end sequencing reads at the outer extremes of the duplicated region exhibited discordant alignments consistent with tandem duplication at the locus. Taken together, these results suggest that tandem duplication of nucleotide sequences within the rhg1 locus.

Quantitative comparison of the sequencing depth within and adjacent to the putative duplication was performed by normalizing PI88788 and Peking coverage to Lincoln in a moving window across the Rhg1 locus. Consistent with the visualization, copy-number analysis indicated a 3-fold and 9-fold increase in Peking and PI88788 respectively relative to Lincoln within the tandem duplication but not in the regions immediately adjacent (FIG. 3). These results suggest that rhg1 and rhg1-b represent two distinct copy-variable alleles of an identical structural variant consistent with different levels of phenotypic resistance.

To validate the observed copy-number qPCR assays were designed against the single-copy and variable-copy regions of the rhg1 locus. The results of these assays are consistent with sequencing data suggesting an approximately 4-fold and 9-fold copy-number increase in Peking and PI88788 respectively relative to susceptible lines (FIG. 4).

In order to more precisely define the breakpoints of the duplication, paired-end sequencing reads with discordant alignments at the boundaries of the event were assembled, from which a 158 bp contig was recovered. The alignment of this contig to the reference is consistent with a tandem duplication event with breakpoints at Gm18:1663448 and Gm18:1632228 (FIG. 5). Interestingly, there is a 3-bp microhomology shared between the breakpoints. To evaluate the correctness of the putative breakpoints, a series of PCR primers were designed to amplify fragments which span the junction of the tandem duplication.

Amplification of PCR products across the breakpoints in Peking and PI88788 derived resistant lines but not susceptible genotypes are consistent with the described tandem duplication (FIG. 6). Furthermore, the size of amplicons is consistent our expectations given the physical positions of putative breakpoints. In order to validate the targeted PCR products is in fact being observed in these lines, traditional Sanger sequencing was performed for Peking and PI88788 amplicons (FIG. 7).

Taken together, our supporting results provide evidence that the rhg1 locus of Peking and PI88788 harbors identical tandem duplication with two distinct copy-variable alleles. The observed increase in copy-number from Peking to PI88788 can be explained by homologous recombination between the paralogous copies and unequal crossing over. Assuming that positive selective pressure is acting on expansion of the copy-count at the Rhg1 locus it follows that this tandem duplication may harbor a gene or genes whose dosage contributes favorably to the SCN resistance phenotype which has been fine mapped to this region.

This region contains four genes which are completely duplicated: Glyma18g2580, Glyma18g2590, Glyma18g2600, Glyma18g2610; and one gene which is partially duplicated: Glyma18g2570. Striking anecdotal evidence supports the involvement of one or more of these genes in SCN resistance: the coding sequences of two genes (Glyma18g2600 and Glyma18g2610) are unaffected by polymorphism in both sources. Interestingly, Glyma18g2600 is predicted to be a signal-mediating scaffolding protein and annotated as a 'predicted defense related gene'.

A useful by-product of our analysis has been the development of a qPCR assay which can be used to screen additional candidate material. This assay would be useful for identifying either the described rhg1 and rhg1-b copy-variable allele(s) or additional alleles which have not been described.

Materials and Methods

Whole Genome Shotgun Sequencing

Whole genome shotgun sequencing libraries were prepared for Peking, PI88788 and Lincoln by Mary Beatty Lab according to standard sequencing protocols. Libraries were sequenced on the Illumina HiSeq instrument to an average depth of 17× genome sequencing coverage. Sequenced reads were aligned to the Soybean Genomic Assembly Glyma 1.01 (JGI) by bowtie2 and compressed binary alignment/map files were generated by SAMtools.

Breakpoint Assembly from Sequencing Reads

Paired-end sequencing reads which aligned to the boundaries of the putative duplication were extracted from the BAM file by SAMtools and assembled using. The resulting contigs were blasted against the Soybean Genomic Assembly Glyma1.01 (JGI) the Pioneer BLAST® Submission and Retrieval page with settings Expect=0.01.

Copy-Number Analysis

Copy-number analysis was performed by calculating the sequencing coverage in a moving window across the rhg1 fine-map region. Coverage windows within each sample were normalized to the median sequencing depth and then compared as a ratio of resistant to susceptible sources (Normalized coverage ratio). This ratio approximates the fold-difference between the two lines being compared.

qPCR Assay

PCR primers were designed against the single-copy and variable-copy regions of the rhg1 fine-mapped locus, six copy-variable and six single-copy primer-pairs yielded useful information. Two sources of Peking (Peking and 91Y90) and PI88788 (PI88788 and 93Y13) resistance and three susceptible lines (Lincoln, Dunfield and CNS) were assayed in four replicates for all primer-pairs. The qPCR was completed using the SYBR-Green assay. Replicates were averaged and ΔΔCt analysis was performed pair-wise and averaged between every variable-copy and single-copy combination. The distribution of these results was plotted for each pairwise comparison between Peking, PI88788 and susceptible.

The results confirm that the duplicated portion of the genome is actually duplicated.

Example 2. Conditions for PCR Amplification of Breakpoint Sequences

94 C/4 min
35 Cycles:
  94 C/30 s
  60 C/45 s
  72 C/2 min
Optional Dissociation Stage:
  72 C/5 min
Primers were designed using Primer3 (biocomplx.phibred.com/hu/primer3.html) and checked for uniqueness using GPS (bioprodlx.phibred.com/Primer_search/cgi-bin/primer_hit_form.cgi).
Product Size Range: 550-650 bps
Default Settings
Conditions for qPCR copy assay
95 C/5 min
40 Cycles:
  95 C/20 sec
  60 C/45 sec
Optional Dissociation Stage:
  95 C/15 sec
  60 C/20 sec
  95 C/15 sec
Primers were designed using Primer3 (biocomplx.phibred.com/hu/primer3.html) and checked for uniqueness using GPS (bioprodlx.phibred.com/Primer_search/cgi-bin/primer_hit_form.cgi).
Product Size Range: 50-200 bps
Primer Size: 18-24 opt 20
Tm: 59-62° C. (Primer pairs within 1° C. of each other)
Default Settings
Nuclear DNA Extraction Protocol
  Adapted from Meizhong Luo and Rod Wing. An Improved Method for Plant BAC Library Construction. Methods in Molecular Biology, vol. 236: Plant Functional Genomics: Methods and Protocols
Materials per extraction:
  5—Sheets 6"×6" Miracloth
  3—50 mL tubes
  1—funnel
  Orbital Shaker
Solutions:
2× Nuclear Isolation Buffer (NIB) (2 L)
  20 mM Tris-HCl, pH 8.0 (40 mL)
  20 mM EDTA, pH 8.0 (80 mL)
  200 mM KCl (29.82 g)
  1 M sucrose (684.6 g)
  8 mM spermidine (4.1 g)
  2 mM spermine (1.4 g)
  Sterilize by filtration. Store at 4° C.
  NOTE: Dilute with sterile water to prepare 1×NIB, NIBT, and NIBM
1×NIBT: 1×NIB with 10% Triton X-100 (make 3 mL per extraction)
1×NIBM: 1×NIB with 0.1% β-mercaptoethanol (make 65 mL per extraction)

Protocol:
1. Grind 1.5 g of lyophilized tissue in paint shaker
2. Transfer the ground tissue into a 50 mL tube containing 45 mL ice cold NIBM
3. Keep tube on ice for 15 min while shaking gently on orbital shaker
4. Filter the homogenate through 3 layers of Miracloth into a clean 50 mL tube.
   Squeeze the pellet to allow maximum recovery of nuclei-containing solution. Use additional 10 mL NIBM to wash the pellet and squeeze again.
5. Filter the nuclei-containing solution through 2 additional layers of Miracloth into a clean 50 mL Tube.
6. Add 1:20 of NIBT (2.75 mL) to the nuclei-containing solution and keep tube on ice for 15 min while shaking gently on orbital shaker
7. Centrifuge the tubes at 4000 rpm at 4° C. for 20 min
8. Decant the supernatant and add 5 mL of NIBM to first tube. Resuspend via vortex.
9. Centrifuge mixture at 4000 rpm at 4° C. for 15 min
10. Decant the supernatant and proceed to Urea Extraction
11. Add 5 mL 7M Urea Buffer—Resuspend
12. Add 10 uL RNAse—Incubate 37 C. for 30 min
13. Add 5 mL 25:24:1 Chloroform-Phenol-Octanol—Rock for 10 min—Centrifuge 20 min at 4000 rpm
14. Transfer supernatant, add 450 uL NaOAc and 5 mL Isopropanol to new tube
15. Spin 15 min at 4000 rpm. Decant Supernatant. Clean with 70% ethanol.
16. Resuspend in 500 uL 10 mM Tris.

Example 3

Table 1 provides a list of polymorphic sites found within the rhg1 locus. The chromosomal position is denoted in the first two columns. "Ref" denotes the nucleotide occurring in the reference soybean sample, and "ALT" denotes the nucleotide found in the soybean lines having enhanced resistance to SCN. The presence of the nucleotide alteration in the Peking and the P188788 lines is denoted in the last two columns. Table 2 provides a list of polymorphic sites found within the coding regions of the rhg1 locus, specifically polymorphisms in Glyma18g2580 (SEQ ID NO: 3), Glyma18g2590 (SEQ ID NO: 2), Glyma18g2600 (SEQ ID NO:4), Glyma18g2610 (SEQ ID NO:5); and Glyma18g2570 (SEQ ID NO:1) are provided. Thus, any one marker or any combination of the polymorphisms set forth in Tables 1 and 2 can be used to aid in identifying and selecting soybean plans with enhanced resistance to SCN.

TABLE 1

| #CHROM | POS | REF | ALT | Peking |
|---|---|---|---|---|
| Glyma18g2570 | | | | |
| Gm18 | 1631156 | G | C | Yes |
| Gm18 | 1631449 | C | T | Yes |
| Gm18 | 1631761 | G | T | Yes |
| Gm18 | 1632227 | A | G | Yes |
| Gm18 | 1633532 | A | G | Yes |
| Gm18 | 1633629 | T | A | Yes |
| Gm18 | 1633700 | G | A | Yes |
| Glyma18g2580 | | | | |
| Gm18 | 1636766 | T | C | Yes |
| Gm18 | 1638717 | T | C | Yes |

TABLE 1-continued

| #CHROM | POS | REF | ALT | Peking |
|---|---|---|---|---|
| Glyma18g2590 | | | | |
| Gm18 | 1644011 | C | T | Yes |
| Gm18 | 1642236 | T | C | Yes |
| Gm18 | 1643324 | C | T | Yes |
| Gm18 | 1643225 | C | G | Yes |
| Gm18 | 1642307 | C | T | Yes |
| Gm18 | 1642848 | G | A | Yes |
| Gm18 | 1644076 | G | C | Yes |
| Gm18 | 1644089 | G | A | Yes |
| Gm18 | 1640963 | C | T | Yes |
| Gm18 | 1641208 | G | A | Yes |
| Gm18 | 1641800 | C | A | Yes |
| Gm18 | 1644974 | C | A | Yes |
| Gm18 | 1644525 | T | C | Yes |
| Gm18 | 1640581 | C | T | Yes |
| Gm18 | 1642672 | C | G | Yes |
| Gm18 | 1644577 | T | G | Yes |
| Gm18 | 1644493 | C | T | Yes |
| Gm18 | 1645218 | A | T | Yes |
| Gm18 | 1641442 | A | G | Yes |
| Glyma18g2600 | | | | |
| Glyma18g2610 | | | | |
| Gm18 | 1652723 | T | C | Yes |

TABLE 2

| #CHROM | POS | REF | ALT | Peking | PI88788 |
|---|---|---|---|---|---|
| Gm18 | 1544945 | T | G | Yes | No |
| Gm18 | 1735510 | T | A | Yes | No |
| Gm18 | 1730855 | A | T | Yes | No |
| Gm18 | 1511134 | C | A | Yes | Yes |
| Gm18 | 1684932 | A | G | Yes | No |
| Gm18 | 1706708 | G | A | Yes | No |
| Gm18 | 1727903 | C | T | Yes | No |
| Gm18 | 1589715 | G | T | Yes | Yes |
| Gm18 | 1545209 | T | G | Yes | No |
| Gm18 | 1768415 | A | G | Yes | Yes |
| Gm18 | 1536883 | T | C | Yes | No |
| Gm18 | 1681958 | A | T | Yes | Yes |
| Gm18 | 1556781 | T | C | Yes | No |
| Gm18 | 1716068 | A | G | Yes | Yes |
| Gm18 | 1582195 | C | T | Yes | Yes |
| Gm18 | 1571774 | A | G | Yes | Yes |
| Gm18 | 1681493 | A | G | Yes | Yes |
| Gm18 | 1556678 | A | G | Yes | Yes |
| Gm18 | 1623900 | C | T | Yes | Yes |
| Gm18 | 1682230 | T | A | Yes | Yes |
| Gm18 | 1560784 | A | G | Yes | No |
| Gm18 | 1731656 | G | T | Yes | No |
| Gm18 | 1725991 | A | G | Yes | No |
| Gm18 | 1674291 | G | A | Yes | Yes |
| Gm18 | 1533453 | G | A | Yes | No |
| Gm18 | 1615080 | A | G | Yes | No |
| Gm18 | 1572987 | A | C | Yes | Yes |
| Gm18 | 1641442 | A | G | Yes | Yes |
| Gm18 | 1768805 | A | G | Yes | No |
| Gm18 | 1709751 | G | A | Yes | Yes |
| Gm18 | 1549465 | G | A | Yes | Yes |
| Gm18 | 1649892 | T | A | Yes | Yes |
| Gm18 | 1645218 | A | T | Yes | Yes |
| Gm18 | 1626676 | T | C | Yes | Yes |
| Gm18 | 1567661 | C | T | Yes | No |
| Gm18 | 1703321 | T | A | Yes | No |
| Gm18 | 1644493 | C | T | Yes | No |
| Gm18 | 1644577 | T | G | Yes | No |
| Gm18 | 1516872 | G | A | Yes | No |
| Gm18 | 1547825 | C | G | Yes | Yes |
| Gm18 | 1633532 | A | G | Yes | Yes |
| Gm18 | 1642672 | C | G | Yes | Yes |
| Gm18 | 1657506 | C | T | Yes | Yes |
| Gm18 | 1644525 | T | C | Yes | No |
| Gm18 | 1653661 | T | C | Yes | Yes |

TABLE 2-continued

| #CHROM | POS | REF | ALT | Peking | PI88788 |
|---|---|---|---|---|---|
| Gm18 | 1652453 | A | G | Yes | Yes |
| Gm18 | 1543932 | T | C | Yes | No |
| Gm18 | 1601192 | T | C | Yes | No |
| Gm18 | 1597849 | T | C | Yes | Yes |
| Gm18 | 1641800 | C | A | Yes | Yes |
| Gm18 | 1654906 | C | A | Yes | Yes |
| Gm18 | 1552732 | T | G | Yes | Yes |
| Gm18 | 1552753 | A | G | Yes | No |
| Gm18 | 1710311 | T | C | Yes | Yes |
| Gm18 | 1640963 | C | T | Yes | Yes |
| Gm18 | 1644089 | G | A | Yes | Yes |
| Gm18 | 1623024 | T | C | Yes | Yes |
| Gm18 | 1770832 | A | G | Yes | Yes |
| Gm18 | 1693289 | C | T | Yes | Yes |
| Gm18 | 1644076 | G | C | Yes | Yes |
| Gm18 | 1649630 | T | C | Yes | Yes |
| Gm18 | 1642848 | G | A | Yes | Yes |
| Gm18 | 1655593 | T | A | Yes | No |
| Gm18 | 1656348 | T | A | Yes | Yes |
| Gm18 | 1643225 | C | G | Yes | No |
| Gm18 | 1638717 | T | C | Yes | Yes |
| Gm18 | 1636305 | C | T | Yes | Yes |
| Gm18 | 1645359 | T | G | Yes | Yes |
| Gm18 | 1654849 | C | T | Yes | Yes |
| Gm18 | 1656044 | G | A | Yes | Yes |
| Gm18 | 1653887 | C | T | Yes | No |
| Gm18 | 1534496 | T | C | Yes | No |
| Gm18 | 1633700 | G | A | Yes | Yes |
| Gm18 | 1649385 | A | G | Yes | Yes |
| Gm18 | 1644011 | C | T | Yes | Yes |
| Gm18 | 1652235 | G | C | Yes | Yes |
| Gm18 | 1633948 | G | A | Yes | Yes |
| Gm18 | 1646008 | A | C | Yes | Yes |
| Gm18 | 1635588 | A | T | Yes | Yes |
| Gm18 | 1656898 | C | T | Yes | Yes |
| Gm18 | 1649069 | G | T | Yes | Yes |
| Gm18 | 1649293 | G | C | Yes | Yes |
| Gm18 | 1716401 | C | T | Yes | Yes |
| Gm18 | 1658284 | A | G | Yes | Yes |
| Gm18 | 1662766 | T | C | Yes | Yes |
| Gm18 | 1660183 | T | C | Yes | Yes |
| Gm18 | 1750228 | G | A | Yes | No |
| Gm18 | 1658707 | G | A | Yes | Yes |
| Gm18 | 1639589 | C | G | Yes | Yes |
| Gm18 | 1650140 | G | T | Yes | Yes |
| Gm18 | 1656394 | C | T | Yes | Yes |
| Gm18 | 1766174 | T | C | Yes | Yes |
| Gm18 | 1657162 | C | T | Yes | Yes |
| Gm18 | 1652401 | T | C | Yes | Yes |
| Gm18 | 1633629 | T | A | Yes | Yes |
| Gm18 | 1649328 | T | C | Yes | Yes |
| Gm18 | 1640338 | A | C | Yes | Yes |
| Gm18 | 1561036 | A | C | Yes | Yes |
| Gm18 | 1547861 | A | G | Yes | Yes |
| Gm18 | 1710204 | G | A | Yes | Yes |
| Gm18 | 1656462 | C | G | Yes | Yes |
| Gm18 | 1573221 | A | C | Yes | Yes |
| Gm18 | 1636766 | T | C | Yes | Yes |
| Gm18 | 1560705 | A | C | Yes | Yes |
| Gm18 | 1663181 | C | T | Yes | Yes |
| Gm18 | 1572279 | G | A | Yes | Yes |
| Gm18 | 1670005 | G | A | Yes | Yes |
| Gm18 | 1562844 | A | G | Yes | Yes |
| Gm18 | 1624569 | G | T | Yes | Yes |
| Gm18 | 1654119 | G | A | Yes | Yes |
| Gm18 | 1620249 | G | C | Yes | Yes |
| Gm18 | 1678344 | G | A | Yes | Yes |
| Gm18 | 1629210 | G | A | Yes | Yes |
| Gm18 | 1695886 | T | A | Yes | Yes |
| Gm18 | 1584541 | A | G | Yes | Yes |
| Gm18 | 1557165 | C | T | Yes | Yes |
| Gm18 | 1630038 | A | G | Yes | Yes |
| Gm18 | 1633840 | G | A | Yes | Yes |
| Gm18 | 1615738 | G | A | Yes | Yes |
| Gm18 | 1633983 | T | C | Yes | Yes |
| Gm18 | 1663907 | C | G | Yes | Yes |
| Gm18 | 1617696 | A | G | Yes | Yes |
| Gm18 | 1736136 | T | C | Yes | Yes |

TABLE 2-continued

| #CHROM | POS | REF | ALT | Peking | PI88788 |
|---|---|---|---|---|---|
| Gm18 | 1641208 | G | A | Yes | Yes |
| Gm18 | 1573317 | A | G | Yes | Yes |
| Gm18 | 1694129 | C | A | Yes | Yes |
| Gm18 | 1635553 | C | G | Yes | Yes |
| Gm18 | 1682250 | T | C | Yes | Yes |
| Gm18 | 1597865 | A | T | Yes | Yes |
| Gm18 | 1601551 | A | T | Yes | Yes |
| Gm18 | 1682082 | A | G | Yes | Yes |
| Gm18 | 1515595 | A | G | Yes | Yes |
| Gm18 | 1681789 | T | C | Yes | Yes |
| Gm18 | 1737550 | A | C | Yes | Yes |
| Gm18 | 1617770 | C | T | Yes | Yes |
| Gm18 | 1710334 | A | T | Yes | Yes |
| Gm18 | 1662755 | A | G | Yes | Yes |
| Gm18 | 1628083 | A | T | Yes | Yes |
| Gm18 | 1663051 | G | A | Yes | Yes |
| Gm18 | 1580305 | C | T | Yes | Yes |
| Gm18 | 1682035 | A | G | Yes | Yes |
| Gm18 | 1681786 | T | C | Yes | Yes |
| Gm18 | 1712832 | T | C | Yes | Yes |
| Gm18 | 1624435 | T | C | Yes | Yes |
| Gm18 | 1681523 | A | G | Yes | Yes |
| Gm18 | 1597206 | A | T | Yes | Yes |
| Gm18 | 1626749 | A | T | Yes | Yes |
| Gm18 | 1616538 | T | C | Yes | Yes |
| Gm18 | 1634118 | G | A | Yes | Yes |
| Gm18 | 1582363 | C | T | Yes | Yes |
| Gm18 | 1662894 | A | G | Yes | Yes |
| Gm18 | 1582357 | G | A | Yes | Yes |
| Gm18 | 1634974 | A | G | Yes | Yes |
| Gm18 | 1514385 | G | A | Yes | Yes |
| Gm18 | 1737519 | G | A | Yes | Yes |
| Gm18 | 1622766 | T | A | Yes | Yes |
| Gm18 | 1640292 | C | A | Yes | Yes |
| Gm18 | 1712691 | A | C | Yes | Yes |
| Gm18 | 1732766 | T | A | Yes | Yes |
| Gm18 | 1684013 | C | A | Yes | Yes |
| Gm18 | 1774737 | A | T, C | Yes | Yes |
| Gm18 | 1663143 | A | G | Yes | Yes |
| Gm18 | 1674972 | C | T | Yes | Yes |
| Gm18 | 1567332 | A | C | Yes | Yes |
| Gm18 | 1628315 | T | C | Yes | Yes |
| Gm18 | 1578714 | A | G | Yes | Yes |
| Gm18 | 1772453 | A | G | Yes | Yes |
| Gm18 | 1687196 | G | T | Yes | Yes |
| Gm18 | 1635378 | C | T | Yes | Yes |
| Gm18 | 1683953 | A | G | Yes | Yes |
| Gm18 | 1623482 | A | G | Yes | Yes |
| Gm18 | 1577205 | A | C | Yes | Yes |
| Gm18 | 1587173 | C | T | Yes | Yes |
| Gm18 | 1583431 | G | C | Yes | Yes |
| Gm18 | 1707243 | C | A | Yes | Yes |
| Gm18 | 1616691 | G | A | Yes | Yes |
| Gm18 | 1698859 | T | A | Yes | Yes |
| Gm18 | 1607885 | C | T | Yes | Yes |
| Gm18 | 1589780 | A | T | Yes | Yes |
| Gm18 | 1606158 | G | C | Yes | Yes |
| Gm18 | 1627607 | A | C | Yes | Yes |
| Gm18 | 1712035 | A | C | Yes | Yes |
| Gm18 | 1678648 | C | T | Yes | Yes |
| Gm18 | 1560517 | G | A | Yes | Yes |
| Gm18 | 1547327 | T | C | Yes | Yes |
| Gm18 | 1634907 | A | T | Yes | Yes |
| Gm18 | 1677749 | C | G | Yes | Yes |
| Gm18 | 1661259 | C | G | Yes | Yes |
| Gm18 | 1582351 | A | G | Yes | Yes |
| Gm18 | 1652253 | A | C | Yes | Yes |
| Gm18 | 1547718 | T | C | Yes | Yes |
| Gm18 | 1709679 | A | T | Yes | Yes |
| Gm18 | 1563924 | G | T | Yes | Yes |
| Gm18 | 1681852 | T | C | Yes | Yes |
| Gm18 | 1622152 | T | A | Yes | Yes |
| Gm18 | 1583859 | G | T | Yes | Yes |
| Gm18 | 1640137 | A | C | Yes | Yes |
| Gm18 | 1622144 | C | T | Yes | Yes |
| Gm18 | 1713907 | A | G | Yes | Yes |
| Gm18 | 1634260 | C | T | Yes | Yes |
| Gm18 | 1762238 | T | C | Yes | Yes |
| Gm18 | 1635093 | A | G | Yes | Yes |
| Gm18 | 1679658 | C | G | Yes | Yes |
| Gm18 | 1617198 | A | G | Yes | Yes |
| Gm18 | 1573060 | C | G | Yes | Yes |
| Gm18 | 1556663 | A | G | Yes | Yes |
| Gm18 | 1661239 | T | C | Yes | Yes |
| Gm18 | 1707415 | C | A | Yes | Yes |
| Gm18 | 1733374 | T | C | Yes | Yes |
| Gm18 | 1577661 | T | C | Yes | Yes |
| Gm18 | 1733491 | A | T | Yes | Yes |
| Gm18 | 1733561 | A | G | Yes | Yes |
| Gm18 | 1600951 | C | T | Yes | Yes |
| Gm18 | 1587518 | C | T | Yes | Yes |
| Gm18 | 1713576 | A | G | Yes | Yes |
| Gm18 | 1675064 | G | A | Yes | Yes |
| Gm18 | 1662694 | T | C, G | Yes | Yes |
| Gm18 | 1739680 | C | G | Yes | Yes |
| Gm18 | 1662810 | G | A | Yes | Yes |
| Gm18 | 1629986 | G | A | Yes | Yes |
| Gm18 | 1694779 | G | A | Yes | Yes |
| Gm18 | 1734669 | G | T | Yes | Yes |
| Gm18 | 1752663 | C | G | Yes | Yes |
| Gm18 | 1578154 | T | C | Yes | Yes |
| Gm18 | 1739797 | A | T | Yes | Yes |
| Gm18 | 1611303 | A | G | Yes | Yes |
| Gm18 | 1598160 | G | A | Yes | Yes |
| Gm18 | 1618456 | C | T | Yes | Yes |
| Gm18 | 1663731 | C | A | Yes | Yes |
| Gm18 | 1663298 | A | G | Yes | Yes |
| Gm18 | 1567602 | A | G | Yes | Yes |
| Gm18 | 1686008 | T | C | Yes | Yes |
| Gm18 | 1652723 | T | C | Yes | Yes |
| Gm18 | 1640151 | G | T | Yes | Yes |
| Gm18 | 1687035 | C | T | Yes | Yes |
| Gm18 | 1709802 | A | T | Yes | Yes |
| Gm18 | 1604611 | C | G | Yes | Yes |
| Gm18 | 1631156 | G | C | Yes | Yes |
| Gm18 | 1635001 | C | T | Yes | Yes |
| Gm18 | 1697427 | C | T | Yes | Yes |
| Gm18 | 1661128 | A | G | Yes | Yes |
| Gm18 | 1716159 | C | T | Yes | Yes |
| Gm18 | 1582843 | A | G | Yes | Yes |
| Gm18 | 1628644 | A | C | Yes | Yes |
| Gm18 | 1745955 | C | G | Yes | Yes |
| Gm18 | 1685024 | A | G | Yes | Yes |
| Gm18 | 1710068 | G | A | Yes | Yes |
| Gm18 | 1582860 | G | A | Yes | Yes |
| Gm18 | 1708735 | G | C | Yes | Yes |
| Gm18 | 1662970 | T | C | Yes | Yes |
| Gm18 | 1745545 | T | C | Yes | Yes |
| Gm18 | 1611422 | G | A | Yes | Yes |
| Gm18 | 1686939 | G | A | Yes | Yes |
| Gm18 | 1634620 | G | A | Yes | Yes |
| Gm18 | 1607624 | A | G | Yes | Yes |
| Gm18 | 1670786 | T | C | Yes | Yes |
| Gm18 | 1766605 | T | C | Yes | Yes |
| Gm18 | 1687192 | A | T | Yes | Yes |
| Gm18 | 1589020 | A | T | Yes | Yes |
| Gm18 | 1515631 | C | A | Yes | Yes |
| Gm18 | 1584144 | T | A | Yes | Yes |
| Gm18 | 1712751 | T | C | Yes | Yes |
| Gm18 | 1559659 | G | A | Yes | Yes |
| Gm18 | 1675070 | G | A | Yes | Yes |
| Gm18 | 1623183 | C | T | Yes | Yes |
| Gm18 | 1664115 | G | A | Yes | Yes |
| Gm18 | 1694637 | T | A | Yes | Yes |
| Gm18 | 1627783 | G | A | Yes | Yes |
| Gm18 | 1547820 | A | C | Yes | Yes |
| Gm18 | 1677584 | G | A | Yes | Yes |
| Gm18 | 1567986 | A | T | Yes | Yes |
| Gm18 | 1627489 | T | A | Yes | Yes |
| Gm18 | 1693992 | C | G | Yes | Yes |
| Gm18 | 1615940 | C | T | Yes | Yes |
| Gm18 | 1690566 | A | G | Yes | Yes |
| Gm18 | 1661088 | A | G | Yes | Yes |
| Gm18 | 1713030 | A | G | Yes | Yes |
| Gm18 | 1758565 | A | C | Yes | Yes |
| Gm18 | 1661104 | T | C | Yes | Yes |

TABLE 2-continued

| #CHROM | POS | REF | ALT | Peking | PI88788 |
|---|---|---|---|---|---|
| Gm18 | 1576682 | G | T | Yes | Yes |
| Gm18 | 1629930 | T | C | Yes | Yes |
| Gm18 | 1634626 | G | A | Yes | Yes |
| Gm18 | 1709893 | G | A | Yes | Yes |
| Gm18 | 1616511 | T | C | Yes | Yes |
| Gm18 | 1683849 | G | A | Yes | Yes |
| Gm18 | 1623157 | T | A | Yes | Yes |
| Gm18 | 1754980 | C | A | Yes | Yes |
| Gm18 | 1615882 | A | G | Yes | Yes |
| Gm18 | 1767968 | T | C | Yes | Yes |
| Gm18 | 1753786 | A | C | Yes | Yes |
| Gm18 | 1725443 | G | C | Yes | Yes |
| Gm18 | 1725460 | A | C | Yes | Yes |
| Gm18 | 1598339 | G | T | Yes | Yes |
| Gm18 | 1679368 | C | G | Yes | Yes |
| Gm18 | 1772255 | C | T | Yes | Yes |
| Gm18 | 1772222 | G | C | Yes | Yes |
| Gm18 | 1703814 | T | G | Yes | Yes |
| Gm18 | 1651950 | A | C | Yes | Yes |
| Gm18 | 1652011 | C | A | Yes | Yes |
| Gm18 | 1622659 | A | T | Yes | Yes |
| Gm18 | 1681897 | G | A | Yes | Yes |
| Gm18 | 1712103 | T | C | Yes | Yes |
| Gm18 | 1662935 | T | C | Yes | Yes |
| Gm18 | 1663250 | G | A | Yes | Yes |
| Gm18 | 1751218 | G | A | Yes | Yes |
| Gm18 | 1690472 | C | G | Yes | Yes |
| Gm18 | 1755475 | C | A | Yes | Yes |
| Gm18 | 1755033 | T | C | Yes | Yes |
| Gm18 | 1612760 | T | A | Yes | Yes |
| Gm18 | 1753857 | G | A | Yes | Yes |
| Gm18 | 1757955 | T | C | Yes | Yes |
| Gm18 | 1737465 | T | C | Yes | Yes |
| Gm18 | 1571274 | T | C | No | Yes |
| Gm18 | 1693079 | A | G | No | Yes |
| Gm18 | 1567327 | G | A | No | Yes |
| Gm18 | 1691381 | A | G | No | Yes |
| Gm18 | 1613850 | T | A | No | Yes |
| Gm18 | 1752445 | A | G | No | Yes |
| Gm18 | 1710853 | A | T | No | Yes |
| Gm18 | 1719339 | C | A | No | Yes |
| Gm18 | 1616566 | G | A | Yes | Yes |
| Gm18 | 1578462 | A | G | No | Yes |
| Gm18 | 1565457 | T | G | No | Yes |
| Gm18 | 1740769 | A | G | No | Yes |
| Gm18 | 1759101 | C | T | No | Yes |
| Gm18 | 1583949 | A | G | No | Yes |
| Gm18 | 1696534 | G | A | No | Yes |
| Gm18 | 1737883 | C | T | No | Yes |
| Gm18 | 1749495 | A | G | No | Yes |
| Gm18 | 1719159 | A | T | No | Yes |
| Gm18 | 1609752 | G | C | No | Yes |
| Gm18 | 1761478 | G | A | No | Yes |
| Gm18 | 1605226 | C | A | No | Yes |
| Gm18 | 1763650 | C | T | No | Yes |
| Gm18 | 1708722 | C | T | No | Yes |
| Gm18 | 1763643 | T | C | No | Yes |
| Gm18 | 1718688 | T | C | No | Yes |
| Gm18 | 1616062 | T | G | No | Yes |
| Gm18 | 1651977 | A | T | Yes | Yes |
| Gm18 | 1697857 | C | T | No | Yes |
| Gm18 | 1735740 | G | T | No | Yes |
| Gm18 | 1735487 | G | A | No | Yes |
| Gm18 | 1748982 | T | C | No | Yes |
| Gm18 | 1573328 | G | C | No | Yes |
| Gm18 | 1607666 | G | A | No | Yes |
| Gm18 | 1559603 | C | T | No | Yes |
| Gm18 | 1716038 | C | T | No | Yes |
| Gm18 | 1696266 | G | A | No | Yes |
| Gm18 | 1608370 | G | T | No | Yes |
| Gm18 | 1696077 | G | C | No | Yes |
| Gm18 | 1671483 | A | G | No | Yes |
| Gm18 | 1739504 | T | G | No | Yes |
| Gm18 | 1740018 | T | A | No | Yes |
| Gm18 | 1574247 | A | T | No | Yes |
| Gm18 | 1608832 | A | G | No | Yes |
| Gm18 | 1690011 | G | T | No | Yes |
| Gm18 | 1683126 | A | G | No | Yes |
| Gm18 | 1698255 | A | G | No | Yes |
| Gm18 | 1703298 | T | C | No | Yes |
| Gm18 | 1513861 | T | A | No | Yes |
| Gm18 | 1694688 | C | G | No | Yes |
| Gm18 | 1694436 | T | C | No | Yes |
| Gm18 | 1749291 | C | G | No | Yes |
| Gm18 | 1565592 | G | T | No | Yes |
| Gm18 | 1693180 | G | A | No | Yes |
| Gm18 | 1701212 | C | T | No | Yes |
| Gm18 | 1772998 | C | A | No | Yes |
| Gm18 | 1568478 | G | C | No | Yes |
| Gm18 | 1715380 | A | T | No | Yes |
| Gm18 | 1726316 | T | G | No | Yes |
| Gm18 | 1759258 | T | C | No | Yes |
| Gm18 | 1686081 | A | G | No | Yes |
| Gm18 | 1696369 | G | A | No | Yes |
| Gm18 | 1746679 | A | G | No | Yes |
| Gm18 | 1696473 | G | C | No | Yes |
| Gm18 | 1767466 | G | C | No | Yes |
| Gm18 | 1749394 | T | A | No | Yes |
| Gm18 | 1603821 | C | G | No | Yes |
| Gm18 | 1751476 | C | T | No | Yes |
| Gm18 | 1701594 | C | T | No | Yes |
| Gm18 | 1663724 | G | A | No | Yes |
| Gm18 | 1603800 | A | G | No | Yes |
| Gm18 | 1691866 | C | G | No | Yes |
| Gm18 | 1603653 | A | G | No | Yes |
| Gm18 | 1767437 | T | C | No | Yes |
| Gm18 | 1757019 | A | G | No | Yes |
| Gm18 | 1710506 | A | G | No | Yes |
| Gm18 | 1597089 | C | A | Yes | Yes |
| Gm18 | 1767783 | T | C | No | Yes |
| Gm18 | 1751428 | A | G | No | Yes |
| Gm18 | 1639379 | C | T | Yes | Yes |
| Gm18 | 1625454 | G | A | Yes | Yes |
| Gm18 | 1699011 | T | C | No | Yes |
| Gm18 | 1604559 | A | G | No | Yes |
| Gm18 | 1601036 | T | G | Yes | Yes |
| Gm18 | 1611740 | A | T | Yes | Yes |
| Gm18 | 1745621 | C | T | No | Yes |
| Gm18 | 1623426 | C | T | Yes | Yes |
| Gm18 | 1761511 | A | T | Yes | Yes |
| Gm18 | 1701944 | T | C | Yes | Yes |
| Gm18 | 1585332 | T | G | Yes | Yes |
| Gm18 | 1587141 | G | T | Yes | Yes |
| Gm18 | 1684856 | T | A | No | Yes |
| Gm18 | 1607524 | A | C | No | Yes |
| Gm18 | 1587643 | G | T | Yes | Yes |
| Gm18 | 1747560 | T | G | Yes | Yes |
| Gm18 | 1739095 | G | A | Yes | Yes |
| Gm18 | 1739077 | C | G | Yes | Yes |
| Gm18 | 1600980 | C | T | No | Yes |
| Gm18 | 1717706 | G | A | Yes | Yes |
| Gm18 | 1629894 | C | T | Yes | Yes |
| Gm18 | 1772204 | A | G | Yes | Yes |
| Gm18 | 1563541 | A | G | Yes | Yes |
| Gm18 | 1696180 | C | T | No | Yes |
| Gm18 | 1696950 | T | C | Yes | Yes |
| Gm18 | 1659777 | C | T | Yes | Yes |
| Gm18 | 1628760 | T | C | Yes | Yes |
| Gm18 | 1571487 | T | C | Yes | Yes |
| Gm18 | 1678883 | G | C | No | Yes |
| Gm18 | 1558913 | A | G | No | Yes |
| Gm18 | 1734249 | A | T | Yes | Yes |
| Gm18 | 1695342 | G | T | No | Yes |
| Gm18 | 1627637 | A | G | Yes | Yes |
| Gm18 | 1629751 | C | T | Yes | Yes |
| Gm18 | 1673096 | T | G | Yes | Yes |
| Gm18 | 1558334 | T | G | No | Yes |
| Gm18 | 1701338 | A | G | No | Yes |
| Gm18 | 1755499 | C | T | No | Yes |
| Gm18 | 1716152 | A | G | No | Yes |
| Gm18 | 1748909 | A | T | No | Yes |
| Gm18 | 1646211 | T | A | Yes | Yes |
| Gm18 | 1740029 | G | C | No | Yes |
| Gm18 | 1738846 | C | T | Yes | Yes |
| Gm18 | 1774322 | G | T | No | Yes |
| Gm18 | 1600945 | T | C | Yes | Yes |

TABLE 2-continued

| #CHROM | POS | REF | ALT | Peking | PI88788 |
|---|---|---|---|---|---|
| Gm18 | 1718972 | G | T | No | Yes |
| Gm18 | 1583764 | C | A | Yes | Yes |
| Gm18 | 1686815 | G | T | Yes | Yes |
| Gm18 | 1586097 | T | A | Yes | Yes |
| Gm18 | 1749616 | T | A | Yes | Yes |
| Gm18 | 1745477 | T | C | No | Yes |
| Gm18 | 1691773 | G | A | No | Yes |
| Gm18 | 1617005 | A | G | No | Yes |
| Gm18 | 1731486 | T | C | Yes | Yes |
| Gm18 | 1729770 | A | G | Yes | Yes |
| Gm18 | 1597188 | T | A | Yes | Yes |
| Gm18 | 1611710 | G | T | Yes | Yes |
| Gm18 | 1597307 | C | T | Yes | Yes |
| Gm18 | 1707154 | A | G | Yes | Yes |
| Gm18 | 1753536 | T | C | No | Yes |
| Gm18 | 1685464 | A | T | Yes | Yes |
| Gm18 | 1712512 | C | A | No | Yes |
| Gm18 | 1603584 | G | A | No | Yes |
| Gm18 | 1737864 | C | A | Yes | Yes |
| Gm18 | 1755392 | G | C | Yes | Yes |
| Gm18 | 1697683 | C | T | No | Yes |
| Gm18 | 1698898 | C | T | No | Yes |
| Gm18 | 1664567 | A | T | Yes | Yes |
| Gm18 | 1603220 | C | T | No | Yes |
| Gm18 | 1690438 | G | A | No | Yes |
| Gm18 | 1616174 | T | C | Yes | Yes |
| Gm18 | 1661328 | T | C | Yes | Yes |
| Gm18 | 1651056 | G | A | Yes | Yes |
| Gm18 | 1603778 | T | C | Yes | Yes |
| Gm18 | 1692400 | G | A | Yes | Yes |
| Gm18 | 1648850 | C | T | Yes | Yes |
| Gm18 | 1736100 | A | C | Yes | Yes |
| Gm18 | 1631761 | G | T | Yes | Yes |
| Gm18 | 1715338 | C | A | Yes | Yes |
| Gm18 | 1628651 | T | A | Yes | Yes |
| Gm18 | 1625573 | G | A | Yes | Yes |
| Gm18 | 1603713 | A | G | Yes | Yes |
| Gm18 | 1761449 | C | T | No | Yes |
| Gm18 | 1661356 | A | G | Yes | Yes |
| Gm18 | 1608702 | T | A | No | Yes |
| Gm18 | 1748303 | A | G | No | Yes |
| Gm18 | 1683857 | A | G | Yes | Yes |
| Gm18 | 1772471 | T | C | Yes | Yes |
| Gm18 | 1688738 | A | T | No | Yes |
| Gm18 | 1703225 | A | G | No | Yes |
| Gm18 | 1713308 | G | C | No | Yes |
| Gm18 | 1755935 | T | G | Yes | Yes |
| Gm18 | 1597320 | T | C | Yes | Yes |
| Gm18 | 1612017 | G | A | No | Yes |
| Gm18 | 1700809 | T | C | No | Yes |
| Gm18 | 1656979 | G | A | Yes | Yes |
| Gm18 | 1599788 | C | T | Yes | Yes |
| Gm18 | 1520606 | C | A | Yes | Yes |
| Gm18 | 1700633 | T | C | Yes | Yes |
| Gm18 | 1746656 | C | G | No | Yes |
| Gm18 | 1622131 | G | A | Yes | Yes |
| Gm18 | 1746362 | A | G | No | Yes |
| Gm18 | 1697657 | T | A | No | Yes |
| Gm18 | 1716072 | G | C | No | Yes |
| Gm18 | 1565451 | C | T | No | Yes |
| Gm18 | 1673499 | C | T | No | Yes |
| Gm18 | 1624123 | G | A | Yes | Yes |
| Gm18 | 1701279 | C | T | No | Yes |
| Gm18 | 1625788 | C | T | Yes | Yes |
| Gm18 | 1726582 | T | C | Yes | Yes |
| Gm18 | 1581602 | T | C | Yes | Yes |
| Gm18 | 1689381 | T | C | No | Yes |
| Gm18 | 1772437 | A | G | Yes | Yes |
| Gm18 | 1629940 | A | T | No | Yes |
| Gm18 | 1718590 | G | C | Yes | Yes |
| Gm18 | 1646019 | C | G | Yes | Yes |
| Gm18 | 1686303 | C | T | Yes | Yes |
| Gm18 | 1716309 | C | A | No | Yes |
| Gm18 | 1566550 | G | C | No | Yes |
| Gm18 | 1750655 | C | T | Yes | Yes |
| Gm18 | 1768802 | G | A | No | Yes |
| Gm18 | 1625527 | T | C | Yes | Yes |
| Gm18 | 1620813 | T | G | Yes | Yes |
| Gm18 | 1673273 | A | T | No | Yes |
| Gm18 | 1745785 | G | A | No | Yes |
| Gm18 | 1698627 | T | C | No | Yes |
| Gm18 | 1597566 | A | T | Yes | Yes |
| Gm18 | 1698566 | A | G | No | Yes |
| Gm18 | 1754069 | C | T | No | Yes |
| Gm18 | 1772404 | T | C | Yes | Yes |
| Gm18 | 1631449 | C | T | Yes | Yes |
| Gm18 | 1626278 | G | A | Yes | Yes |
| Gm18 | 1718002 | G | A | No | Yes |
| Gm18 | 1584054 | A | G | Yes | No |
| Gm18 | 1620585 | T | C | Yes | Yes |
| Gm18 | 1663032 | G | A | Yes | Yes |
| Gm18 | 1740267 | T | C | No | Yes |
| Gm18 | 1662953 | G | A | Yes | Yes |
| Gm18 | 1585543 | G | A | Yes | Yes |
| Gm18 | 1615684 | T | G | Yes | Yes |
| Gm18 | 1701321 | T | C | No | Yes |
| Gm18 | 1748829 | G | C | No | Yes |
| Gm18 | 1594426 | A | G | Yes | Yes |
| Gm18 | 1751985 | C | G | No | Yes |
| Gm18 | 1655195 | C | T | Yes | Yes |
| Gm18 | 1705619 | T | A | No | Yes |
| Gm18 | 1755105 | A | G | Yes | Yes |
| Gm18 | 1663534 | G | A | No | Yes |
| Gm18 | 1679306 | C | T | Yes | Yes |
| Gm18 | 1752225 | T | C | No | Yes |
| Gm18 | 1759124 | A | G | No | Yes |
| Gm18 | 1634714 | A | G | No | Yes |
| Gm18 | 1625677 | T | C | Yes | Yes |
| Gm18 | 1668348 | A | T | No | Yes |
| Gm18 | 1705293 | T | C | No | Yes |
| Gm18 | 1694764 | T | G | No | Yes |
| Gm18 | 1597599 | T | A | Yes | Yes |
| Gm18 | 1603952 | G | A | No | Yes |
| Gm18 | 1599306 | T | C | No | Yes |
| Gm18 | 1518036 | T | G | Yes | No |
| Gm18 | 1597531 | G | C | Yes | Yes |
| Gm18 | 1696238 | T | G | No | Yes |
| Gm18 | 1745863 | G | A | No | Yes |
| Gm18 | 1578538 | T | C | No | Yes |
| Gm18 | 1639658 | T | C | Yes | Yes |
| Gm18 | 1704849 | C | T | No | Yes |
| Gm18 | 1582739 | A | G | No | Yes |
| Gm18 | 1704867 | A | G | No | Yes |
| Gm18 | 1545114 | A | G | Yes | No |
| Gm18 | 1705325 | A | G | No | Yes |
| Gm18 | 1703153 | T | C | No | Yes |
| Gm18 | 1567685 | C | T | Yes | No |
| Gm18 | 1547096 | C | T | No | Yes |
| Gm18 | 1547940 | A | C | Yes | Yes |
| Gm18 | 1700832 | C | T | Yes | Yes |
| Gm18 | 1686599 | A | T | Yes | Yes |
| Gm18 | 1673454 | C | T | No | Yes |
| Gm18 | 1510450 | A | T | Yes | No |
| Gm18 | 1562453 | C | T | No | Yes |
| Gm18 | 1692534 | A | C | Yes | Yes |
| Gm18 | 1685811 | C | G | Yes | Yes |
| Gm18 | 1612354 | A | G | No | Yes |
| Gm18 | 1678526 | T | A | Yes | Yes |
| Gm18 | 1707433 | G | T | No | Yes |
| Gm18 | 1696737 | C | T | No | Yes |
| Gm18 | 1695572 | G | T | No | Yes |
| Gm18 | 1658617 | A | G | Yes | Yes |
| Gm18 | 1577708 | G | C | Yes | Yes |
| Gm18 | 1515878 | C | T | Yes | Yes |
| Gm18 | 1701304 | T | C | No | Yes |
| Gm18 | 1562162 | G | A | Yes | No |
| Gm18 | 1663620 | T | C | Yes | Yes |
| Gm18 | 1690868 | A | G | Yes | Yes |
| Gm18 | 1600193 | T | C | Yes | Yes |
| Gm18 | 1650201 | G | A | Yes | Yes |
| Gm18 | 1746695 | G | C | Yes | Yes |
| Gm18 | 1604259 | G | A | No | Yes |
| Gm18 | 1689722 | C | G | No | Yes |
| Gm18 | 1612360 | A | C | No | Yes |
| Gm18 | 1710944 | C | T | Yes | Yes |
| Gm18 | 1611666 | A | G | Yes | Yes |

TABLE 2-continued

| #CHROM | POS | REF | ALT | Peking | PI88788 |
|---|---|---|---|---|---|
| Gm18 | 1576719 | G | A | No | Yes |
| Gm18 | 1560860 | C | T | No | Yes |
| Gm18 | 1567133 | G | A | Yes | Yes |
| Gm18 | 1603723 | C | G | No | Yes |
| Gm18 | 1619991 | A | C | Yes | Yes |
| Gm18 | 1767892 | T | A | No | Yes |
| Gm18 | 1567183 | C | T | Yes | Yes |
| Gm18 | 1676732 | T | A | Yes | Yes |
| Gm18 | 1753603 | A | C | No | Yes |
| Gm18 | 1716247 | G | A | No | Yes |
| Gm18 | 1681023 | T | G | Yes | No |
| Gm18 | 1693474 | T | A | No | Yes |
| Gm18 | 1516891 | G | A | Yes | No |
| Gm18 | 1719027 | T | C | No | Yes |
| Gm18 | 1604867 | A | C | No | Yes |
| Gm18 | 1687349 | G | A | Yes | Yes |
| Gm18 | 1684975 | C | T | Yes | No |
| Gm18 | 1514879 | C | A | Yes | No |
| Gm18 | 1698112 | T | A | No | Yes |
| Gm18 | 1606360 | C | T | No | Yes |
| Gm18 | 1702096 | T | C | Yes | Yes |
| Gm18 | 1727375 | C | T | No | Yes |
| Gm18 | 1661293 | G | A | Yes | Yes |
| Gm18 | 1612060 | T | G | Yes | Yes |
| Gm18 | 1712907 | T | C | No | Yes |
| Gm18 | 1714901 | G | A | No | Yes |
| Gm18 | 1704995 | A | T | No | Yes |
| Gm18 | 1604206 | C | T | Yes | Yes |
| Gm18 | 1604186 | T | C | Yes | Yes |
| Gm18 | 1676730 | C | A | Yes | Yes |
| Gm18 | 1609704 | T | G | Yes | Yes |
| Gm18 | 1731725 | T | C | Yes | No |
| Gm18 | 1627802 | G | A | Yes | Yes |
| Gm18 | 1659914 | G | A | Yes | Yes |
| Gm18 | 1753820 | A | G | Yes | Yes |
| Gm18 | 1604236 | C | T | No | Yes |
| Gm18 | 1761960 | C | A | No | Yes |
| Gm18 | 1645582 | G | C | Yes | Yes |
| Gm18 | 1577745 | C | A | Yes | Yes |
| Gm18 | 1698888 | A | T | No | Yes |
| Gm18 | 1704228 | G | T | Yes | Yes |
| Gm18 | 1605467 | G | A | No | Yes |
| Gm18 | 1707668 | C | T | Yes | Yes |
| Gm18 | 1627079 | G | T | Yes | Yes |
| Gm18 | 1594961 | G | T | No | Yes |
| Gm18 | 1567679 | T | C | No | Yes |
| Gm18 | 1750622 | C | T | No | Yes |
| Gm18 | 1663568 | A | G | Yes | Yes |
| Gm18 | 1604054 | G | A | No | Yes |
| Gm18 | 1604478 | C | T | No | Yes |
| Gm18 | 1726584 | A | G | No | Yes |
| Gm18 | 1626935 | A | T | Yes | Yes |
| Gm18 | 1693038 | C | T | Yes | Yes |
| Gm18 | 1761727 | C | T | No | Yes |
| Gm18 | 1680414 | C | T | No | Yes |
| Gm18 | 1552799 | C | A | Yes | No |
| Gm18 | 1734544 | T | C | Yes | Yes |
| Gm18 | 1626400 | A | C | Yes | Yes |
| Gm18 | 1755415 | C | G | Yes | Yes |
| Gm18 | 1604307 | G | A | No | Yes |
| Gm18 | 1597401 | C | T | No | Yes |
| Gm18 | 1704096 | C | T | Yes | Yes |
| Gm18 | 1737706 | A | C | No | Yes |
| Gm18 | 1649934 | G | A | Yes | No |
| Gm18 | 1761957 | G | A | No | Yes |
| Gm18 | 1568634 | T | A | No | Yes |
| Gm18 | 1690926 | G | A | No | Yes |
| Gm18 | 1639656 | G | A | Yes | Yes |
| Gm18 | 1766218 | C | G | Yes | Yes |
| Gm18 | 1726637 | G | A | No | Yes |
| Gm18 | 1568509 | A | C | No | Yes |
| Gm18 | 1626216 | T | C | Yes | Yes |
| Gm18 | 1734457 | T | G | Yes | Yes |
| Gm18 | 1656263 | G | C | Yes | Yes |
| Gm18 | 1567931 | A | G | No | Yes |
| Gm18 | 1701969 | G | T | Yes | Yes |
| Gm18 | 1738049 | A | G | No | Yes |
| Gm18 | 1599720 | C | G | No | Yes |
| Gm18 | 1701818 | T | C | No | Yes |
| Gm18 | 1572384 | G | T | No | Yes |
| Gm18 | 1750742 | G | A | Yes | Yes |
| Gm18 | 1577669 | T | G | Yes | Yes |
| Gm18 | 1692117 | G | A | Yes | Yes |
| Gm18 | 1716282 | G | C | No | Yes |
| Gm18 | 1714211 | T | C | No | Yes |
| Gm18 | 1750557 | C | T | No | Yes |
| Gm18 | 1581762 | T | C | No | Yes |
| Gm18 | 1594480 | T | C | No | Yes |
| Gm18 | 1562660 | G | C | No | Yes |
| Gm18 | 1677244 | T | C | Yes | Yes |
| Gm18 | 1708276 | T | C | Yes | Yes |
| Gm18 | 1667354 | T | C | Yes | No |
| Gm18 | 1707358 | G | T | Yes | Yes |
| Gm18 | 1742720 | G | A | No | Yes |
| Gm18 | 1711952 | T | C | Yes | No |
| Gm18 | 1716080 | C | T | No | Yes |
| Gm18 | 1563768 | A | C | No | Yes |
| Gm18 | 1762265 | G | A | No | Yes |
| Gm18 | 1567642 | T | A | No | Yes |
| Gm18 | 1602219 | G | T | No | Yes |
| Gm18 | 1655836 | T | C | Yes | Yes |
| Gm18 | 1676145 | A | T | Yes | Yes |
| Gm18 | 1603367 | C | T | No | Yes |
| Gm18 | 1709043 | A | G | Yes | Yes |
| Gm18 | 1760930 | T | C | Yes | Yes |
| Gm18 | 1533800 | A | G | Yes | No |
| Gm18 | 1715191 | G | A | No | Yes |
| Gm18 | 1655585 | A | T | Yes | No |
| Gm18 | 1603794 | G | A | No | Yes |
| Gm18 | 1626263 | T | G | Yes | Yes |
| Gm18 | 1604000 | C | T | No | Yes |
| Gm18 | 1692294 | C | T | Yes | Yes |
| Gm18 | 1676737 | C | T | Yes | Yes |
| Gm18 | 1619793 | A | G | Yes | Yes |
| Gm18 | 1664369 | A | C | Yes | No |
| Gm18 | 1560584 | C | A | No | Yes |
| Gm18 | 1558551 | T | C | Yes | No |
| Gm18 | 1757659 | C | T | No | Yes |
| Gm18 | 1605056 | T | C | Yes | Yes |
| Gm18 | 1718612 | C | A | Yes | Yes |
| Gm18 | 1600162 | C | G | No | Yes |
| Gm18 | 1559787 | A | C | No | Yes |
| Gm18 | 1618051 | A | T | Yes | Yes |
| Gm18 | 1772385 | T | A | No | Yes |
| Gm18 | 1663479 | A | G | Yes | Yes |
| Gm18 | 1734037 | G | T | Yes | Yes |
| Gm18 | 1606094 | C | T | Yes | Yes |
| Gm18 | 1682578 | T | A | Yes | No |
| Gm18 | 1671225 | T | C | No | Yes |
| Gm18 | 1759241 | A | G | No | Yes |
| Gm18 | 1706862 | A | C | No | Yes |
| Gm18 | 1581931 | T | G | No | Yes |
| Gm18 | 1645811 | A | G | Yes | Yes |
| Gm18 | 1665206 | A | T | Yes | Yes |
| Gm18 | 1705027 | T | G | No | Yes |
| Gm18 | 1606777 | G | T | No | Yes |
| Gm18 | 1703606 | C | T | Yes | Yes |
| Gm18 | 1616203 | C | A | Yes | Yes |
| Gm18 | 1761649 | G | A | Yes | Yes |
| Gm18 | 1630475 | C | A | Yes | Yes |
| Gm18 | 1675849 | A | C | No | Yes |
| Gm18 | 1772506 | C | A | No | Yes |
| Gm18 | 1772430 | G | A | No | Yes |
| Gm18 | 1761525 | A | C | Yes | Yes |
| Gm18 | 1705064 | C | T | No | Yes |
| Gm18 | 1716076 | C | T | No | Yes |
| Gm18 | 1567659 | G | A | No | Yes |
| Gm18 | 1585587 | A | G | Yes | Yes |
| Gm18 | 1755633 | A | C | Yes | Yes |
| Gm18 | 1509418 | C | T | Yes | No |
| Gm18 | 1692913 | C | T | No | Yes |
| Gm18 | 1546840 | A | G | No | Yes |
| Gm18 | 1747766 | A | T | Yes | No |
| Gm18 | 1567648 | A | G | No | Yes |
| Gm18 | 1605559 | C | G, T | Yes | Yes |
| Gm18 | 1518071 | T | C | Yes | No |

TABLE 2-continued

| #CHROM | POS | REF | ALT | Peking | PI88788 |
|---|---|---|---|---|---|
| Gm18 | 1515940 | T | A | Yes | Yes |
| Gm18 | 1679942 | G | T | No | Yes |
| Gm18 | 1751117 | T | C | Yes | Yes |
| Gm18 | 1569374 | T | C | Yes | Yes |
| Gm18 | 1618502 | C | T | Yes | No |
| Gm18 | 1583939 | A | T | Yes | Yes |
| Gm18 | 1750705 | A | G | Yes | Yes |
| Gm18 | 1750083 | G | A | No | Yes |
| Gm18 | 1603857 | C | A, G | Yes | Yes |
| Gm18 | 1691500 | C | T | No | Yes |
| Gm18 | 1719055 | G | A | No | Yes |
| Gm18 | 1755101 | T | G | Yes | Yes |
| Gm18 | 1755078 | G | A | Yes | Yes |
| Gm18 | 1629721 | T | A | Yes | Yes |
| Gm18 | 1692085 | C | A | Yes | Yes |
| Gm18 | 1712955 | C | T | No | Yes |
| Gm18 | 1715284 | C | A | No | Yes |
| Gm18 | 1739073 | C | T | Yes | Yes |
| Gm18 | 1517392 | G | T | Yes | No |
| Gm18 | 1750402 | T | G | No | Yes |
| Gm18 | 1565704 | T | G | No | Yes |
| Gm18 | 1761627 | A | G | No | Yes |
| Gm18 | 1595360 | A | G | No | Yes |
| Gm18 | 1769483 | A | T | No | Yes |
| Gm18 | 1683590 | T | C | Yes | No |
| Gm18 | 1688067 | C | T | Yes | No |
| Gm18 | 1627771 | T | G | Yes | Yes |
| Gm18 | 1566793 | T | C | No | Yes |
| Gm18 | 1765893 | G | A | Yes | Yes |
| Gm18 | 1586217 | A | T | Yes | Yes |
| Gm18 | 1751280 | C | A | Yes | Yes |
| Gm18 | 1625548 | G | A | Yes | Yes |
| Gm18 | 1537665 | T | A | Yes | No |
| Gm18 | 1625263 | T | C | Yes | Yes |
| Gm18 | 1724082 | A | G | Yes | No |
| Gm18 | 1604183 | G | A | Yes | No |
| Gm18 | 1768130 | T | A | No | Yes |
| Gm18 | 1604653 | C | T | No | Yes |
| Gm18 | 1565646 | T | G | Yes | No |
| Gm18 | 1750842 | T | C | No | Yes |
| Gm18 | 1661428 | G | A | Yes | Yes |
| Gm18 | 1754530 | G | T | No | Yes |
| Gm18 | 1568214 | A | G | No | Yes |
| Gm18 | 1565225 | G | A | Yes | No |
| Gm18 | 1699266 | A | T | No | Yes |
| Gm18 | 1567665 | C | T | Yes | No |
| Gm18 | 1510523 | T | C | Yes | No |
| Gm18 | 1708391 | C | T | Yes | Yes |
| Gm18 | 1663133 | C | T | Yes | No |
| Gm18 | 1520736 | G | T | Yes | Yes |
| Gm18 | 1660682 | T | A | Yes | Yes |
| Gm18 | 1729347 | T | C | Yes | No |
| Gm18 | 1690921 | T | C | No | Yes |
| Gm18 | 1614447 | G | T | No | Yes |
| Gm18 | 1559970 | T | G | No | Yes |
| Gm18 | 1772369 | C | T | No | Yes |
| Gm18 | 1758544 | G | A | Yes | Yes |
| Gm18 | 1566823 | A | C | Yes | Yes |
| Gm18 | 1639405 | T | A | Yes | Yes |
| Gm18 | 1645759 | T | C | Yes | Yes |
| Gm18 | 1733766 | T | C | No | Yes |
| Gm18 | 1566996 | T | C | Yes | No |
| Gm18 | 1674853 | C | G | Yes | No |
| Gm18 | 1681070 | G | A | Yes | No |
| Gm18 | 1546638 | G | C | No | Yes |
| Gm18 | 1772329 | G | A | Yes | Yes |
| Gm18 | 1566846 | A | G | No | Yes |
| Gm18 | 1662946 | G | T | Yes | Yes |
| Gm18 | 1772418 | T | C | No | Yes |
| Gm18 | 1761624 | G | T | No | Yes |
| Gm18 | 1708283 | T | C | Yes | Yes |
| Gm18 | 1625895 | A | G | Yes | Yes |
| Gm18 | 1713174 | C | T | No | Yes |
| Gm18 | 1769041 | C | A | No | Yes |
| Gm18 | 1706019 | G | A | No | Yes |
| Gm18 | 1663957 | A | T | No | Yes |
| Gm18 | 1654787 | C | T | Yes | No |
| Gm18 | 1757452 | A | C | Yes | Yes |
| Gm18 | 1752933 | A | C | Yes | Yes |
| Gm18 | 1716191 | C | G | No | Yes |
| Gm18 | 1676018 | A | C | Yes | Yes |
| Gm18 | 1759526 | C | A | No | Yes |
| Gm18 | 1644974 | C | A | Yes | No |
| Gm18 | 1767510 | A | G | No | Yes |
| Gm18 | 1737892 | C | T | No | Yes |
| Gm18 | 1719318 | A | G | No | Yes |
| Gm18 | 1603771 | G | C | No | Yes |
| Gm18 | 1685613 | G | T | Yes | No |
| Gm18 | 1567691 | T | G | No | Yes |
| Gm18 | 1649371 | G | A | Yes | No |
| Gm18 | 1750798 | A | G | No | Yes |
| Gm18 | 1708286 | T | C | Yes | Yes |
| Gm18 | 1625409 | T | C | Yes | Yes |
| Gm18 | 1558144 | A | G | Yes | Yes |
| Gm18 | 1521175 | T | G | Yes | No |
| Gm18 | 1759517 | G | A | No | Yes |
| Gm18 | 1604482 | T | A | No | Yes |
| Gm18 | 1705451 | T | G | No | Yes |
| Gm18 | 1684330 | C | T | Yes | No |
| Gm18 | 1577684 | T | C | Yes | Yes |
| Gm18 | 1515987 | A | G | Yes | Yes |
| Gm18 | 1716081 | C | G | No | Yes |
| Gm18 | 1601534 | A | G | Yes | No |
| Gm18 | 1756949 | C | T | No | Yes |
| Gm18 | 1572368 | C | T | Yes | No |
| Gm18 | 1741366 | T | A | No | Yes |
| Gm18 | 1611921 | C | T | Yes | Yes |
| Gm18 | 1680099 | A | G | Yes | Yes |
| Gm18 | 1766246 | C | G | Yes | Yes |
| Gm18 | 1728146 | C | A | Yes | No |
| Gm18 | 1750529 | T | C | No | Yes |
| Gm18 | 1582158 | T | A | No | Yes |
| Gm18 | 1562719 | A | T | Yes | Yes |
| Gm18 | 1663114 | A | G | Yes | No |
| Gm18 | 1650928 | A | T | Yes | Yes |
| Gm18 | 1586334 | A | C | Yes | Yes |
| Gm18 | 1601614 | A | G | Yes | No |
| Gm18 | 1568490 | A | C | Yes | No |
| Gm18 | 1567049 | G | A | No | Yes |
| Gm18 | 1701792 | A | G | No | Yes |
| Gm18 | 1625924 | T | C | Yes | Yes |
| Gm18 | 1625923 | A | G | Yes | Yes |
| Gm18 | 1589032 | C | T | Yes | No |
| Gm18 | 1663007 | T | C | Yes | Yes |
| Gm18 | 1749588 | G | T | No | Yes |
| Gm18 | 1719483 | C | T | Yes | Yes |
| Gm18 | 1566922 | C | T | Yes | Yes |
| Gm18 | 1511934 | T | G | Yes | No |
| Gm18 | 1681782 | G | C | Yes | No |
| Gm18 | 1770509 | A | T | No | Yes |
| Gm18 | 1643324 | C | T | Yes | Yes |
| Gm18 | 1766547 | A | T | Yes | Yes |
| Gm18 | 1656769 | T | G | Yes | Yes |
| Gm18 | 1517146 | G | C | Yes | No |
| Gm18 | 1677273 | T | G | Yes | Yes |
| Gm18 | 1681373 | G | A | Yes | No |
| Gm18 | 1700730 | G | A | Yes | Yes |
| Gm18 | 1757027 | A | C | No | Yes |
| Gm18 | 1531862 | A | T | Yes | No |
| Gm18 | 1684979 | T | G | Yes | No |
| Gm18 | 1511990 | G | A | Yes | No |
| Gm18 | 1679131 | A | G | No | Yes |
| Gm18 | 1742215 | C | T | No | Yes |
| Gm18 | 1629507 | G | T | Yes | Yes |
| Gm18 | 1608498 | A | C | Yes | No |
| Gm18 | 1551459 | A | G | No | Yes |
| Gm18 | 1625660 | C | A | Yes | Yes |
| Gm18 | 1718801 | C | T | No | Yes |
| Gm18 | 1750514 | A | G | No | Yes |
| Gm18 | 1688457 | T | A | No | Yes |
| Gm18 | 1769820 | T | C | No | Yes |
| Gm18 | 1774619 | T | A | No | Yes |
| Gm18 | 1719095 | G | T | No | Yes |
| Gm18 | 1645745 | T | A | Yes | No |
| Gm18 | 1562155 | A | T | Yes | No |
| Gm18 | 1509260 | C | G | Yes | No |

TABLE 2-continued

| #CHROM | POS | REF | ALT | Peking | PI88788 |
|---|---|---|---|---|---|
| Gm18 | 1667481 | A | G | Yes | No |
| Gm18 | 1750271 | T | C | No | Yes |
| Gm18 | 1700835 | T | C | No | Yes |
| Gm18 | 1702208 | G | A | Yes | Yes |
| Gm18 | 1605983 | A | G | Yes | Yes |
| Gm18 | 1751187 | G | C | No | Yes |
| Gm18 | 1602244 | C | G | Yes | No |
| Gm18 | 1605716 | G | A | No | Yes |
| Gm18 | 1568963 | G | A | Yes | Yes |
| Gm18 | 1757449 | G | A | No | Yes |
| Gm18 | 1695383 | T | C | No | Yes |
| Gm18 | 1547174 | T | A | No | Yes |
| Gm18 | 1546699 | G | A | No | Yes |
| Gm18 | 1539580 | A | C | Yes | No |
| Gm18 | 1750508 | T | C | No | Yes |
| Gm18 | 1640581 | C | T | Yes | No |
| Gm18 | 1691759 | G | A | No | Yes |
| Gm18 | 1750274 | G | C | No | Yes |
| Gm18 | 1749539 | T | C | No | Yes |
| Gm18 | 1654687 | G | C | Yes | No |
| Gm18 | 1547286 | T | C | Yes | No |
| Gm18 | 1605349 | A | T | No | Yes |
| Gm18 | 1646148 | G | T | Yes | Yes |
| Gm18 | 1721829 | A | T | Yes | No |
| Gm18 | 1765585 | G | A | Yes | No |
| Gm18 | 1763519 | T | A | Yes | No |
| Gm18 | 1664713 | G | C | Yes | No |
| Gm18 | 1546801 | T | A | Yes | Yes |
| Gm18 | 1620185 | C | A | Yes | Yes |
| Gm18 | 1569395 | G | A | No | Yes |
| Gm18 | 1599686 | T | G | No | Yes |
| Gm18 | 1754035 | T | C | No | Yes |
| Gm18 | 1695131 | C | A | No | Yes |
| Gm18 | 1605389 | C | A | No | Yes |
| Gm18 | 1702044 | C | T | No | Yes |
| Gm18 | 1568826 | A | G | Yes | Yes |
| Gm18 | 1565858 | T | C | Yes | Yes |
| Gm18 | 1599688 | T | C | No | Yes |
| Gm18 | 1576291 | C | T | No | Yes |
| Gm18 | 1600072 | G | C, A | Yes | Yes |
| Gm18 | 1775058 | G | T | No | Yes |
| Gm18 | 1691221 | T | G | Yes | Yes |
| Gm18 | 1612200 | A | T | No | Yes |
| Gm18 | 1584669 | A | G | Yes | Yes |
| Gm18 | 1625658 | C | T | Yes | Yes |
| Gm18 | 1567728 | T | C | No | Yes |
| Gm18 | 1532390 | C | T | Yes | No |
| Gm18 | 1723032 | T | C | Yes | No |
| Gm18 | 1566821 | T | C | No | Yes |
| Gm18 | 1671082 | C | T | Yes | No |
| Gm18 | 1749602 | G | C | No | Yes |
| Gm18 | 1766585 | C | T | No | Yes |
| Gm18 | 1701871 | A | G | No | Yes |
| Gm18 | 1544585 | T | C | Yes | No |
| Gm18 | 1709236 | T | A | Yes | No |
| Gm18 | 1748836 | T | C | No | Yes |
| Gm18 | 1728528 | G | T | No | Yes |
| Gm18 | 1700842 | T | G | No | Yes |
| Gm18 | 1582570 | T | C | Yes | Yes |
| Gm18 | 1523663 | T | G | Yes | No |
| Gm18 | 1770435 | T | A | No | Yes |
| Gm18 | 1719606 | G | C | Yes | Yes |
| Gm18 | 1755274 | C | G | Yes | Yes |
| Gm18 | 1755282 | A | G | Yes | Yes |
| Gm18 | 1715336 | G | A | No | Yes |
| Gm18 | 1566520 | C | T | No | Yes |
| Gm18 | 1662682 | A | G | Yes | No |
| Gm18 | 1569074 | T | C | No | Yes |
| Gm18 | 1649212 | A | C | Yes | Yes |
| Gm18 | 1634453 | G | A | Yes | Yes |
| Gm18 | 1634543 | T | C | Yes | Yes |
| Gm18 | 1577746 | G | A | Yes | Yes |
| Gm18 | 1700722 | G | A | Yes | Yes |
| Gm18 | 1771045 | G | A | Yes | No |
| Gm18 | 1600060 | C | G, A | Yes | Yes |
| Gm18 | 1609397 | C | A | Yes | No |
| Gm18 | 1692517 | T | A | Yes | Yes |
| Gm18 | 1645954 | G | A | Yes | Yes |
| Gm18 | 1762836 | A | C | No | Yes |
| Gm18 | 1692147 | C | T | Yes | Yes |
| Gm18 | 1543865 | G | C | Yes | No |
| Gm18 | 1642236 | T | C | Yes | No |
| Gm18 | 1707377 | T | C | Yes | No |
| Gm18 | 1750037 | A | G | No | Yes |
| Gm18 | 1718659 | G | A | No | Yes |
| Gm18 | 1516270 | A | C | Yes | Yes |
| Gm18 | 1692128 | T | C | Yes | Yes |
| Gm18 | 1599872 | T | C | Yes | Yes |
| Gm18 | 1695415 | G | T | Yes | Yes |
| Gm18 | 1677168 | C | T | Yes | Yes |
| Gm18 | 1585055 | T | A | No | Yes |
| Gm18 | 1606615 | T | C | Yes | Yes |
| Gm18 | 1673470 | A | G | No | Yes |
| Gm18 | 1754518 | G | A | No | Yes |
| Gm18 | 1599907 | A | G | Yes | Yes |
| Gm18 | 1605281 | G | A | No | Yes |
| Gm18 | 1613051 | C | T | Yes | No |
| Gm18 | 1551284 | T | A | Yes | Yes |
| Gm18 | 1512482 | A | C | Yes | No |
| Gm18 | 1625424 | G | A | Yes | Yes |
| Gm18 | 1707759 | T | C | Yes | Yes |
| Gm18 | 1766626 | C | A | No | Yes |
| Gm18 | 1733211 | G | A | Yes | No |
| Gm18 | 1517001 | A | C | Yes | No |
| Gm18 | 1680507 | T | C | Yes | No |
| Gm18 | 1750541 | T | C | No | Yes |
| Gm18 | 1698479 | A | T | Yes | No |
| Gm18 | 1775132 | T | A | Yes | No |
| Gm18 | 1569405 | G | T | No | Yes |
| Gm18 | 1696511 | C | A | Yes | No |
| Gm18 | 1709479 | T | A | Yes | No |
| Gm18 | 1750722 | C | T | No | Yes |
| Gm18 | 1663573 | A | G | No | Yes |
| Gm18 | 1769619 | T | A | Yes | No |
| Gm18 | 1654484 | A | G | Yes | No |
| Gm18 | 1550024 | T | C | Yes | No |
| Gm18 | 1716448 | A | C | No | Yes |
| Gm18 | 1772176 | A | G | Yes | Yes |
| Gm18 | 1727343 | A | C | Yes | No |
| Gm18 | 1598279 | A | C | No | Yes |
| Gm18 | 1757577 | T | G | No | Yes |
| Gm18 | 1670333 | T | A | Yes | No |
| Gm18 | 1691565 | A | G | No | Yes |
| Gm18 | 1625346 | C | T | Yes | Yes |
| Gm18 | 1754005 | T | G | No | Yes |
| Gm18 | 1692151 | C | T | Yes | Yes |
| Gm18 | 1692860 | A | G | No | Yes |
| Gm18 | 1574545 | G | T | No | Yes |
| Gm18 | 1541662 | G | A | Yes | No |
| Gm18 | 1704965 | G | A | No | Yes |
| Gm18 | 1715146 | T | C | Yes | No |
| Gm18 | 1692318 | T | G | Yes | Yes |
| Gm18 | 1567835 | T | G | No | Yes |
| Gm18 | 1655408 | G | A | Yes | No |
| Gm18 | 1598562 | T | G | No | Yes |
| Gm18 | 1699346 | G | A | Yes | Yes |
| Gm18 | 1765117 | G | A | No | Yes |
| Gm18 | 1731068 | G | A | Yes | No |
| Gm18 | 1663148 | A | G | Yes | No |
| Gm18 | 1684542 | T | C | Yes | Yes |
| Gm18 | 1707716 | T | G | Yes | Yes |
| Gm18 | 1733949 | G | A | Yes | Yes |
| Gm18 | 1579270 | A | G | Yes | No |
| Gm18 | 1634452 | T | C | Yes | Yes |
| Gm18 | 1700689 | C | G | No | Yes |
| Gm18 | 1692275 | A | G | Yes | Yes |
| Gm18 | 1605946 | A | G | Yes | Yes |
| Gm18 | 1605965 | A | C | Yes | Yes |
| Gm18 | 1768110 | A | G | No | Yes |
| Gm18 | 1668887 | G | A | Yes | No |
| Gm18 | 1707714 | A | G | Yes | Yes |
| Gm18 | 1605417 | G | A | No | Yes |
| Gm18 | 1750318 | G | A | No | Yes |
| Gm18 | 1521150 | C | T | Yes | No |
| Gm18 | 1750049 | G | A | No | Yes |
| Gm18 | 1567716 | C | T | No | Yes |

TABLE 2-continued

| #CHROM | POS | REF | ALT | Peking | PI88788 |
|---|---|---|---|---|---|
| Gm18 | 1568548 | T | A | No | Yes |
| Gm18 | 1642307 | C | T | Yes | No |
| Gm18 | 1773908 | A | T | Yes | Yes |
| Gm18 | 1707839 | A | C | Yes | Yes |
| Gm18 | 1750766 | C | A | No | Yes |
| Gm18 | 1677210 | A | G | Yes | Yes |
| Gm18 | 1663785 | C | T | Yes | No |
| Gm18 | 1702736 | C | T | No | Yes |
| Gm18 | 1668441 | A | G | Yes | No |
| Gm18 | 1605631 | C | T | No | Yes |
| Gm18 | 1605957 | C | T | Yes | Yes |
| Gm18 | 1605958 | C | T | Yes | Yes |
| Gm18 | 1599684 | G | C | Yes | No |
| Gm18 | 1710295 | A | C | Yes | No |
| Gm18 | 1750099 | G | T | No | Yes |
| Gm18 | 1658170 | T | C | Yes | No |
| Gm18 | 1768783 | C | A | Yes | No |
| Gm18 | 1712967 | C | T | No | Yes |
| Gm18 | 1576881 | C | T | No | Yes |
| Gm18 | 1600084 | T | C | No | Yes |
| Gm18 | 1740118 | C | T | Yes | No |
| Gm18 | 1603741 | T | C | No | Yes |
| Gm18 | 1517895 | C | T | Yes | No |
| Gm18 | 1763183 | G | A | No | Yes |
| Gm18 | 1705929 | A | G | No | Yes |
| Gm18 | 1707866 | G | A | Yes | Yes |
| Gm18 | 1750817 | C | T | No | Yes |
| Gm18 | 1663014 | G | T | Yes | Yes |
| Gm18 | 1560390 | A | C | Yes | No |
| Gm18 | 1542189 | A | G | Yes | No |
| Gm18 | 1728824 | G | A | Yes | No |
| Gm18 | 1689805 | T | C | Yes | No |
| Gm18 | 1700740 | A | G | Yes | Yes |
| Gm18 | 1603750 | T | C | No | Yes |
| Gm18 | 1538040 | C | T | Yes | No |
| Gm18 | 1750890 | A | C | No | Yes |
| Gm18 | 1761318 | T | C | No | Yes |
| Gm18 | 1605853 | C | T | Yes | Yes |
| Gm18 | 1703801 | A | T | Yes | Yes |
| Gm18 | 1701930 | A | C | Yes | Yes |
| Gm18 | 1679739 | T | C | Yes | No |
| Gm18 | 1725630 | G | C | Yes | No |
| Gm18 | 1762610 | T | A | No | Yes |
| Gm18 | 1701700 | A | C | No | Yes |
| Gm18 | 1663486 | G | A | No | Yes |
| Gm18 | 1566446 | G | A | Yes | No |
| Gm18 | 1757980 | T | C | Yes | Yes |
| Gm18 | 1744716 | C | T | No | Yes |
| Gm18 | 1603235 | C | T | No | Yes |
| Gm18 | 1657307 | C | T | Yes | Yes |
| Gm18 | 1765324 | G | A | No | Yes |
| Gm18 | 1709488 | A | T | Yes | No |
| Gm18 | 1751156 | C | T | Yes | No |
| Gm18 | 1707841 | T | G | Yes | Yes |
| Gm18 | 1725815 | G | A | Yes | No |
| Gm18 | 1762541 | N | A | Yes | Yes |
| Gm18 | 1599868 | T | C | Yes | Yes |
| Gm18 | 1736297 | C | T | Yes | Yes |
| Gm18 | 1592850 | T | A | Yes | Yes |
| Gm18 | 1717352 | G | T | Yes | No |
| Gm18 | 1540542 | A | G | Yes | No |
| Gm18 | 1706842 | C | G | Yes | No |
| Gm18 | 1605573 | G | A | No | Yes |
| Gm18 | 1583772 | G | A | Yes | No |
| Gm18 | 1511910 | T | G | Yes | No |
| Gm18 | 1570009 | A | C | Yes | Yes |
| Gm18 | 1700743 | C | T | Yes | Yes |
| Gm18 | 1569093 | A | C | No | Yes |
| Gm18 | 1645908 | T | A | Yes | Yes |
| Gm18 | 1516459 | G | C | Yes | No |
| Gm18 | 1545944 | C | A | Yes | No |
| Gm18 | 1654681 | T | A | Yes | No |
| Gm18 | 1567459 | C | T | No | Yes |
| Gm18 | 1715501 | G | A | Yes | No |
| Gm18 | 1564092 | A | T | Yes | No |
| Gm18 | 1579201 | G | A | Yes | No |
| Gm18 | 1539750 | G | A | Yes | No |
| Gm18 | 1659829 | C | T | Yes | No |
| Gm18 | 1612553 | G | A | Yes | No |
| Gm18 | 1538114 | A | G | Yes | No |
| Gm18 | 1762540 | N | A | Yes | Yes |
| Gm18 | 1701861 | A | G | No | Yes |
| Gm18 | 1764886 | A | G | Yes | Yes |
| Gm18 | 1542804 | G | A | Yes | No |
| Gm18 | 1717676 | A | G | Yes | Yes |
| Gm18 | 1568958 | T | C | No | Yes |
| Gm18 | 1700692 | T | C | No | Yes |
| Gm18 | 1702741 | T | C | Yes | No |
| Gm18 | 1700725 | C | T | Yes | Yes |
| Gm18 | 1692272 | A | T | Yes | Yes |
| Gm18 | 1600077 | G | A | No | Yes |
| Gm18 | 1567770 | C | T | No | Yes |
| Gm18 | 1531244 | G | A | Yes | No |
| Gm18 | 1772523 | G | A | Yes | No |
| Gm18 | 1592832 | T | C | Yes | Yes |
| Gm18 | 1684187 | T | C | Yes | No |
| Gm18 | 1750533 | G | T | No | Yes |
| Gm18 | 1717672 | C | T | Yes | Yes |
| Gm18 | 1567714 | A | G | No | Yes |
| Gm18 | 1578727 | G | T | Yes | No |
| Gm18 | 1663064 | A | G | Yes | No |
| Gm18 | 1688429 | T | C | No | Yes |
| Gm18 | 1678548 | T | A | Yes | Yes |
| Gm18 | 1692562 | A | G | Yes | Yes |
| Gm18 | 1750710 | T | C | No | Yes |
| Gm18 | 1555210 | C | G | Yes | No |
| Gm18 | 1566988 | C | T | Yes | No |
| Gm18 | 1541254 | T | C | Yes | No |
| Gm18 | 1702482 | C | T | Yes | Yes |
| Gm18 | 1771385 | T | G | Yes | Yes |
| Gm18 | 1582767 | C | T | Yes | Yes |
| Gm18 | 1612042 | A | G | Yes | Yes |
| Gm18 | 1567449 | T | G | No | Yes |
| Gm18 | 1545916 | C | T | Yes | No |
| Gm18 | 1700984 | T | A | No | Yes |
| Gm18 | 1605993 | G | A | Yes | Yes |
| Gm18 | 1599921 | G | A | Yes | Yes |
| Gm18 | 1750871 | G | A | No | Yes |
| Gm18 | 1599897 | A | G | Yes | Yes |
| Gm18 | 1517411 | C | A | Yes | No |
| Gm18 | 1750012 | G | A | No | Yes |
| Gm18 | 1651606 | A | T | Yes | Yes |
| Gm18 | 1692394 | C | T | Yes | Yes |
| Gm18 | 1707082 | G | A | Yes | No |
| Gm18 | 1692180 | A | G | Yes | Yes |
| Gm18 | 1758510 | G | A | No | Yes |
| Gm18 | 1531264 | T | C | Yes | No |
| Gm18 | 1568870 | T | G | No | Yes |
| Gm18 | 1763296 | G | T | Yes | No |
| Gm18 | 1754546 | T | C | No | Yes |
| Gm18 | 1738263 | T | A | Yes | Yes |
| Gm18 | 1762539 | N | C | Yes | Yes |
| Gm18 | 1516055 | C | T | Yes | Yes |
| Gm18 | 1598101 | G | T | Yes | No |
| Gm18 | 1568939 | G | A | No | Yes |
| Gm18 | 1516449 | A | G | Yes | No |
| Gm18 | 1509282 | G | C | No | Yes |
| Gm18 | 1684242 | A | G | Yes | No |
| Gm18 | 1568012 | G | A | Yes | Yes |
| Gm18 | 1666930 | A | G | Yes | No |
| Gm18 | 1516837 | G | A | Yes | No |
| Gm18 | 1547341 | C | T | Yes | No |
| Gm18 | 1603797 | T | C | Yes | No |
| Gm18 | 1568784 | C | G | No | Yes |
| Gm18 | 1692368 | C | T | No | Yes |
| Gm18 | 1605938 | T | C | Yes | Yes |
| Gm18 | 1766496 | G | A | No | Yes |
| Gm18 | 1767775 | T | A | No | Yes |
| Gm18 | 1605297 | G | A | No | Yes |
| Gm18 | 1678365 | A | C | Yes | No |
| Gm18 | 1659371 | A | G | No | Yes |
| Gm18 | 1568820 | G | A | Yes | No |
| Gm18 | 1566882 | C | T | Yes | Yes |
| Gm18 | 1759307 | G | A | Yes | No |
| Gm18 | 1717699 | T | A | Yes | Yes |
| Gm18 | 1733287 | T | C | Yes | Yes |

TABLE 2-continued

| #CHROM | POS | REF | ALT | Peking | PI88788 |
|---|---|---|---|---|---|
| Gm18 | 1630447 | T | G | Yes | Yes |
| Gm18 | 1736377 | G | A | Yes | Yes |
| Gm18 | 1752898 | T | A | Yes | Yes |
| Gm18 | 1568019 | A | T | Yes | Yes |
| Gm18 | 1766342 | G | A | No | Yes |
| Gm18 | 1749959 | G | C | No | Yes |
| Gm18 | 1749955 | T | C | No | Yes |
| Gm18 | 1666561 | T | C | Yes | No |
| Gm18 | 1600097 | A | G | No | Yes |
| Gm18 | 1572432 | T | C | No | Yes |
| Gm18 | 1625392 | T | G | Yes | Yes |
| Gm18 | 1663967 | G | A | Yes | No |
| Gm18 | 1707757 | T | C | Yes | Yes |
| Gm18 | 1567788 | C | T | No | Yes |
| Gm18 | 1725932 | C | T | Yes | No |
| Gm18 | 1662666 | G | A | Yes | No |
| Gm18 | 1568868 | C | A | No | Yes |
| Gm18 | 1750007 | C | A | No | Yes |
| Gm18 | 1663535 | T | C | Yes | No |
| Gm18 | 1592769 | T | C | Yes | Yes |
| Gm18 | 1605606 | A | G | No | Yes |
| Gm18 | 1692198 | A | G | Yes | Yes |
| Gm18 | 1692240 | C | T | Yes | Yes |
| Gm18 | 1685571 | T | A | Yes | No |
| Gm18 | 1708232 | C | A | Yes | Yes |
| Gm18 | 1759764 | T | G | Yes | Yes |
| Gm18 | 1751112 | G | A | No | Yes |
| Gm18 | 1677142 | G | T | Yes | Yes |
| Gm18 | 1691976 | C | T | Yes | Yes |
| Gm18 | 1663501 | C | T | No | Yes |
| Gm18 | 1727330 | T | C | Yes | No |
| Gm18 | 1765635 | T | C | No | Yes |
| Gm18 | 1717310 | G | A | No | Yes |
| Gm18 | 1759724 | T | C | Yes | Yes |
| Gm18 | 1635035 | G | A | Yes | Yes |
| Gm18 | 1626986 | T | A | Yes | Yes |
| Gm18 | 1762538 | N | T | Yes | Yes |
| Gm18 | 1595321 | T | C | Yes | No |
| Gm18 | 1566434 | T | C | Yes | No |
| Gm18 | 1753018 | G | A | Yes | Yes |
| Gm18 | 1569369 | T | C | No | Yes |
| Gm18 | 1635376 | C | A | Yes | No |
| Gm18 | 1600011 | C | T | Yes | No |
| Gm18 | 1692566 | A | T | Yes | Yes |
| Gm18 | 1692784 | G | A | No | Yes |
| Gm18 | 1707915 | C | T | Yes | Yes |
| Gm18 | 1702563 | C | A | Yes | No |
| Gm18 | 1624678 | C | T | Yes | No |
| Gm18 | 1676981 | T | C | Yes | Yes |
| Gm18 | 1729866 | C | T | Yes | No |
| Gm18 | 1717224 | G | A | No | Yes |
| Gm18 | 1600033 | C | T | Yes | No |
| Gm18 | 1715288 | T | G | Yes | No |
| Gm18 | 1693319 | A | C | No | Yes |
| Gm18 | 1566930 | G | A | Yes | Yes |
| Gm18 | 1762377 | N | A | Yes | Yes |
| Gm18 | 1684117 | A | T | Yes | Yes |
| Gm18 | 1569146 | C | T | Yes | No |
| Gm18 | 1570126 | G | C | No | Yes |
| Gm18 | 1762537 | N | G | Yes | Yes |
| Gm18 | 1569349 | N | T | Yes | Yes |
| Gm18 | 1667726 | T | C | Yes | No |
| Gm18 | 1517191 | G | A | Yes | No |
| Gm18 | 1614960 | A | T | Yes | No |
| Gm18 | 1726680 | G | T | No | Yes |
| Gm18 | 1726068 | G | T | Yes | No |
| Gm18 | 1669829 | T | C | Yes | No |
| Gm18 | 1766704 | A | G | No | Yes |
| Gm18 | 1715459 | T | C | Yes | No |
| Gm18 | 1700956 | T | G | Yes | Yes |
| Gm18 | 1750473 | C | T | No | Yes |
| Gm18 | 1760838 | N | G | Yes | Yes |
| Gm18 | 1756288 | A | T | No | Yes |
| Gm18 | 1708549 | G | A | Yes | No |
| Gm18 | 1711611 | T | G | No | Yes |
| Gm18 | 1562884 | A | G | Yes | No |
| Gm18 | 1538857 | T | C | Yes | No |
| Gm18 | 1760837 | N | G | Yes | Yes |
| Gm18 | 1717303 | C | T | No | Yes |
| Gm18 | 1512555 | A | T | Yes | No |
| Gm18 | 1749997 | G | A | No | Yes |
| Gm18 | 1653945 | C | T | Yes | No |
| Gm18 | 1569348 | N | T | Yes | Yes |
| Gm18 | 1729673 | A | G | Yes | No |
| Gm18 | 1568005 | A | G | Yes | Yes |
| Gm18 | 1762378 | N | C | Yes | Yes |
| Gm18 | 1569128 | C | T | No | Yes |
| Gm18 | 1623625 | A | G | Yes | Yes |
| Gm18 | 1560088 | C | T | Yes | No |
| Gm18 | 1692818 | G | A, C | Yes | Yes |
| Gm18 | 1766676 | C | T | No | Yes |
| Gm18 | 1662124 | A | T | Yes | Yes |
| Gm18 | 1592838 | C | T | Yes | Yes |
| Gm18 | 1669151 | T | A | Yes | No |
| Gm18 | 1619145 | A | G | Yes | No |
| Gm18 | 1675126 | G | A | Yes | No |
| Gm18 | 1707897 | C | T | Yes | Yes |
| Gm18 | 1565888 | C | T | Yes | Yes |
| Gm18 | 1766655 | C | A | Yes | Yes |
| Gm18 | 1519508 | C | G | Yes | No |
| Gm18 | 1666849 | T | A | Yes | No |
| Gm18 | 1663623 | C | T | Yes | No |
| Gm18 | 1701854 | A | G | Yes | No |
| Gm18 | 1569347 | N | A | Yes | Yes |
| Gm18 | 1520675 | C | T | Yes | No |
| Gm18 | 1766798 | T | A | No | Yes |
| Gm18 | 1700959 | T | C | Yes | Yes |
| Gm18 | 1762379 | N | T | Yes | Yes |
| Gm18 | 1708127 | T | C | Yes | Yes |
| Gm18 | 1524498 | G | T | Yes | No |
| Gm18 | 1680668 | T | G | Yes | No |
| Gm18 | 1545360 | A | G | Yes | No |
| Gm18 | 1677459 | A | G | Yes | No |
| Gm18 | 1687115 | A | T | Yes | No |
| Gm18 | 1650501 | T | A | Yes | No |
| Gm18 | 1717349 | A | C | No | Yes |
| Gm18 | 1700966 | G | A | No | Yes |
| Gm18 | 1674960 | C | T | Yes | No |
| Gm18 | 1674957 | T | A | Yes | No |
| Gm18 | 1623626 | C | T | Yes | Yes |
| Gm18 | 1563153 | G | T | Yes | No |
| Gm18 | 1569346 | N | T | Yes | Yes |
| Gm18 | 1541604 | C | A | Yes | No |
| Gm18 | 1707790 | G | A | Yes | Yes |
| Gm18 | 1600007 | C | T | No | Yes |
| Gm18 | 1606554 | G | A | No | Yes |
| Gm18 | 1765046 | G | C | No | Yes |
| Gm18 | 1765048 | G | C | No | Yes |
| Gm18 | 1751052 | A | G | No | Yes |
| Gm18 | 1715256 | A | G | Yes | No |
| Gm18 | 1684351 | G | A | Yes | No |
| Gm18 | 1541073 | C | T | Yes | No |
| Gm18 | 1759782 | C | A | Yes | Yes |
| Gm18 | 1759784 | C | A | Yes | Yes |
| Gm18 | 1762380 | N | A | Yes | Yes |
| Gm18 | 1765764 | T | C | No | Yes |
| Gm18 | 1708244 | A | G | No | Yes |
| Gm18 | 1654795 | T | A | Yes | No |
| Gm18 | 1716443 | T | A | No | Yes |
| Gm18 | 1692787 | T | C | No | Yes |
| Gm18 | 1708120 | C | A | Yes | Yes |
| Gm18 | 1569345 | N | A | Yes | Yes |
| Gm18 | 1579346 | T | G | Yes | No |
| Gm18 | 1765552 | T | C | No | Yes |
| Gm18 | 1599864 | G | A | Yes | No |
| Gm18 | 1561009 | G | A | Yes | No |
| Gm18 | 1550213 | T | A | Yes | No |
| Gm18 | 1679773 | A | G | Yes | No |
| Gm18 | 1702269 | A | T | Yes | Yes |
| Gm18 | 1740974 | T | A | Yes | Yes |
| Gm18 | 1576454 | G | T | Yes | Yes |
| Gm18 | 1599836 | T | G | No | Yes |
| Gm18 | 1559151 | A | T | Yes | No |
| Gm18 | 1599608 | C | T | No | Yes |
| Gm18 | 1669541 | T | C | Yes | No |
| Gm18 | 1669348 | C | T | Yes | Yes |

TABLE 2-continued

| #CHROM | POS | REF | ALT | Peking | PI88788 |
|---|---|---|---|---|---|
| Gm18 | 1691780 | A | T | No | Yes |
| Gm18 | 1565900 | G | A | Yes | Yes |
| Gm18 | 1762381 | N | T | Yes | Yes |
| Gm18 | 1762382 | N | T | Yes | Yes |
| Gm18 | 1565926 | A | G | Yes | Yes |
| Gm18 | 1618118 | T | A | Yes | No |
| Gm18 | 1754310 | A | G | Yes | No |
| Gm18 | 1599717 | G | A | Yes | No |
| Gm18 | 1680693 | G | T | Yes | No |
| Gm18 | 1566975 | T | C | Yes | Yes |
| Gm18 | 1733286 | A | G | Yes | Yes |
| Gm18 | 1703713 | A | T | Yes | Yes |
| Gm18 | 1565865 | T | G | Yes | Yes |
| Gm18 | 1752043 | T | A | Yes | Yes |
| Gm18 | 1766803 | G | A | No | Yes |
| Gm18 | 1565931 | A | G | Yes | Yes |
| Gm18 | 1690522 | G | C | Yes | No |
| Gm18 | 1634323 | C | T | Yes | No |
| Gm18 | 1766736 | A | G | No | Yes |
| Gm18 | 1554156 | T | A | Yes | No |
| Gm18 | 1762686 | A | G | Yes | No |
| Gm18 | 1775071 | G | C | No | Yes |
| Gm18 | 1762535 | N | A | Yes | Yes |
| Gm18 | 1762536 | N | A | Yes | Yes |
| Gm18 | 1762383 | N | A | Yes | Yes |
| Gm18 | 1599975 | A | G | No | Yes |
| Gm18 | 1565917 | T | C | Yes | Yes |
| Gm18 | 1700569 | T | G | Yes | Yes |
| Gm18 | 1725538 | T | G | Yes | No |
| Gm18 | 1751021 | G | A | No | Yes |
| Gm18 | 1692901 | A | T | Yes | No |
| Gm18 | 1669115 | T | C | Yes | Yes |
| Gm18 | 1666527 | T | A | Yes | No |
| Gm18 | 1669481 | A | T | Yes | No |
| Gm18 | 1753738 | T | A | Yes | Yes |
| Gm18 | 1685923 | C | T | Yes | No |
| Gm18 | 1691942 | G | C | No | Yes |
| Gm18 | 1753009 | T | C | Yes | Yes |
| Gm18 | 1764965 | T | C | Yes | Yes |
| Gm18 | 1548716 | C | T | Yes | No |
| Gm18 | 1518206 | A | G | Yes | No |
| Gm18 | 1566429 | C | T | Yes | No |
| Gm18 | 1762695 | C | G | Yes | No |
| Gm18 | 1752808 | A | T | Yes | No |
| Gm18 | 1762533 | N | A | Yes | Yes |
| Gm18 | 1762534 | N | G | Yes | Yes |
| Gm18 | 1654800 | T | A | Yes | No |
| Gm18 | 1552671 | A | G | Yes | No |
| Gm18 | 1749975 | T | C | No | Yes |
| Gm18 | 1538953 | A | C | Yes | No |
| Gm18 | 1707115 | A | G | Yes | No |
| Gm18 | 1766276 | G | A | No | Yes |
| Gm18 | 1512962 | G | T | Yes | No |
| Gm18 | 1560166 | G | A | Yes | No |
| Gm18 | 1577691 | T | C | Yes | No |
| Gm18 | 1749887 | C | A | No | Yes |
| Gm18 | 1766748 | A | T | No | Yes |
| Gm18 | 1751663 | T | A | Yes | Yes |
| Gm18 | 1614300 | T | A | Yes | No |
| Gm18 | 1765697 | A | C | No | Yes |
| Gm18 | 1677110 | C | T | Yes | Yes |
| Gm18 | 1708139 | G | A | Yes | Yes |
| Gm18 | 1764424 | T | C | Yes | Yes |
| Gm18 | 1765126 | C | T | No | Yes |
| Gm18 | 1759795 | C | A | Yes | Yes |
| Gm18 | 1538142 | A | G | Yes | No |
| Gm18 | 1606442 | T | A | Yes | No |
| Gm18 | 1600154 | T | C | Yes | Yes |
| Gm18 | 1751134 | T | C | No | Yes |
| Gm18 | 1750927 | A | G | No | Yes |
| Gm18 | 1763858 | T | C | Yes | Yes |
| Gm18 | 1541357 | G | A | Yes | No |
| Gm18 | 1565864 | T | C | Yes | Yes |
| Gm18 | 1569140 | A | T | No | Yes |
| Gm18 | 1543480 | C | T | Yes | No |
| Gm18 | 1565826 | T | A | No | Yes |
| Gm18 | 1568761 | G | A | No | Yes |
| Gm18 | 1765272 | T | C | No | Yes |
| Gm18 | 1759787 | C | A | Yes | Yes |
| Gm18 | 1725547 | T | C | No | Yes |
| Gm18 | 1566947 | C | T | Yes | Yes |
| Gm18 | 1765925 | C | A | No | Yes |
| Gm18 | 1560043 | T | A | Yes | No |
| Gm18 | 1760836 | N | T | Yes | Yes |
| Gm18 | 1657183 | G | T | Yes | No |
| Gm18 | 1706442 | A | T | No | Yes |
| Gm18 | 1759811 | C | T | Yes | Yes |
| Gm18 | 1765783 | A | G | No | Yes |
| Gm18 | 1669584 | C | A | Yes | No |
| Gm18 | 1663553 | T | C | Yes | No |
| Gm18 | 1585768 | T | A | Yes | Yes |
| Gm18 | 1550153 | T | A | Yes | No |
| Gm18 | 1670034 | T | C | Yes | No |
| Gm18 | 1764443 | A | G | Yes | Yes |
| Gm18 | 1692545 | A | T | Yes | Yes |
| Gm18 | 1569344 | N | G | Yes | Yes |
| Gm18 | 1759791 | C | A | Yes | Yes |
| Gm18 | 1753351 | C | A | Yes | No |
| Gm18 | 1662177 | G | A | Yes | Yes |
| Gm18 | 1604031 | A | G | Yes | No |
| Gm18 | 1568929 | A | G | Yes | Yes |
| Gm18 | 1569343 | N | A | Yes | Yes |
| Gm18 | 1765276 | G | T | No | Yes |
| Gm18 | 1550179 | G | C | Yes | No |
| Gm18 | 1765155 | A | G | No | Yes |
| Gm18 | 1561190 | T | A | Yes | No |
| Gm18 | 1751031 | C | T | No | Yes |
| Gm18 | 1766272 | G | A | No | Yes |
| Gm18 | 1568541 | A | T | Yes | No |
| Gm18 | 1600017 | G | A | No | Yes |
| Gm18 | 1600015 | G | A | No | Yes |
| Gm18 | 1765977 | C | T | No | Yes |
| Gm18 | 1577633 | T | G | Yes | No |
| Gm18 | 1687822 | G | A | Yes | No |
| Gm18 | 1751017 | T | C | No | Yes |
| Gm18 | 1700363 | A | T | Yes | No |
| Gm18 | 1763838 | C | T | Yes | Yes |
| Gm18 | 1569341 | N | T | Yes | Yes |
| Gm18 | 1569342 | N | A | Yes | Yes |
| Gm18 | 1734691 | C | T | Yes | No |
| Gm18 | 1576755 | G | A | Yes | No |
| Gm18 | 1708143 | C | A | Yes | Yes |
| Gm18 | 1706995 | G | A | Yes | No |
| Gm18 | 1766728 | G | C | No | Yes |
| Gm18 | 1569136 | T | C | No | Yes |
| Gm18 | 1766283 | A | T | No | Yes |
| Gm18 | 1765717 | C | T | No | Yes |
| Gm18 | 1600085 | C | T | Yes | No |
| Gm18 | 1560170 | A | T | Yes | No |
| Gm18 | 1669190 | G | A | Yes | No |
| Gm18 | 1706441 | C | T | No | Yes |
| Gm18 | 1766726 | G | T | No | Yes |
| Gm18 | 1765151 | G | A | No | Yes |
| Gm18 | 1759789 | C | A | Yes | Yes |
| Gm18 | 1708057 | G | T | Yes | Yes |
| Gm18 | 1612408 | T | A | Yes | No |
| Gm18 | 1664020 | G | A | Yes | No |
| Gm18 | 1766458 | A | C | No | Yes |
| Gm18 | 1763828 | A | G | Yes | Yes |
| Gm18 | 1749980 | C | T | No | Yes |
| Gm18 | 1561783 | A | G | Yes | No |
| Gm18 | 1554570 | A | C | Yes | No |
| Gm18 | 1599841 | C | T | Yes | No |
| Gm18 | 1759095 | T | G | Yes | No |
| Gm18 | 1570660 | T | C | Yes | No |
| Gm18 | 1554430 | G | A | Yes | No |
| Gm18 | 1606726 | C | T | Yes | Yes |
| Gm18 | 1663564 | A | G | Yes | No |
| Gm18 | 1599993 | G | A | No | Yes |
| Gm18 | 1707774 | T | C | Yes | Yes |
| Gm18 | 1516597 | T | C | Yes | No |
| Gm18 | 1551775 | T | A | Yes | No |
| Gm18 | 1555237 | G | A | Yes | No |
| Gm18 | 1766719 | T | C | No | Yes |
| Gm18 | 1705753 | G | A | No | Yes |
| Gm18 | 1581688 | T | A | Yes | No |

TABLE 2-continued

| #CHROM | POS | REF | ALT | Peking | PI88788 |
|---|---|---|---|---|---|
| Gm18 | 1565948 | G | T | Yes | Yes |
| Gm18 | 1669557 | G | A | Yes | No |
| Gm18 | 1758523 | C | T | No | Yes |
| Gm18 | 1561651 | C | T | Yes | No |
| Gm18 | 1555277 | T | C | Yes | No |
| Gm18 | 1699343 | C | T | Yes | No |
| Gm18 | 1692163 | C | T | Yes | Yes |
| Gm18 | 1568727 | T | G | No | Yes |
| Gm18 | 1622108 | A | T | Yes | Yes |
| Gm18 | 1599986 | C | T | No | Yes |
| Gm18 | 1509119 | T | C | Yes | No |
| Gm18 | 1765980 | C | T | No | Yes |
| Gm18 | 1765228 | A | G | No | Yes |
| Gm18 | 1524257 | T | A | Yes | No |
| Gm18 | 1634636 | C | T | No | Yes |
| Gm18 | 1550053 | G | T | Yes | No |
| Gm18 | 1756096 | G | A | Yes | No |
| Gm18 | 1762531 | N | C | Yes | Yes |
| Gm18 | 1762532 | N | A | Yes | Yes |
| Gm18 | 1766399 | G | A | No | Yes |
| Gm18 | 1569035 | G | T | Yes | Yes |
| Gm18 | 1766390 | C | T | No | Yes |
| Gm18 | 1632227 | A | G | Yes | Yes |
| Gm18 | 1569962 | C | T | No | Yes |
| Gm18 | 1612073 | A | T | No | Yes |
| Gm18 | 1750156 | C | T | No | Yes |
| Gm18 | 1766716 | G | A | No | Yes |
| Gm18 | 1552165 | A | C | Yes | No |
| Gm18 | 1628562 | G | C | Yes | No |
| Gm18 | 1548918 | C | G | Yes | No |
| Gm18 | 1639650 | T | C | Yes | Yes |
| Gm18 | 1612428 | A | G | Yes | No |
| Gm18 | 1752840 | G | C | No | Yes |
| Gm18 | 1676925 | T | A | Yes | Yes |
| Gm18 | 1554604 | A | G | Yes | No |
| Gm18 | 1606053 | G | A | Yes | No |

TABLE 3

Summary of SEQ ID NOs

| SEQ ID | Description |
|---|---|
| 1 | Glyma18g2570 |
| 2 | Glyma18g2590 |
| 3 | Glyma18g2580 |
| 4 | Glyma18g2600 |
| 5 | Glyma18g2610 |
| 6 | Breakpoint amplicon of peking soybean |
| 7 | Breakpoint amplicon of peking soybean |
| 8 | Breakpoint amplicon of pi88788 soybean |
| 9 | Breakpoint amplicon of pi88788 soybean |
| 10 | Forward Primer Rhg1_(dark black/dark black) |
| 11 | Reverse primer Rhg1_(dark black/dark black) |
| 12 | Forward Primer Rhg1_(light grey/light grey) |
| 13 | Reverse primer Rhg1_(light grey/light grey) |
| 14 | Forward Primer Rhg1_(dark black/light grey) |
| 15 | Reverse primer Rhg1_(dark black/light grey) |
| 16 | Rhg1_Seq* forward primer |
| 17 | Rhg1_Seq* reverse primer |
| 18 | Contig spanning the duplication breakpoint |
| 19 | Contig spanning the duplication breakpoint |
| 20 | Contig spanning the duplication breakpoint |
| 21 | Contig spanning the duplication breakpoint |
| 22 | Sequence of amplicon spanning the breakpoint. |
| 23 | Sequence of breakpoint |
| 24 | Sequence of amplicon spanning the breakpoint. |
| 25 | Sequence of breakpoint |
| 26-49 | Primers shown in FIG. 8 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of selecting a soybean plant or a soybean germplasm with resistance to a soybean cyst nematode, the method comprising:
   (i) detecting, using quantitative PCR or other quantitative technique, in the genome of the soybean plant or in the genome of the soybean germplasm:
      (a) a duplication of a region within the rhg1 locus;
      (b) an increased copy number of at least SEQ ID NO: 1; or
      (c) a DNA junction formed at the breakpoint of a duplicated region within the rhg1 locus, wherein the DNA junction sequence is SEQ ID NO: 6;
   (ii) selecting the soybean plant or the soybean germplasm having the duplication, increased copy number or DNA junction; and
   (iii) crossing the selected soybean plant with another soybean plant and selecting a progeny thereof having the duplication, increased copy number or DNA junction.

2. The method of claim 1, wherein in step (i)a the duplication of the region within the rhg1 locus comprises a tandem duplication of the soybean genome between about position Gm18:1663448 and about position Gm18:1632228.

3. The method of claim 1, wherein in step (i)a the duplication of the region within the rhg1 locus comprises the region as set forth in SEQ ID NO:1.

4. The method of claim 1, wherein in step (i)c the duplicated region within the rhg1 locus comprises a tandem duplication of the soybean genome between about position Gm18:1663448 and about position Gm18:1632228.

5. The method of claim 1, wherein in step (i)c detecting the DNA junction comprises PCR amplification of the DNA junction formed at the breakpoint of the duplicated region within the rhg1 locus.

6. The method of claim 5, wherein said PCR amplification employs the primer pair set forth in SEQ ID NO: 14 and 15.

7. The method of claim 1, wherein in step (i)c detecting the DNA junction comprises DNA sequencing.

8. The method of claim 1, wherein in step (iii) crossing is selfing.

9. The method of claim 1, wherein in step (iii) crossing is backcrossing.

* * * * *

SEQUENCE LISTING

<160> NUMBER OF SEQ ID NOS: 49

<210> SEQ ID NO 1
<211> LENGTH: 1096
<212> TYPE: DNA
<213> ORGANISM: Glycine max

<400> SEQUENCE: 1

```
aagacattcg ggttcggatc ctgtagtgtc atcactcgtt agatttcgat gaagaatagt      60
tagagagtgc tgtgagcttc agcaaaatgc gcgccctagc agctcagttc tctaattatt     120
tatgcagaag aaaagtttgg gtcaatctgc gatctcgtaa tttttcatca tataacagta     180
aagatgagct aaccatcgag gaagaagctg agagaaaagt tggatggcta ttgaagacga     240 tatttttgt cactgcaggg gtagcaggat accatttctt tccttatatg ggagagaatt     300
tgatgcaaca gtctgtttcg cttttgcgtg tcaaggatcc cttgttcaaa aggatgggag     360
cttctagatt ggctcgttt gcagtagatg atgaaagaag gaagaagata gttgagatgg     420
```

| | |
|---|---|
| gtggagctca agaactctta aatatgttaa gcactgctaa agacgaccgt acacggaaag | 480 |
| aagcattgca tgctcttgat gcactgtcac aatcagatga agctcttgca tccttgcatc | 540 |
| atgctggggc catttcagta attaggtctg caccaaattc acttgaggat gcagaagttg | 600 |
| agggattcaa gttgagcttg atgaaaagat ttcaagatct cagatatgat gtgccatcat | 660 |
| gacttgaggt gcatgcctcc ttttgcttta tgttttggt tggttggagc atgaaataac | 720 |
| atgatatgag aaattaagct ggcaaccaaa gcttttgtgg ggaagagtac ttgaaattac | 780 |
| tgtgtatcat ttgaccaaat ctaatggaag attatagttc tattgtcatt ttagtttttt | 840 |
| tcacttgtca aatgcgattt gtcgctcatt gttctgtcaa tcataataaa atggaaaaga | 900 |
| tttatgtgca tgtcaatttt tatttttga aatatgtgtt tagaagataa aagattacaa | 960 |
| caaactagta ttgaagttgt aagtgtttag atactgtaat tgtatatttg gttaacacta | 1020 |
| ctagattaaa tttaagcctc aactttcaaa tgtgattgat catataatgt cataaaatgt | 1080 |
| gtgtaattat aggttg | 1096 |

<210> SEQ ID NO 2
<211> LENGTH: 1353
<212> TYPE: DNA
<213> ORGANISM: Glycine max

<400> SEQUENCE: 2

| | |
|---|---|
| ggacaatcct tcttgttacg caattctgaa tttgcgggtt ttggatttgg acttggtcgt | 60 |
| caacacagtc taattaatat cttttgctc cttcgcttat gaatcttctt cttcttcttc | 120 |
| ttgttcctgc aacgcactga attcgatcaa tcaatccatc ttcaattgct ttgtttcgat | 180 |
| cggaggaaaa tggccgatca gttatcgaag ggagaggaat tcgagaaaaa ggctgagaag | 240 |
| aagctcagcg gttggggctt gtttggctcc aagtatgaag atgccgccga tctcttcgat | 300 |
| aaagccgcca attgcttcaa gctcgccaaa tcatgggaca aggctggagc acataacctg | 360 |
| aagttggcaa gttgtcattt gaagttggaa agcaagcatg aagctgcaca ggcccatgtc | 420 |
| gatgctgcac attgctacaa aaagactaat ataaacgagt ctgtatcttg cttagaccga | 480 |
| gctgtaaatc ttttctgtga cattggaaga ctctctatgg ctgctagata tttaaaggaa | 540 |
| attgctgaat tgtacgaggg tgaacagaat attgagcagg ctcttgttta ctatgaaaaa | 600 |
| tcagctgatt tttttcaaaa tgaagaagtg acaacttctg cgaaccaatg caaacaaaaa | 660 |
| gttgcccagt ttgctgctca gctagaacaa tatcagaagt cgattgacat ttatgaagag | 720 |
| atagctcgcc aatccctcaa caataatttg ctgaagtatg gagttaaagg acaccttctt | 780 |
| aatgctggca tctgccaact ctgtaaagag gacgttgttg ctataaccaa tgcattagaa | 840 |
| cgatatcagg aactggatcc aacattttca ggaacacgtg aatatagatt gttggcggac | 900 |
| attgctgctg caattgatga agaagatgtt gcaaagttta ctgatgttgt caaggaattt | 960 |
| gatagtatga cccctctgga ttcttggaag accacacttc tcttaagggt gaaggaaaag | 1020 |
| ctgaaagcca agaacttga ggaggatgat cttacttgaa ttgtaccttt aatattcctg | 1080 |
| gtggttggac ctattgtttg atgatttaca ttgtactact atgtgtgtct gtccagttgt | 1140 |
| tcgtcttaca catccactta cagagtgtac ctgctttggt tttaattgaa ttggtctgac | 1200 |
| tgaattcaaa aaatgagttt ttaatgaggt tgctggagtc tgatcttatc tacattatta | 1260 |
| tgaattgaat tactatctat acttgtttta caccaggttt atgcgaacct gttagcaata | 1320 |
| ctaatccatg ttactttatg cggataatcc ata | 1353 |

<210> SEQ ID NO 3
<211> LENGTH: 1658
<212> TYPE: DNA
<213> ORGANISM: Glycine max

<400> SEQUENCE: 3

```
aattcaaaga tagtaggctg ccaggcaccg cacaccgcca ccgcactttc tccgatcctc      60
acaattttgc ctccggcatg tctccggccg ccggagtcag cgtcccctc ctgggggatt     120
ccaaaggaac gccgccgccg gcttccgtcc ccggcgcggt gttcaacgtg gccaccagca     180
tagtcggcgc cggaatcatg tcgattccgg cgatcatgaa ggttctcggc gtagttcccg     240
ctttcgcgat gattctcgtg gtggccgtgc tggcggaact gtccgtgac ttcctgatgc     300
ggttcacgca ctccggcgaa acgacgacgt acgctggcgt catgagggag gcgttcggat     360
cgggtggagc attagccgcg caagtttgcg tcatcatcac caacgttggg ggtttaattc     420
tctaccttat catcatcgga gatgtgctat ctggaaagca aaatggaggg gaagtgcatt     480
tgggcatttt gcaacagtgg tttgaattc actggtggaa ttcccgggaa tttgctttgc     540
ttttcacctt ggtctttgtt atgcttccat tggtattgta caaacgtgta gagtccttga     600
agtacagctc tgcagtgtca actcttcttg cagtggcatt tgttggcata tgttgtgggt     660
tggctatcac agctctggtg caaggaaaaa cacaaactcc tagattgttt cctcggctag     720
actaccaaac ctcattcttt gatctgttca ctgcagttcc tgttgttgtc acagccttca     780
catttcactt taatgtgcac cccattgggt ttgagcttgc caaggcatcc caaatgacaa     840
cagcagttcg attagcatta ttgctttgtg ctgtgatcta ccttgcaata ggcttatttg     900
ggtacatgtt atttggggat tcaacccagt cagacattct catcaatttt gaccagaatg     960
ctggttcagc agttggttcc ttgctcaata gtttggtccg tgtaagctat gccctccaca    1020
tcatgctggt gtttcctctc ttgaacttct ctttgagaac caacatagat gaagttctct    1080
tccctaagaa gcctatgcta gccacagaca acaaaagatt tatgatcctc actctggtgc    1140
tgcttgtatt ctcctacctt gcagctatag caatcccaga tatttggtac ttctttcagt    1200
tcctgggatc ctcatccgca gtgtgccttg ccttcatttt ccccggctct attgttttaa    1260
gggatgttaa aggtatatca acgagaagag acaaaattat tgcactgata atgattatac    1320
tagctgtggt tacaagtgtg cttgccattt ccaccaacat atataatgct tttagtagca    1380
agtcataaat acaagctggt tctctcattt ctccccttct attgtttttt ttatatgtat    1440
agaaaatttt atttggggag agagggtatg gctggggaga ttctagaggc atttggttgc    1500
tgtggcgatt gtgttacttt tgtattttgg atcccttgtt gtttattgta gaattcatgt    1560
cttgtggcag catttctatg taaaatacca aatattaaag aaatgaaatc aacttgatgg    1620
ggtgacgaag ttggggccat atcttacaag tttgtgcc                            1658
```

<210> SEQ ID NO 4
<211> LENGTH: 1761
<212> TYPE: DNA
<213> ORGANISM: Glycine max

<400> SEQUENCE: 4

```
ctctgaggaa atcacacttc cccggccgtc atgagtcagc taattaattg tatttttctg      60
tacctatatc attgatgata cggttctgat ttgatcgaga aagctcagtt ttttatcaga     120
atggtttcgg ttgatgatgg gattgtgaat cccaatgatg aaattgagaa atctaacggg     180
agtaaagtga atgagtttgc atctatggat atttcagcaa ctcaaaaatc atatctgaac     240
```

```
agtgaagatc tcagagaag gcttcaggga accttaataa gttcttctgt tactaatagg    300
ataaactttc ttaaatttgg ttctgcatct gccaaattca aaaggcttgc tactgagaga    360
gaccaggttt ctatatctgt gccttctcct cgttcaaaga gcctaagatc acgtttcagt    420
ggcatgtttg ctcagaaact tgactgggct tcagtcaaga aaatgtgcat ggaatggatt    480
agaaatccag tgaacatggc cctttttgtg tggatcattt tgtgtcgcggt ttcgggtgct    540 attctgttcc ttgtcatgac aggcatgttg aatggtgtgc taccaagaaa gtctaagaga    600
aatgcatggt ttgaagtaaa caaccaaata ctcaatgcag tgtttacact cataccaaat    660
gacatctcta gccttaggaa ggtatattgc aagaatgtca cttacaagcc ccatgagtgg    720
acacatatga tggtagttgt cattctcctt catgttaact gttttgctca atatgcactt    780
tgtggtctaa acttagggta taaaaggtcc gagagacctg ccattggagt tggaatatgc    840
atatcttttg caattgctgg tttgtacacc attcttagcc cacttgggaa ggactatgat    900
tgtgagatgg atgaagaagc acaggttcaa attacagctt ctcaagggaa agagcagctg    960
agagagaaac caactgagaa gaaatattca tttgcatcca agatcaaca aagggttgtt    1020 gaaaatagac caaagtggag tggaggaata cttgacattt ggaacgatat ttccttagca    1080
tatctctcac ttttctgcac cttttgtgtg cttgggtgga atatgaagag gcttggctt    1140 ggaaacatgt atgttcacat tgccatttt atgctgttct gtatggctcc tttctggatt    1200
tttcttttgg cttccgttaa catagatgat gacaatgtta ggcaggctct agcagctgtt    1260
ggaatcattc tttgtttct tggtttattg tatggtggat tttggaggat ccaaatgaga    1320
aagaggttca atttaccagc ctatgacttc tgttttggca aaccttcagc ttctgattgc    1380
acactttggc taccctgttg ctggtgctct ctcgctcaag aagcgcgtac caggaataac    1440
tatgatcttg tagaagataa attctcaagg aaagaaactg atactagtga tcaaccatca    1500
atttcacctt tggctcgtga agatgtagtg tcaaccagat ctggcacaag ttctcctatg    1560
ggtagcacta gcaactcttc cccttatatg atgaaaacat ctagttctcc aaattcaagc    1620
aatgtcttaa agggatatta cagtccagat aagatgctat caactttgaa tgaagacaat    1680
tgtgaaagag gtcaagatgg aacaatgaac cccttatatg cacaaaaata atatcaaaat    1740
actatagaca ttaactctgt c                                              1761
```

<210> SEQ ID NO 5
<211> LENGTH: 893
<212> TYPE: DNA
<213> ORGANISM: Glycine max

<400> SEQUENCE: 5

```
tttggtttgg tttggttact tgaaaatctc gaatcgctta attttgattt agttttccac     60
cgcaacgcgg aacctctttc tcgaactggc taactctcag gcaagtggct cggacgctga    120
ttccagcaac acgcggctgg tggttgcact gtatgacgcc ctaaactccg gcgactccaa    180
cgccgtcgtc aagatcgtcg ccgccgatct cgagtggtgg ttccatggtc cgccctctca    240
ccagtttttg atgcgcatgc tcaccggcga ctccgccgcc gacaactcct tccgattcgt    300
tccgcagtcc atcgccgcct tcggctccac cgtcatcgtc gagggctgcg actccgcccg    360
caacattgcc tgggtccacg cctggaccgt cactgatggg atgatcactc aaatcagaga    420
gtacttcaac accgccctca ccgtcactcg catccacgat tccggcgaga ttgttccggc    480
cagatccggc gccggccgtt tgccctgcgt ctggagagag agcgtctccg gtcgggtcgg    540
gaaatccgtc cccggtttgg ttctcgcaat ataaaatata aaataagtaa ttagggaagg    600
```

| acgaggtcac gtgttgccgt tgctataata attaaataag ggacttgtgc acgtggcggt | 660 |
| gactggatcg atcggtttca gggaacattg atactttgtg ttagtattgg aggttaggga | 720 |
| gatgtgagag ctttgttgtt attggtgtgg tttgttttgt ttgcttgtgt gttttttcacc | 780 |
| actatgggcg tattcaggtg gttgtatctt tcttttgtta tttggagtgt tgatgatgat | 840 |
| gcaataagaa tatctatgga ctatgctttt aagagttggg ttgtgatgat gcc | 893 |

<210> SEQ ID NO 6
<211> LENGTH: 727
<212> TYPE: DNA
<213> ORGANISM: Glycine max
<220> FEATURE:
<221> NAME/KEY: misc_feature
<222> LOCATION: 7, 21, 639, 695, 697, 714
<223> OTHER INFORMATION: n = A,T,C or G

<400> SEQUENCE: 6

| ttctacntat gtaatacttc naattgtttg atgagatcgt taaaaagata tctgaagaga | 60 |
| gatataaata ttttttcattt tctgttctat attttgggat ttcatcttct tgtctctatt | 120 |
| gtaccaattg tgggtctgtt ttgatttgac tgtttgtagc acgtttcaat gcacttgttg | 180 |
| gagactttct tgtaacttta ttgattatag tgaaattatt ctttggtat gaatgatccg | 240 |
| tgatttttat ccttgcattg aggggttttt cactttaaac aaattgtgtc tcttgtgtgc | 300 |
| ttttaatttc tattttgctc tctttatatt ttagcctgct cctcacaaat tcttgcaagt | 360 |
| ttggaccaat ttatttctac tgcctatatt actttgttat tgtgttggta tattttcttc | 420 |
| atcaaagaat atccatttgt gctttaaatt tgggtagtt ttgtttcttg ctccacaaat | 480 |
| ttttgcagtt ttagtggaaa ggcccaacca atattctcaa cattttgggc cttcctcgaa | 540 |
| caaggacccg taagaataga agtttctaaa atggactgat aatcaaatag ttattgagat | 600 |
| ttttaattga gctgcatttg ttaagaagtc acggctaana gagttaccta gttgtcagtt | 660 |
| atactatttt catgactaag cagcaagcac agatntngca gtgatacaca accnagagca | 720 |
| tattctc | 727 |

<210> SEQ ID NO 7
<211> LENGTH: 728
<212> TYPE: DNA
<213> ORGANISM: Glycine max
<220> FEATURE:
<221> NAME/KEY: misc_feature
<222> LOCATION: 8, 22, 640, 695, 696, 697, 715, 717
<223> OTHER INFORMATION: n = A,T,C or G

<400> SEQUENCE: 7

| gttctacnta tgtaatactt cnaattgttt gatgagatcg ttaaaaagat atctgaagag | 60 |
| agatataaat attttttcatt ttctgttcta tattttggga tttcatcttc ttgtctctat | 120 |
| tgtaccaatt gtgggtctgt tttgatttga ctgtttgtag cacgtttcaa tgcacttgtt | 180 |
| ggagactttc ttgtaacttt attgattata gtgaaattat ttctttggta tgaatgatcc | 240 |
| gtgattttta ccttgcatt gaggggtttt tcactttaaa caaattgtgt ctcttgtgtg | 300 |
| cttttaattt ctattttgct ctctttatat tttagcctgc tcctcacaaa ttcttgcaag | 360 |
| tttggaccaa tttatttcta ctgcctatat tactttgtta ttgtgttggt atattttctt | 420 |
| catcaaagaa tatccatttg tgctttaaat tttgggtagt tttgtttctt gctccacaaa | 480 |
| tttttgcagt tttagtggaa aggcccaacc aatattctca cattttggg ccttcctcga | 540 |
| acaaggaccc gtaagaatag aagtttctaa aatggactga taatcaaata gttattgaga | 600 |

```
tttttaattg agctgcattt gttaagaagt cacggctaan agagttacct agttgtcagt    660
tatactattt tcatgactaa gcagcaagca cagannntgc agtgatacac aaccnanagc    720
atattctc                                                             728
```

<210> SEQ ID NO 8
<211> LENGTH: 724
<212> TYPE: DNA
<213> ORGANISM: Glycine max
<220> FEATURE:
<221> NAME/KEY: misc_feature
<222> LOCATION: 6, 638, 694, 695, 696, 713, 715, 720, 723
<223> OTHER INFORMATION: n = A,T,C or G

<400> SEQUENCE: 8

```
tctacntatg taatacttca aattgtttga tgagatcgtt aaaaagatat ctgaagagag     60
atataaatat ttttcatttt ctgttctata ttttgggatt tcatcttctt gtctctattg    120
taccaattgt gggtctgttt tgatttgact gtttgtagca cgtttcaatg cacttgttgg    180
agactttctt gtaactttat tgattatagt gaaattattt ctttggtatg aatgatccgt    240 gattttatc cttgcattga ggggttttc actttaaaca aattgtgtct cttgtgtgct     300
tttaatttct attttgctct ctttatattt tagcctgctc ctcacaaatt cttgcaagtt    360
tggaccaatt tatttctact gcctatatta ctttgttatt gtgttggtat attttcttca    420
tcaaagaata tccatttgtg ctttaaattt gggtagttt tgtttcttgc tccacaaatt    480
tttgcagttt tagtggaaag gcccaaccaa tattctcaac attttgggcc ttcctcgaac    540
aaggacccgt aagaatagaa gtttctaaaa tggactgata atcaaatagt tattgagatt    600
tttaattgag ctgcatttgt taagaagtca cggctaanag agttacctag ttgtcagtta    660
tactattttc atgactaagc agcaagcaca gatnnngcag tgatacacaa ccnanagcan    720 atnc                                                                 724
```

<210> SEQ ID NO 9
<211> LENGTH: 728
<212> TYPE: DNA
<213> ORGANISM: Glycine max
<220> FEATURE:
<221> NAME/KEY: misc_feature
<222> LOCATION: 8, 22, 640, 687, 696, 698, 715, 717, 722, 727
<223> OTHER INFORMATION: n = A,T,C or G

<400> SEQUENCE: 9

```
gttctacnta tgtaatactt cnaattgttt gatgagatcg ttaaaaagat atctgaagag     60
agatataaat attttcatt ttctgttcta tattttggga tttcatcttc ttgtctctat    120
tgtaccaatt gtgggtctgt tttgatttga ctgtttgtag cacgtttcaa tgcacttgtt    180
ggagactttc ttgtaacttt attgattata gtgaaattat ttctttggta tgaatgatcc    240
gtgattttta tccttgcatt gagggggttt tcactttaaa caaattgtgt ctcttgtgtg    300
cttttaattt ctattttgct ctctttatat tttagcctgc tcctcacaaa ttcttgcaag    360
tttggaccaa tttatttcta ctgcctatat tactttgtta ttgtgttggt atattttctt    420
catcaaagaa tatccatttg tgctttaaat ttgggtagt tttgtttctt gctccacaaa    480
tttttgcagt tttagtggaa aggcccaacc aatattctca acattttggg ccttcctcga    540
acaaggaccc gtaagaatag aagtttctaa aatggactga taatcaaata gttattgaga    600
tttttaattg agctgcattt gttaagaagt cacggctaan agagttacct agttgtcagt    660
```

-continued

```
tatactattt tcatgactaa gcagcangca cagatntngc agtgatacac aaccnanagc    720 anattcnc                                                             728
```

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10

```
taattttgtc aggctatgga atca                                           24
```

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11

```
tgggtcataa aacaacaaca gc                                             22
```

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12

```
aacacaatcc gtggtgttgt aa                                             22
```

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13

```
ttgaacaagt cattagcaag tagca                                          25
```

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14

```
tggaactgca ttagcatcct t                                              21
```

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15

```
tctacctctc caccagcatg a                                              21
```

```
<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
ggattaggtt gattgttaga cagca                                              25

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
tggagaatat gctctcggtt gt                                                 22

<210> SEQ ID NO 18
<211> LENGTH: 93
<212> TYPE: DNA
<213> ORGANISM: Glycine max

<400> SEQUENCE: 18
gcagttttag tggaaaggcc caaccaatat tctcaacatt ttgggccttc ctcgaacaag        60
gacccgtaag aatagaagtt tctaaaatgg act                                     93

<210> SEQ ID NO 19
<211> LENGTH: 93
<212> TYPE: DNA
<213> ORGANISM: Glycine max

<400> SEQUENCE: 19
gcagttttag tggaaaggcc caaccaatat tctcaacatt ttgggccttc ctcgaacaag        60
gacccgtaag aatagaagtt tctaaaatgg act                                     93

<210> SEQ ID NO 20
<211> LENGTH: 68
<212> TYPE: DNA
<213> ORGANISM: Glycine max

<400> SEQUENCE: 20
actgataatc aaatagttat tgagattttt aattgagctg catttgttaa gaagtcacgg        60
ctaaaaga                                                                 68

<210> SEQ ID NO 21
<211> LENGTH: 68
<212> TYPE: DNA
<213> ORGANISM: Glycine max

<400> SEQUENCE: 21
actgataatc aaatagttat tgagattttt aattgagctg catttgttaa gaagtcacgg        60
ctaaaaga                                                                 68

<210> SEQ ID NO 22
<211> LENGTH: 222
<212> TYPE: DNA
<213> ORGANISM: Glycine max
```

```
<400> SEQUENCE: 22
caagtttgga ccaatttatt tctactgcct atattacttt gttattgtgt tggtatattt       60
tcttcatcaa agaatatcca tttgtgcttt aaattttggg tagttttgtt tcttgctcca     120 caaattttg cagttttagt ggaaaggccc aaccaatatt ctcaacattt tgggccttcc      180
tcgaacaagg acccgtaaga atagaagttt ctaaaatgga ct                        222

<210> SEQ ID NO 23
<211> LENGTH: 222
<212> TYPE: DNA
<213> ORGANISM: Glycine max

<400> SEQUENCE: 23
caagtttgga ccaatttatt tctgctgcct atattacttt gttattgtgt tggtatattt       60
tcttcatcaa aaaatatcca tttgtgcttt aaattttggg tagttttgtt tcttgctcca     120 caaattttg cagttttagt ggaaaggccc aaccaatatt ctcaacattt tgggccttcc      180
tcgaacaagg acccgtaaga atagaagttt ctaaaatgga ct                        222

<210> SEQ ID NO 24
<211> LENGTH: 120
<212> TYPE: DNA
<213> ORGANISM: Glycine max
<220> FEATURE:
<221> NAME/KEY: misc_feature
<222> LOCATION: 65
<223> OTHER INFORMATION: n = A,T,C or G

<400> SEQUENCE: 24
actgataatc aaatagttat tgagattttt aattgagctg catttgttaa gaagtcacgg       60
ctaanagagt tacctagttg tcagttatac tattttcatg actaagcagc aagcacagat     120

<210> SEQ ID NO 25
<211> LENGTH: 120
<212> TYPE: DNA
<213> ORGANISM: Glycine max

<400> SEQUENCE: 25
actgataatc aaatagttat tgagattttt aattgagctg catttgttaa gaagtcacgg       60
ctaaaagagt tacctagttg tcagttatac tattttcatg actaagcagc aagcacagat     120

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
atttgctgaa acactgcgaa c                                                21

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
tccgcgatct ccaatgtc                                                    18
```

```
<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
ggaccttggg tgtggaaaa                                              19

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
caagtatccg cgatctccaa                                             20

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30
gctgaaacac tgcgaacga                                              19

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
acaagtatcc gcgatctcca a                                           21

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
agatgggtgg agctcaagaa c                                           21

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
tctacctctc caccagcatg a                                           21

<210> SEQ ID NO 34
<211> LENGTH: 21
<212> TYPE: DNA
<213> ORGANISM: Artificial Sequence
<220> FEATURE:
<223> OTHER INFORMATION: Primer
```

<400> SEQUENCE: 34
aggagaatac aagcagcacc a                                              21

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ggttcagcag ttggttcctt                                                20

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
cccgatcctt acatttccat t                                              21

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
cgggttttca gtcagattca tt                                             22

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tcccgatcct tacatttcca                                                20

<210> SEQ ID NO 39
<211> LENGTH: 19
<212> TYPE: DNA
<213> ORGANISM: Artificial Sequence
<220> FEATURE:
<223> OTHER INFORMATION: Primer

<400> SEQUENCE: 39
gttttgccgg gttttcagt                                                 19

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
aacaccgtca ccactcacc                                                 19

```
<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
tcaaatcaga accgtatcat caa                                               23

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
tttcggttga tgatgggatt                                                   20

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
gagttgctga aatatccata gatgc                                             25

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
aagtactcag gtggcggttc                                                   20

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
atgctgtcca attaactcac tgat                                              24

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gcatggtaac agggtggagt                                                   20

<210> SEQ ID NO 47
<211> LENGTH: 22
<212> TYPE: DNA
<213> ORGANISM: Artificial Sequence
<220> FEATURE:
<223> OTHER INFORMATION: Primer
```

```
<400> SEQUENCE: 47
gcaacatcca ttttaacaca cc                                              22

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
tactcaggtg gcggttcg                                                   18

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
ggtcccataa taaaatgctg tcc                                             23
```